(12) United States Patent
Chen et al.

(10) Patent No.: US 11,179,360 B2
(45) Date of Patent: Nov. 23, 2021

(54) COMPOSITIONS AND METHODS FOR TREATING PATIENTS SUFFERING FROM GLIOMA OR LEUKEMIA

(71) Applicant: University of Cincinnati, Cincinnati, OH (US)

(72) Inventors: Jianjun Chen, Cincinnati, OH (US); Rui Su, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 16/346,654

(22) PCT Filed: Nov. 2, 2017

(86) PCT No.: PCT/US2017/059645
§ 371 (c)(1),
(2) Date: May 1, 2019

(87) PCT Pub. No.: WO2018/085486
PCT Pub. Date: May 11, 2018

(65) Prior Publication Data
US 2020/0054591 A1     Feb. 20, 2020

Related U.S. Application Data

(60) Provisional application No. 62/416,348, filed on Nov. 2, 2016.

(51) Int. Cl.
| | |
|---|---|
| *A61K 31/194* | (2006.01) |
| *A61P 35/02* | (2006.01) |
| *A61K 9/00* | (2006.01) |
| *A61K 31/203* | (2006.01) |
| *A61K 31/704* | (2006.01) |
| *A61K 31/7068* | (2006.01) |

(52) U.S. Cl.
CPC .......... *A61K 31/194* (2013.01); *A61K 9/0019* (2013.01); *A61P 35/02* (2018.01); *A61K 31/203* (2013.01); *A61K 31/704* (2013.01); *A61K 31/7068* (2013.01)

(58) Field of Classification Search
CPC .................................................. A61K 31/194
See application file for complete search history.

(56) References Cited

U.S. PATENT DOCUMENTS

| | | |
|---|---|---|
| 2012/0202883 A1 | 8/2012 | Hai et al. |
| 2014/0187435 A1 | 7/2014 | Dang et al. |

FOREIGN PATENT DOCUMENTS

| | | | | |
|---|---|---|---|---|
| WO | WO-2015003641 A1 | * | 1/2015 | ........... C07D 401/12 |
| WO | WO-2015123229 A1 | * | 8/2015 | ........... A61K 31/198 |
| WO | 2015138837 A1 | | 9/2015 | |
| WO | 2017076602 A1 | | 5/2017 | |
| WO | 20170210608 A1 | | 12/2017 | |

OTHER PUBLICATIONS

Extended European Search Report (EESR) from corresponding EP Application No. 17866474.4 dated May 28, 2020.
M. R. McKeown et al, Therapeutic Strategies to Inhibit MYC; Cold Spring Harbor Perspectives in Medicine, Oct. 1, 2014, vol. 4, No. 10, pp. 1-16.
Jing-Yi Chen et al, The oncometabolite R-2-hydroxyglutarate activates NF-[kappa]B-dependent tumor-promoting stromal niche for acute myeloid leukemia cells; Scientific Reports, Aug. 31, 2016, vol. 6. No. 1, pp. 1-12.
Xudong FU et al., 2-Hydroxyglutarate Inhibits ATP Synthase and mTOR Signaling; Cell Metabolism, Sep. 1, 2015, vol. 22, No. 3, pp. 508-515.
J.A. Losman et al., (R)-2-Hydroxyglutarate is Sufficient to Promote Leukemogenesis and Its Effects are Reversible; Science, Mar. 29, 2013, vol. 339, No. 6127, pp. 1621-1625.
C. J. Ott et al., BET bromodoma in inhibition targets both c-Myc and IL7$ in high-risk acute lymphoblastic leukemia; Blood, Aug. 17, 2012, vol. 120, No. 14, pp. 2843-2852.
International Search Report and Written Opinion for corresponding PCT Application No. PCT/US2017/059645 dated Mar. 5, 2018.
Javier A. Menendez et al, "Gerometabolites: The pseudohypoxic aging side of cancer oncometabolites"; Cell Cycle, Feb. 3, 2014, vol. 13, 669-709.
Atsushi Terunuma et al., "MYC-driven accumulation of 2-hydroxyglutarate is associated with breast cancer prognosis"; J Clin Invest, Dec. 9, 2014, vol. 124, 398-412.
Dan Ye et al., "R-2-hydroxyglutarate as the key effector of IDH mutations promoting oncogenesis"; Cancer Cell, Mar. 18, 2013; 23(3):274-276.

* cited by examiner

*Primary Examiner* — Yong S. Chong
(74) *Attorney, Agent, or Firm* — Dinsmore & Shohl LLP

(57) ABSTRACT

Pharmaceutical compositions, kits and methods for treating tumors such as glioma and cancers such as leukemia with (R)-2-hydroxyglutarate (R-2HG) are provided, along with therapeutic regimens including treatment of a patient suffering from glioma or leukemia with a MYC-signaling inhibitor followed by or cotemporaneous with treatment with R-2HG, and optionally other chemotherapeutic agents.

6 Claims, 90 Drawing Sheets
Specification includes a Sequence Listing.

NOMO-1　U937　MA9.3ITD　ML-2　MONOMAC 6
MA9.3　THP1　MA9.6　PL21　MA9.6ITD
KOPN-1　SKNO-1　MA9.6RAS　MV4-11　ME-1
KASUMI-1　KOCL69　JURKAT　KOCL48　KOCL50
KOCL45　MA9.3RAS　TF-1　HEL　KOCL51
K562　NB4　　0h　24h　48h　72h　96h

FIG. 1A

NOMO-1　U937　MA9.3ITD　ML-2　MONOMAC 6
MA9.3　THP1　MA9.6　PL21　MA9.6ITD
KOPN-1　SKNO-1　MA9.6RAS　MV4-11　ME-1
KASUMI-1　KOCL69　JURKAT　KOCL48　KOCL50
KOCL45　MA9.3RAS　TF-1　HEL　KOCL51
K562　NB4　　PBS　20μM　100μM　300μM　R-2HG

FIG. 1B

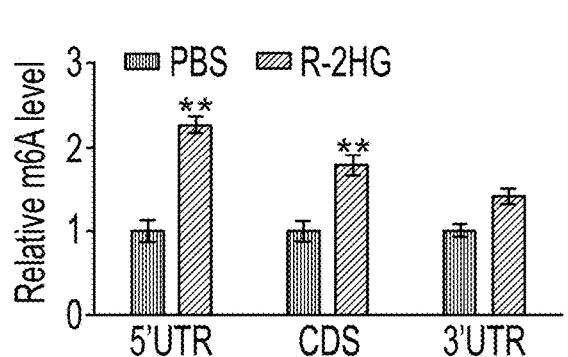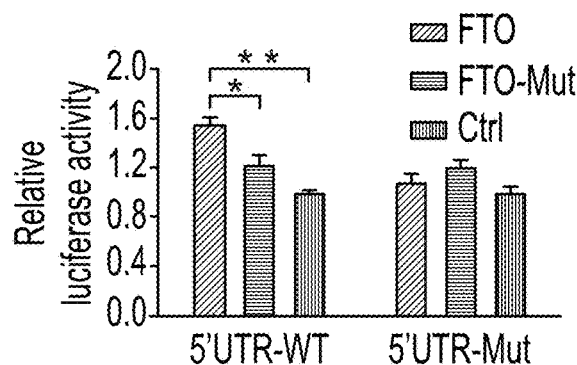
FIG. 4F   FIG. 4G
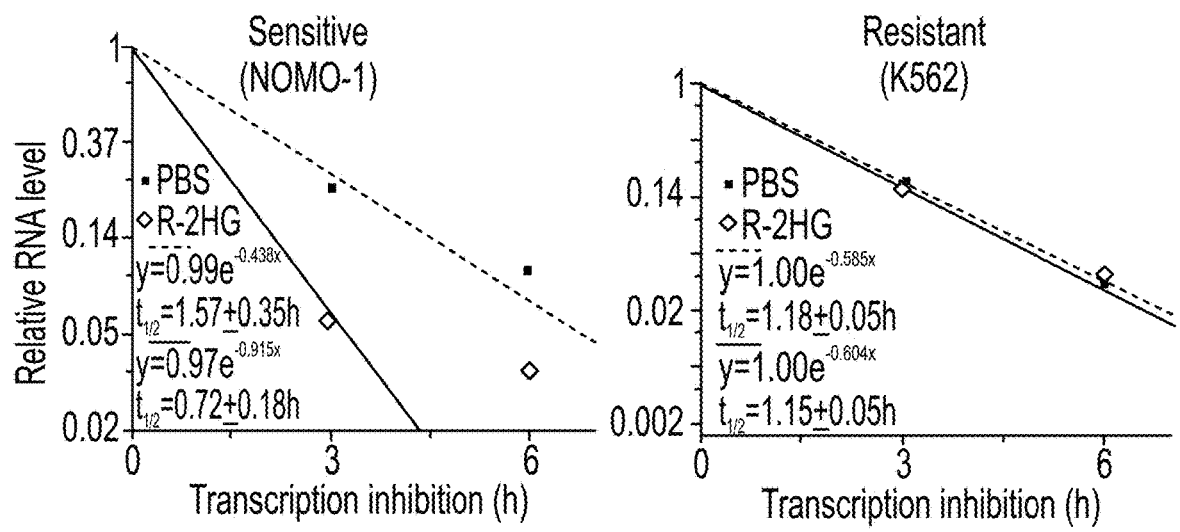
FIG. 4H

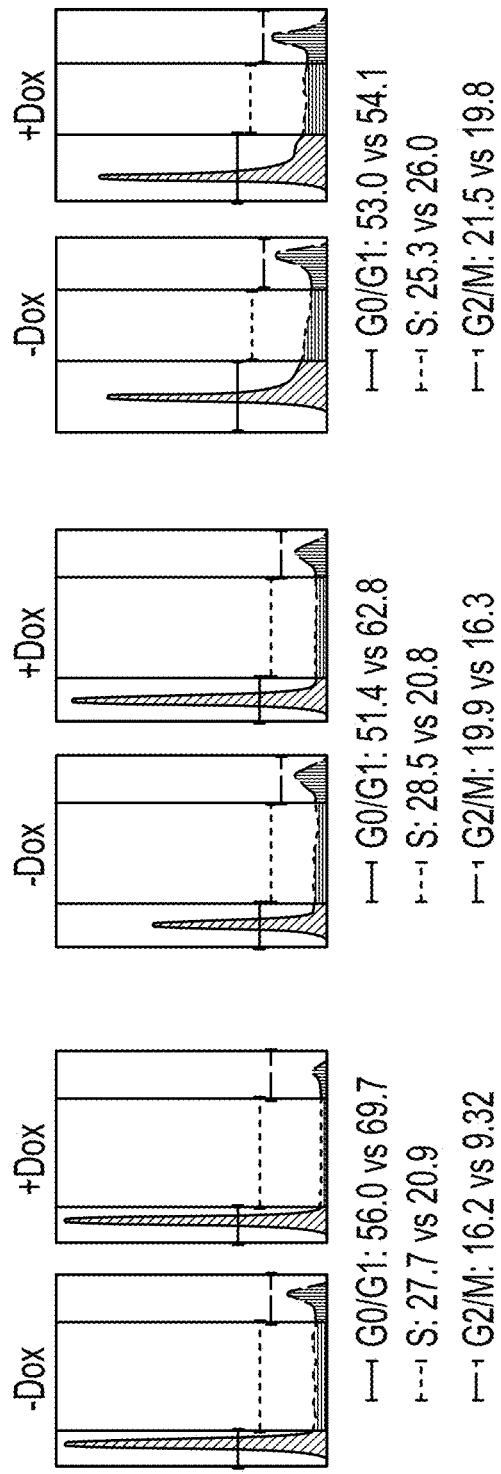
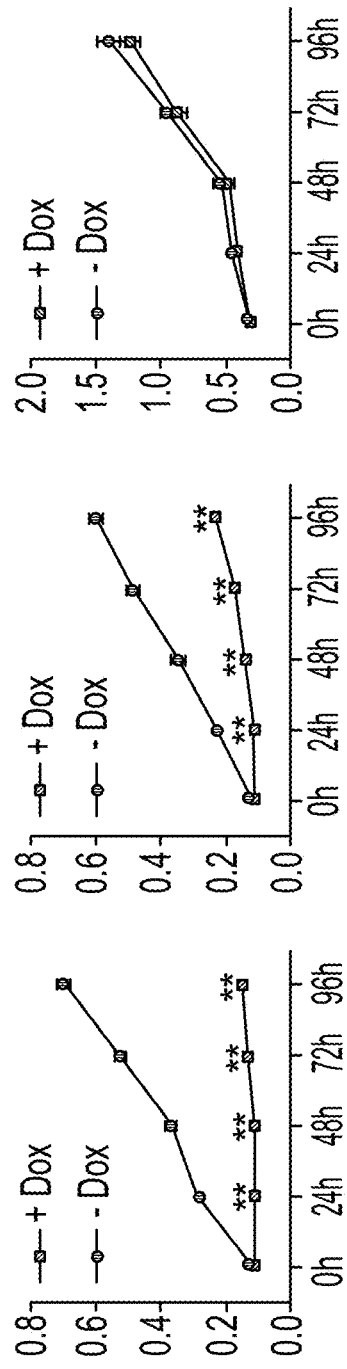
FIG. 5D
FIG. 5E

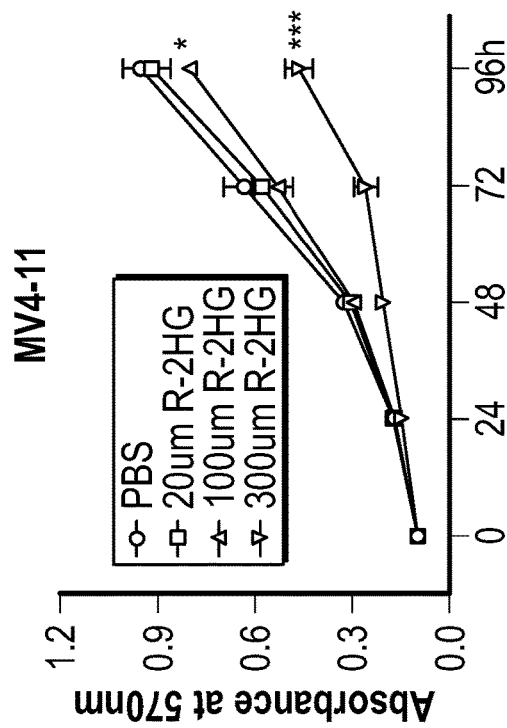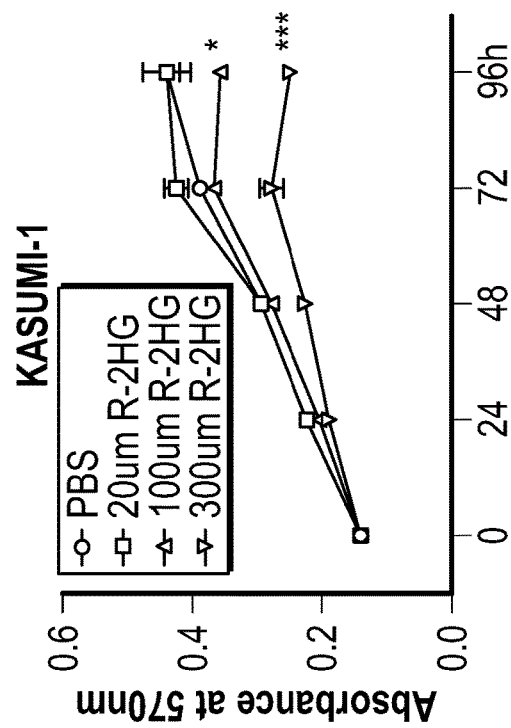
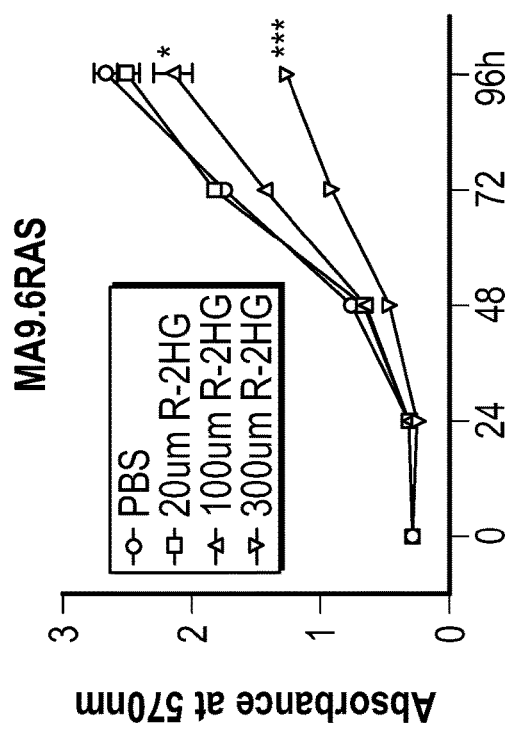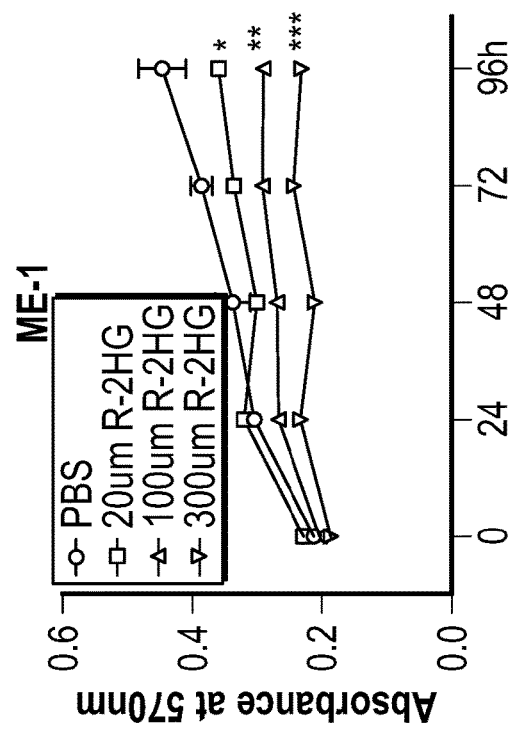
Fig. 6M  Fig. 6N
Fig. 6O  Fig. 6P

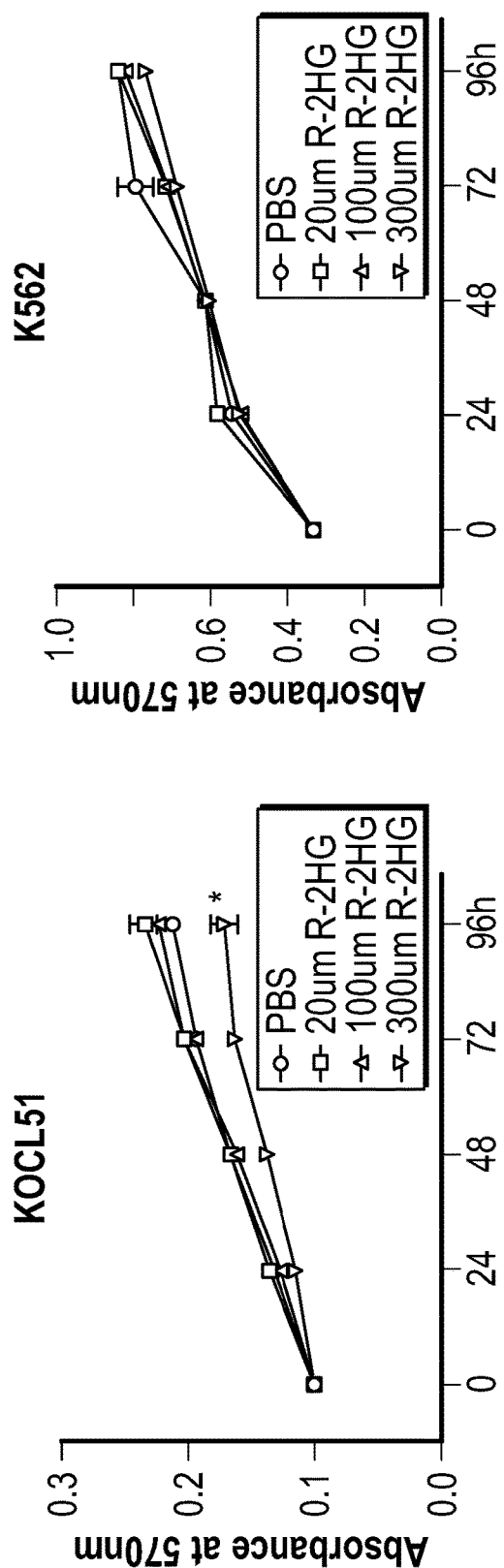
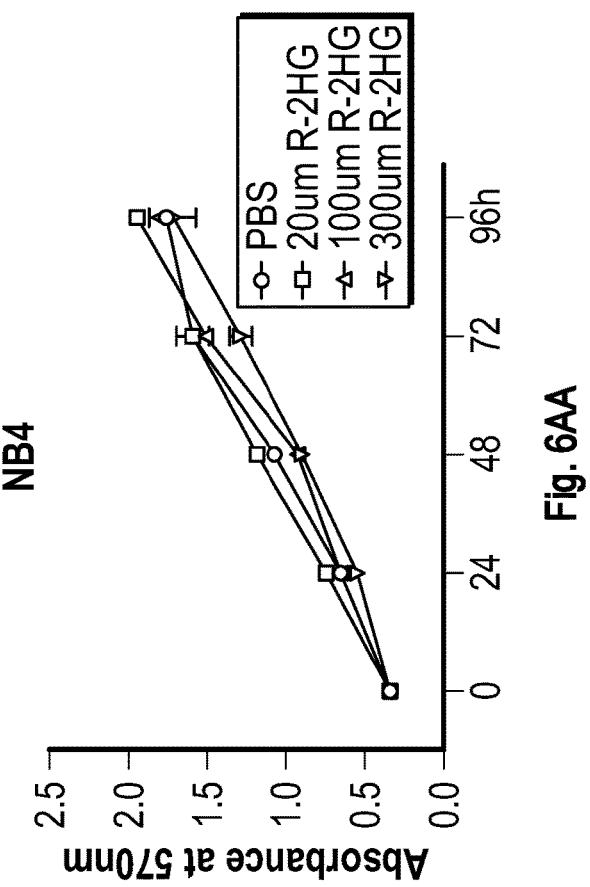

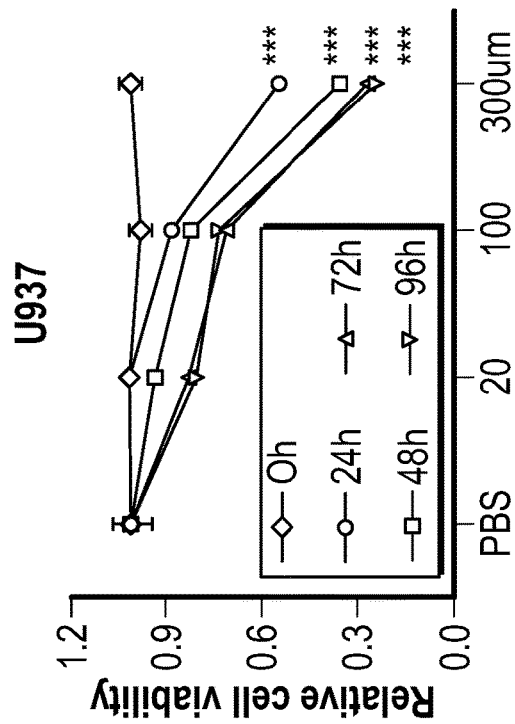
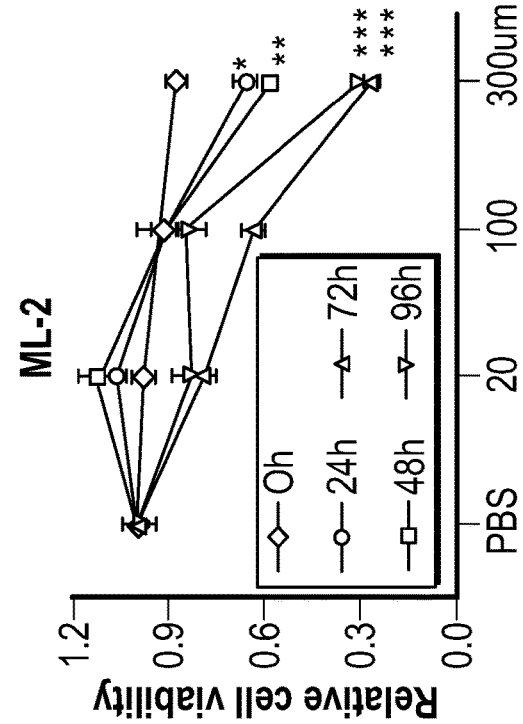
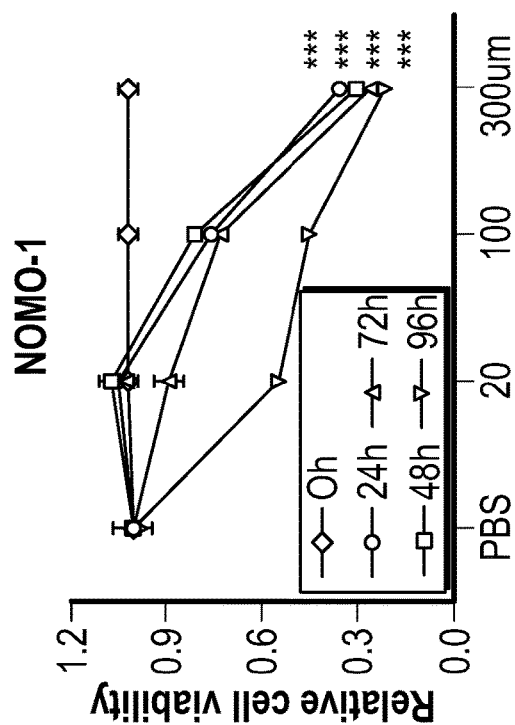
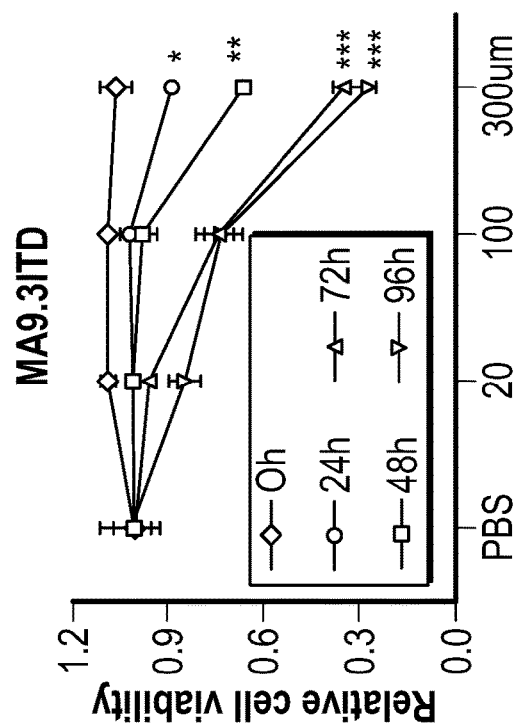

MONOMAC-6

MA9.3

THP1

MA9.6

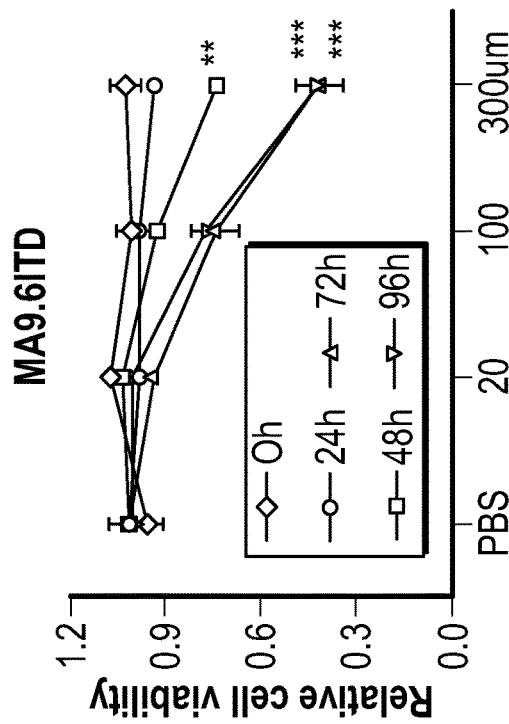
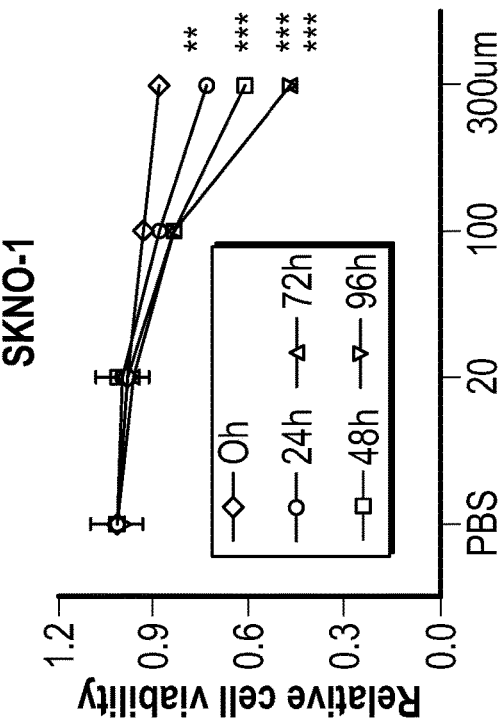
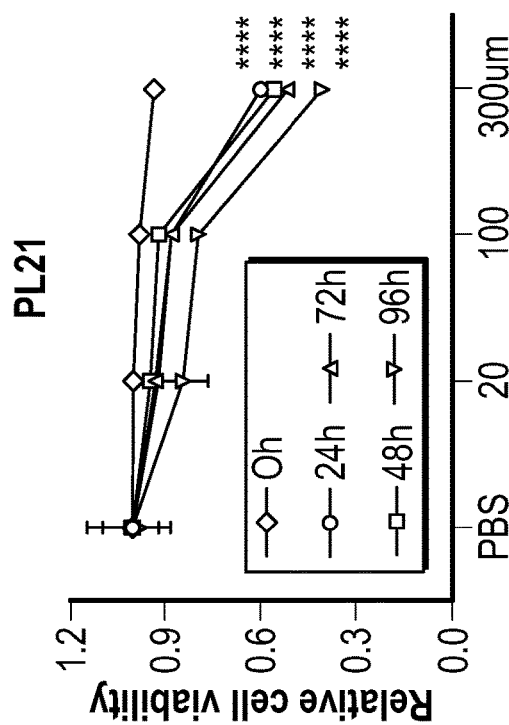
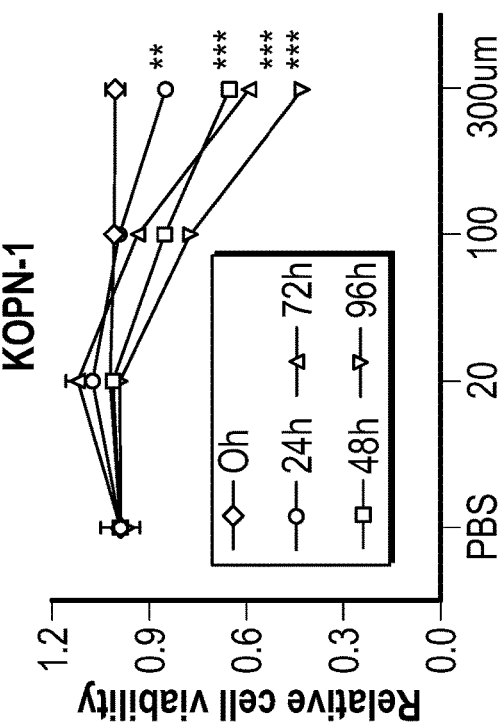
Fig. 7I
Fig. 7J
Fig. 7K
Fig. 7L

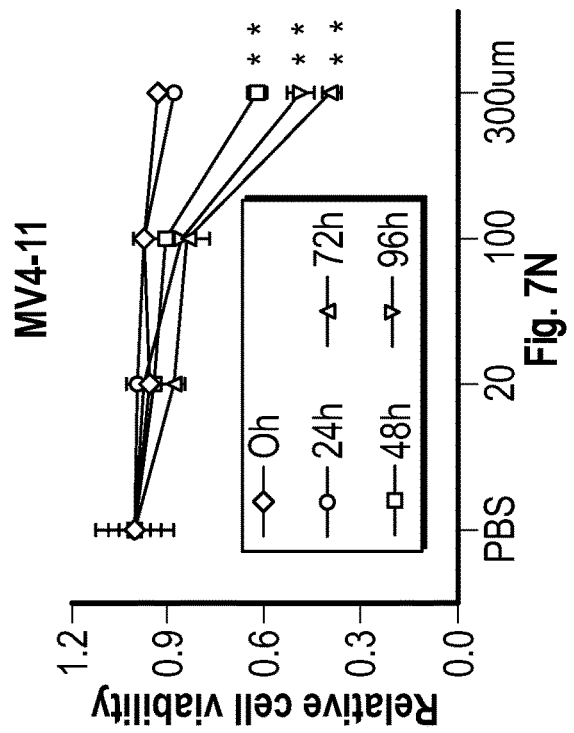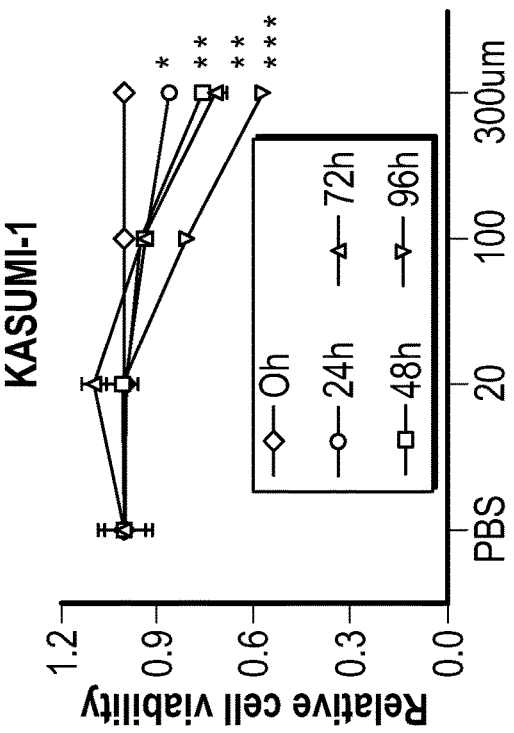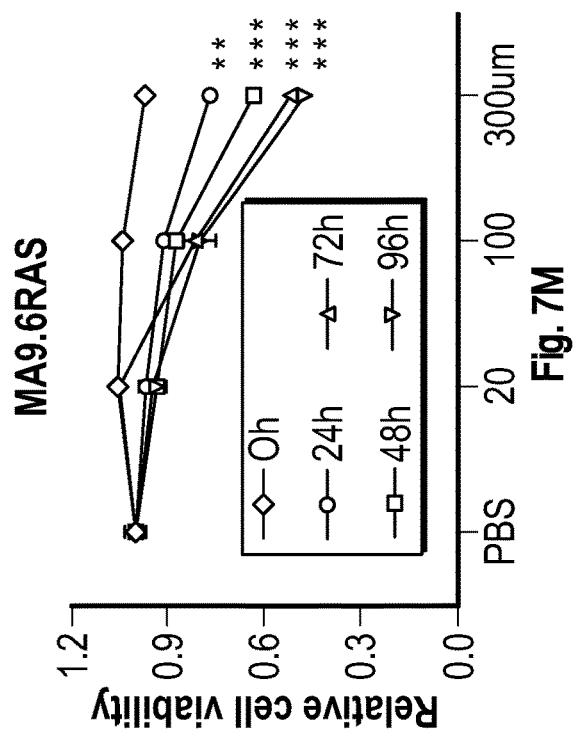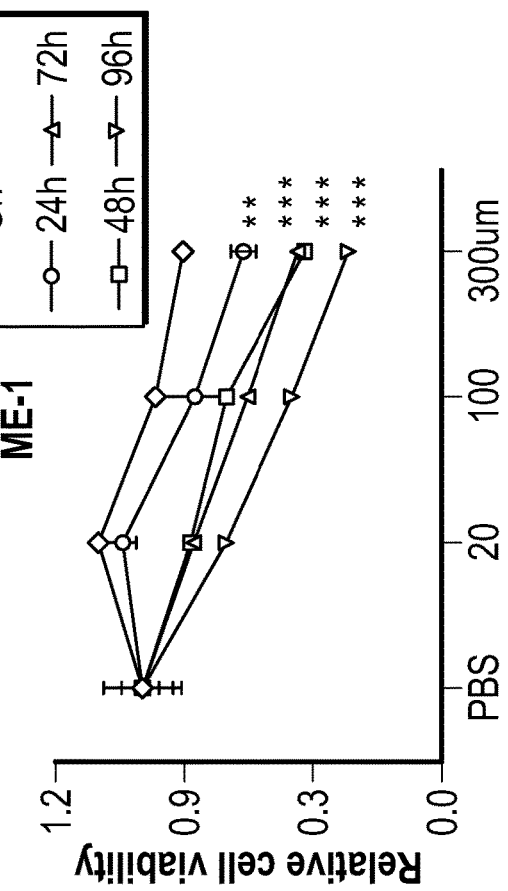

KOCL45

MA9.3RAS

TF-1

HEL

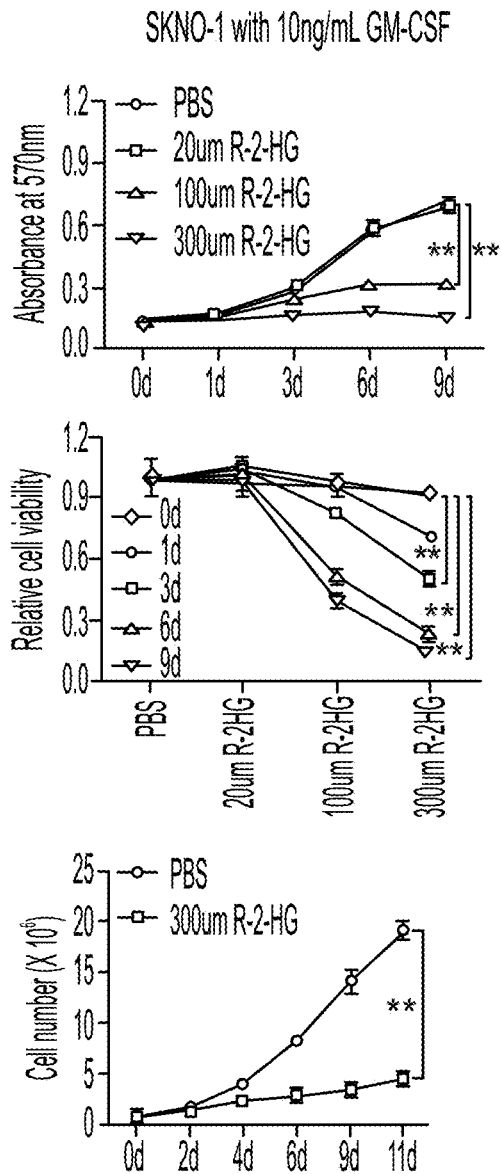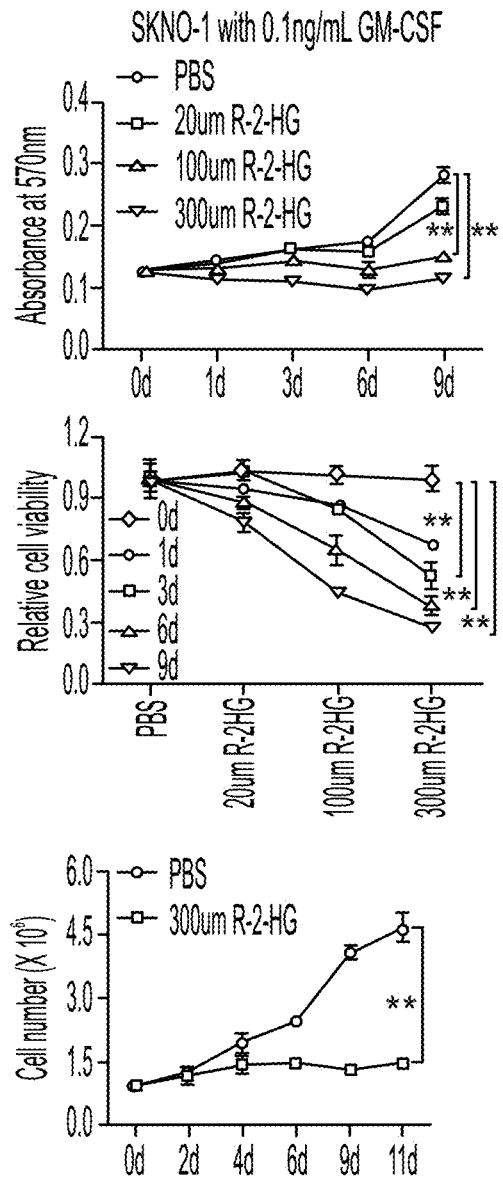
FIG. 9C
FIG. 9D

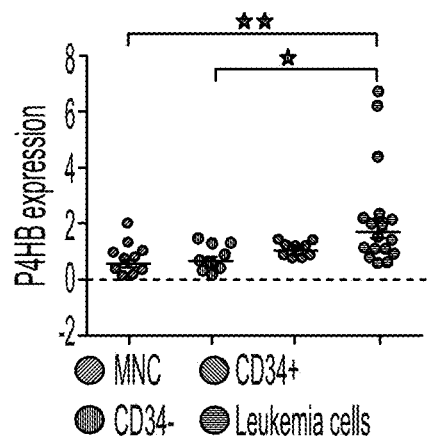
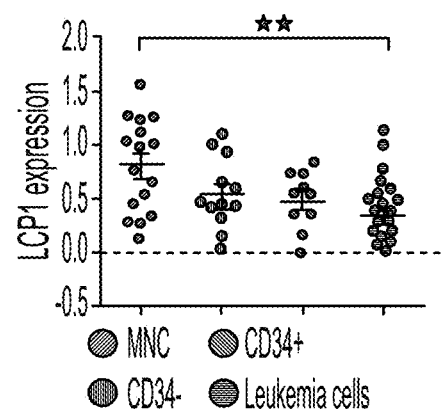
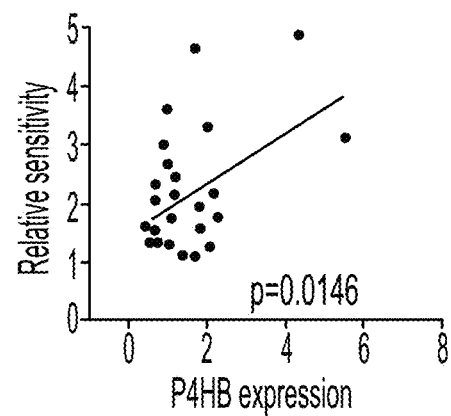
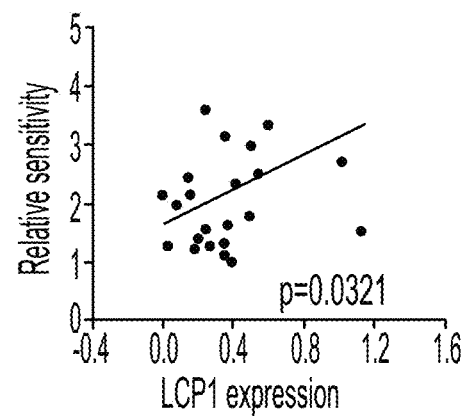
Fig. 11B
Fig. 11C

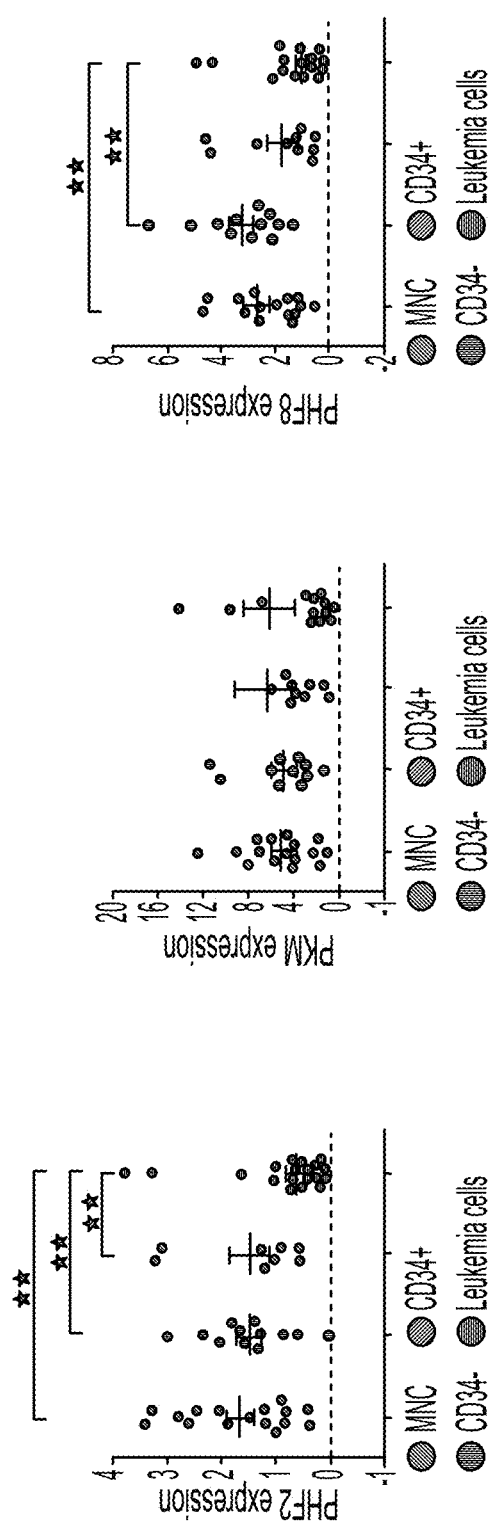
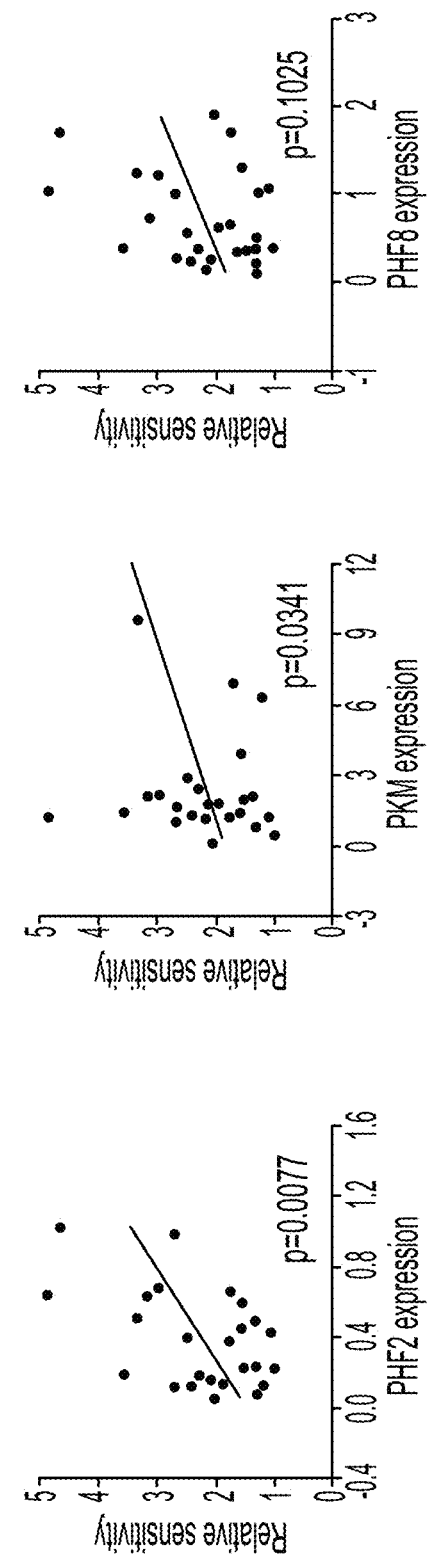
FIG. 11D  FIG. 11E  FIG. 11F

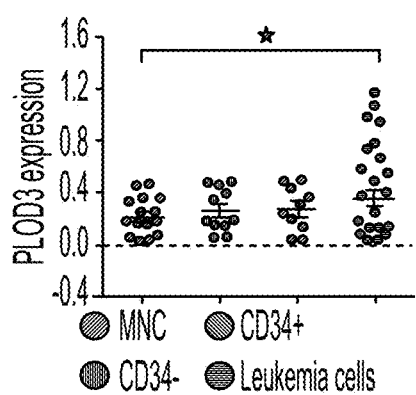
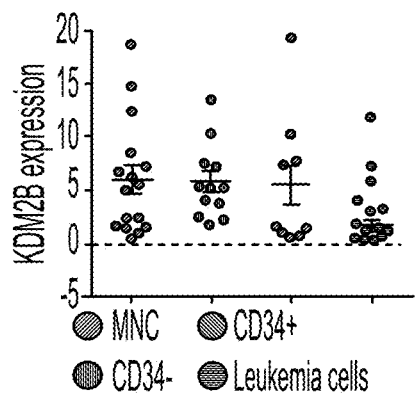
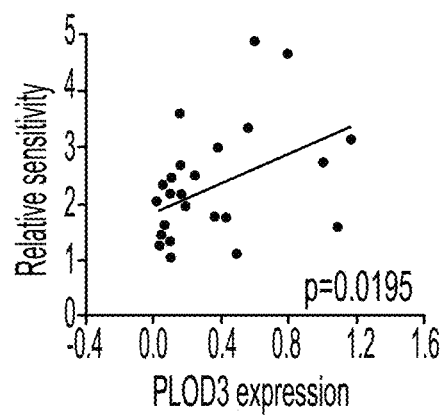
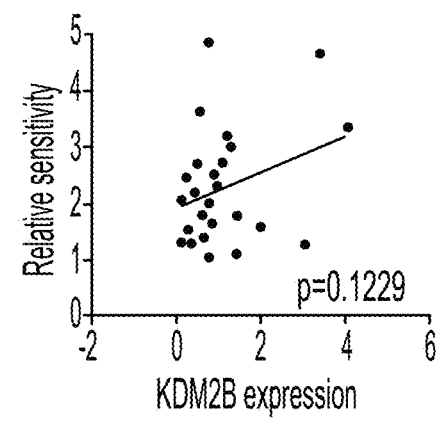
Fig. 11G          Fig. 11H

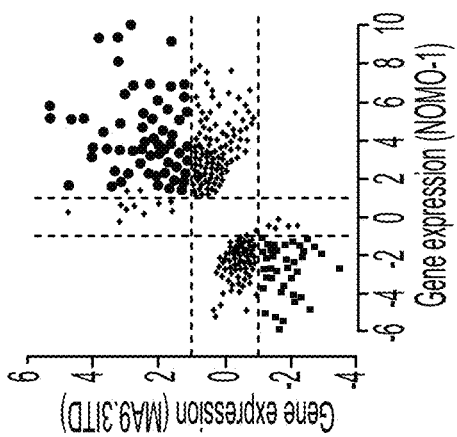
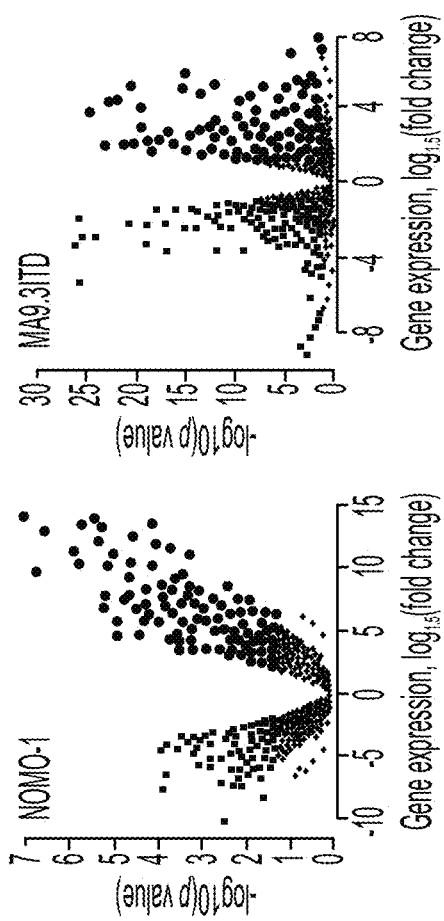
FIG. 12B
FIG. 12A

SEQUENCE LISTING

```
<160> NUMBER OF SEQ ID NOS: 2

<210> SEQ ID NO 1
<211> LENGTH: 35
<212> TYPE: DNA
<213> ORGANISM: Homo sapiens
<220> FEATURE:
<221> NAME/KEY: misc_feature
<223> OTHER INFORMATION: FTO-CDS Forward PCR primer

<400> SEQUENCE: 1
agagctctag aaccaccatg gattacaaag atgac                              35

<210> SEQ ID NO 2
<211> LENGTH: 38
<212> TYPE: DNA
<213> ORGANISM: Homo sapiens
<220> FEATURE:
<221> NAME/KEY: misc_feature
<223> OTHER INFORMATION: FTO-CDS Reverse PCR primer

<400> SEQUENCE: 2
ctaagattgc ggccgcctag ggttttgctt ccagaagc                           38
```

COMPOSITIONS AND METHODS FOR TREATING PATIENTS SUFFERING FROM GLIOMA OR LEUKEMIA

PRIORITY

This application claims priority to U.S. provisional application Ser. No. 62/416,348, the entire disclosure of which is incorporated herein by reference.

GOVERNMENT INTERESTS

This invention was made with government support under contract nos. RO1 CA 178454 and RO1 CA 182528 awarded by the National Institute of Health. The government has certain rights in the invention.

BACKGROUND

Many leukemia cancers, including acute myeloid leukemia (AML), a common hematological cancer of myeloid lineage cells, generally exhibit poor prognosis in the clinic, and new treatment options are in constant demand. Likewise, malignant gliomas, the most frequently observed primary brain tumors, are characterized by a dismal prognosis. Interestingly, recurrent somatic mutations of the genes that code for isocitrate dehydrogenase 1 and 2 (IDH1 and IDH2) have recently been identified in both glioma[1,2] and AML[3,4]. IDH1 and IDH2 are enzymes that catalyze the oxidative decarboxylation of isocitrate to α-KG in an $NAD^+$-dependent manner during the Krebs cycle. All known lesions involve arginine (R), in codon 132 for IDH1 ($IDH1^{R132H}$), 140 and 172 for IDH2 ($IDH2^{R140}$ and $IDH2^{R172}$)[5,6]. In addition to losing their normal catalytic activity, IDH mutations acquire a neomorphic enzymatic function that catalyzes the conversion from α-KG to the R enantiomer of 2-hydroxyglutarate (R-2HG), leading to accumulation of up to millimolar amounts of R-2HG in mutant glioma and leukemia patients[7,8].

R-2HG is structurally similar to α-KG and competitively inhibits a series of Fe (II)/α-KG-dependent dioxygeneases[9]. Accordingly, R-2HG is considered as an "oncometabolite" via impairing DNA and histone epigenetic modification and hypoxic regulation to block cell differentiation and promote tumor transformation[9-13]. Nonetheless, several recent studies reported that inhibition of mutant IDH1(IDHi) did not display significant effect on cell proliferation, migration, DNA and histone methylation; instead, IDHi induced a slight increase in cancer cell proliferation[14-16].

IDH mutations occur in >70% of patients with lower-grade (II-III) brain tumors and 10%-20% of AML patients with overproduction of R-2HG[2,17,18]. Glioma patients with IDH lesions tend to have a better overall survival than those without[1,2,19], and a similar trend was reported in AML patients, although with some ensuing controversy[20-22]. While it was reported that mutant IDH1 and its product R-2HG induce cytokine-independent growth and block erythropoietin (EPO)-mediated differentiation in TF-1 cells, a highly unusual erythroleukemia cell line as it is GM-CSF-dependent[13], the effects of R-2HG or mutant IDH are largely undefined in leukemia cells whose growth is cytokine-independent.

Given the apparently inconsistent data and interpretations of the role of mutant IDH and R-2HG in the onset and prognosis of these deadly cancers, and given the crucial need for understanding these mechanisms, additional exegesis of the meaning and effects, and developing or discouraging therapeutics based on these understandings are an urgent and heretofore unmet need in the art.

SUMMARY

Accordingly, the results of the studies disclosed herein reveal unexpected and broad anti-tumor activity of R-2HG in both leukemia and glioma involving previously unrecognized FTO/$m^6$A/MYC signaling, providing a strong indication for the therapeutic potential of R-2HG. Thus, embodiments of the invention provide novel therapeutic compositions and methods for the treatment of patients suffering from cancers, for example leukemia and glioma.

One Embodiment of the invention provides methods for treating a tumor in a subject in need thereof comprising administering to the subject an effective amount of R-2-hydroxyglutarate (R-2HG). In particular, patients suffering from brain tumors such as primary brain tumors (glioma) are benefited by the instant methods.

Another embodiment is directed to methods for treating cancers, such as leukemia, comprising administering to the subject an effective amount of R-2HG. In some embodiments the patient may be pre-treated with one or more inhibitors of MYC signaling. In other embodiments the patient may be treated in conjunction with one or more inhibitors of MYC signaling and/or one or more chemotherapeutic agents effective for the treatment of the cancer.

Yet another embodiment is directed to pharmaceutical compositions comprising R-2HG and at least one pharmaceutically-acceptable carrier or excipient. The compositions may further comprise one or more agents that inhibit MYC signaling, and/or one or more chemotherapeutic agents effective for treating the target cancer.

Another embodiment is directed to kits assembled for convenient treatment of a patient suffering from a glioma or leukemia, the kits comprising a first vial comprising R-2HG, and at least one second vial comprising an agent effective for inhibiting MYC signaling.

The unexpected intrinsic and broad anti-tumor activity of R-2HG is shown to implicate suppression of FTO/$m^6$A/MYC signaling. In addition, R-2HG activity in sensitizing cancer cells to the treatment of MYC inhibitor(s) and other therapeutic agents is demonstrated. These studies not only reveal the unrecognized activities of R-2HG and the functional importance of FTO, MYC, and RNA epigenetics (herein $m^6$A RNA modification) in R-2HG-associated pathways, which provide novel insights into the molecular mechanisms underlying tumor pathogenesis and drug response, but also provide novel therapeutic strategies to treat cancers with or without IDH mutations.

These and other embodiments and aspects will be further detailed and clarified by reference to the Drawings and to the Detailed Description.

BRIEF DESCRIPTION OF THE DRAWINGS

FIG. 1A-FIG. 1K evidence the anti-leukemic activity of R-2HG. FIG. 1A) Relative cell viabilities of 27 human leukemia cell lines treated with 300 uM cell-permeable R-2HG for 24, 48, 72 and 96 h. The varying color represents different time points; the diameter of the specific indicates the relative cell viability. FIG. 1B) Relative cell viabilities of the 27 cell lines treated with different concentrations of R-2HG at 96 h. The color represents R-2HG concentration; the diameter represents relative cell viability. FIG. 1C) Effects of R-2HG on cell cycle FIG. 1D and cell apoptosis FIG. 1E) in sensitive (NOMO-1) cells. FIG. 1F) Effects of R-2HG on colony-forming capacity and FIG. 1G) cell viability of leukemic blast cells isolated from primary AML patients. FIG. 1H) Schematic illustration of the ex vivo strategy. FIG. 1I) Kaplan-Meier curves showing the leukemic progression of R-2HG- or PBS-treated sensitive cells in vivo. FIG. 1J) Spleen and liver weights from leukemic NSGS mice injected with R-2HG- or PBS-treated NOMO-1 cells. FIG. 1K) Engraftments of PBS- or R-2HG-treated NOMO-1 cells in PB (peripheral blood), BM (bone marrow) and spleen of leukemic NSGS recipient mice. For Kaplan-Meier curve, P values were calculated by log-rank test.

FIG. 2A) Identification of potential α-KG-dependent dioxygenases and signaling pathways responsible for varying sensitivities to R-2HG treatment. Upper panel: the top 10 α-KG-dependent dioxygenases showing positive correlation with R-2HG sensitivity; Lower panel: the top 3 signaling pathways distinguishing sensitive and resistant leukemia cells. FIG. 2B) Global effects of R-2HG treatment in sensitive leukemia cells. Upper panel: the top 10 α-KG-dependent dioxygenases down-regulated by R-2HG; Lower panel, the top 3 signaling pathways suppressed by R-2HG in sensitive leukemia cells. FIG. 2C) Gene set enrichment analysis (GSEA)[28] of significantly differentially expressed genes in four groups of comparisons, seven pathways are enriched in all the comparisons. FIG. 2D) the normalized enrichment scores of MYC, G2M and E2F signaling pathways in the four groups of comparisons.

FIG. 3A) R-2HG treatment increases global $m^6A$ levels in sensitive leukemia cells. MB, methyl blue, represents the RNA loading control. FIG. 3B) R-2HG has little effects on $m^6A$ RNA modification in resistant leukemia cells. FIG. 3C) Schematic illustration of Drug Affinity Responsive Targets Stability (DARTS). FIG. 3D) DARTS assays indicate R-2HG binds direct to FTO, but not ALKBH5. FIG. 3E) Effects of R-2HG on FTO and ALKBH5 expression. FIG. 3F) left panel—effects of FTO overexpression or knockdown (by shRNA) on cell proliferation/growth, right panel—cell viability, FIG. 3G) as well as on the global $m^6A$ modification in MA9.3ITD cells. FIG. 3H) Effects of FTO overexpression or knockdown on cell growth/viability and FIG. 3I) $m^6A$ modification in U937 cells. FIG. 3J) left panel—knockdown of FTO decreases sensitivity to R-2HG treatment in sensitive (NOMO-1) cells, right panel—forced expression of FTO increased sensitivity to R-2HG in resistant (K562) leukemia cells. *, P<0.05; , P<0.01; *, P<0.001; t-test.

FIG. 4A-FIG. 4K provide evidence that R-2HG and FTO regulate MYC expression via manipulating $m^6A$ modification. FIG. 4A) Schematic illustration of $m^6A$-sequencing ($m^6A$-seq) with PBS- or R-2HG-treated sensitive cells (NOMO-1 as a representative). FIG. 4B) The density (line) and frequency (histogram) distributions of $m^6A$ peaks in NOMO-1 cells with R-2HG versus PBS-treatment. Fold enrichment indicates the peaks are more enriched in the R-2HG treated sample than in the PBS-treated sample. FIG. 4C) Summary of changed $m^6A$ peaks after R-2HG treatment. Volcano plot representation of differentially methylated peaks in sensitive cell line with R-2HG treatment versus PBS-treatment. The significantly increased (red) or decreased (blue) $m^6A$ peaks (P<0.01) are highlighted. FIG. 4D) GSEA analysis of genes with a significant increase in $m^6A$ modification on transcripts after R-2HG treatment. FIG. 4E) The $m^6A$ abundance in MYC mRNA in R-2HG- or PBS-treated NOMO-1 cells. FIG. 4F) Gene-specific $m^6A$ qPCR validation of $m^6A$ level changes of MYC in NOMO-1 cells. FIG. 4G) Luciferase and mutagenesis assays. 293T cells were co-transfected with MYC-5'UTR (left panel) or MYC-CDS (right panel) bearing wild-type or mutant ($m^6A$ replaced by T) $m^6A$ motifs, together with wild-type FTO, FTO mutant or control vector. FIG. 4H) Effects of R-2HG on MYC mRNA stability in sensitive (NOMO-1) or resistant (K562) leukemia cells. FIG. 4I) Effects of knockdown $m^6A$ reader YTHDF2 on MYC mRNA stability. FIG. 4J) Profiles of $m^6A$ peaks on MYC transcripts in PBS- or R-2HG-treated sensitive (MA9.3ITD) or resistant (MA9.3RAS) cells with or without FTO knockdown (for MA9.3ITD) or FTO overexpression (for MA9.3RAS), as detected by $m^6A$-seq. FIG. 4K) Model of anti-leukemic function of R-2HG through FTO inhibition. *, P<0.05; , P<0.01; *, P<0.001; t-test. Error bar, mean±SD.

FIG. 5A-FIG. 5K demonstrate that the abundance of FTO and MYC controls sensitivity of leukemic cells to R-2HG. FIG. 5A) Mutant IDH ($IDH1^{R132H}$) also inhibits FTO and MYC expression in sensitive cells (NOMO-1 and U937), FIG. 5B) but not in resistant cells (NB4). FIG. 5C) Effects of $IDH1^{R132H}$ on global $m^6A$ levels in the above sensitive and resistant leukemia cells. FIG. 5D) Function of $IDH1^{R132H}$ on cell cycle, FIG. 5E) proliferation, and FIG. 5F) apoptosis in the above sensitive and resistant cells. FIG. 5G) Venn diagram shows the shared signaling pathways (or gene sets) of the 4 indicated groups of comparisons. The sensitive, resistant and healthy control samples are the R-2HG-sensitive or -resistant leukemic cell lines and normal control samples shown in FIG. 2A. The other samples listed in the plot are human primary AML samples of the TCGA dataset[40]: IDH mutant, the AML samples with mutations in IDH1 and/or IDH2; IDH WT, the AML samples with wild-type IDH genes; IDH WT (NK), the normal-karyotype AML samples with wild-type IDH genes. FIG. 5H) Relative expression levels of FTO, ALKBH5, MYC, CDK4 and CDK6 (the latter two are critical targets of MYC) in primary AML patients with or without IDH mutation as well as in healthy controls. FIG. 5I) Expression pattern of FTO and MYC in sensitive and resistant cells with or without R-2HG treatment. FIG. 5J) MYC overexpression renders sensitive leukemic cells resistant to R-2HG. FIG. 5K) Suppression of the hyper-activated MYC signaling by JQ1 sensitizes R-2HG-resistant leukemic cells to R-2HG or IDH mutant.

FIG. 8A) Left, flow cytometry analyzing the cell cycle in NOMO-1 (upper panel), U937 (middle panel) and NB4 (lower panel) leukemic cells, stained with Propidium iodide (PI). Right, the summaries of cell cycle distributions of the leukemic cells with or without R-2HG treatment, based on three independent experiments. FIG. 8B) Left, flow cytometry of NOMO-1 (upper panel), U937 (middle panel) and NB4 (lower panel) leukemia cells, stained with Hoechst 33342 and Pyronin Y. Numbers in quadrant represented the percent cells at G0 (black), G1 (blue) and S/G2/M (red) stages respectively. Right, the summarized results based on three independent experiments. FIG. 8C) Flow cytometry analysis of apoptosis in NOMO-1, U937 and NB4 cells, stained with FITC-labeled Annexin V and PI, along with the summarized results based on three independent experiments. *, P<0.05; , P<0.01; *, P<0.001; t-test.

FIG. 9A-FIG. 9D show the effects of R-2HG on cell viability and proliferation/growth of two GM-CSF-dependent leukemia cell lines, TF-1 and SKNO-1, under cytokine-normal or -poor conditions. FIG. 9A) Effects of R-2HG on cell proliferation (upper panel; cell density detected by MTT assays), viability (middle panel; detected by MTT assays) and growth (lower level; detected by cell number counts) of TF-1 cells cultured with normal GM-CSF (2 ng/mL) or FIG. 9B) GM-CSF-poor condition (0.1 ng/mL). FIG. 9C) Effects of R-2HG on cell proliferation (upper panel), viability (middle panel) and growth (lower level) of SKNO-1 cells cultured with normal GM-CSF (10 ng/mL) or FIG. 9D) GM-CSF-poor condition (0.1 ng/mL). *, P<0.05; **, P<0.01; t-test.

FIG. 10A) FACS analysis of $CD45^+$ cells in peripheral blood (PB), bone marrow (BM) and spleen of three representative leukemic NSGS recipient mice xeno-transplanted with PBS-treated, or FIG. 10B) R-2HG-treated NOMO-1 cells. Percentage of human $CD45^+$ cells represented the engraftment of human leukemic cells into NSGS mice. FIG. 10C) FACS analysis of $c\text{-}Kit^+$ $Mac\text{-}1^+$ cell populations in BM and spleen of three representative leukemic NSGS recipient mice xeno-transplanted with PBS-treated, or FIG. 10D) R-2HG-treated NOMO-1 cells.

FIG. 11A-FIG. 11K set forth data re the α-KG dependent dioxygenases showing positive correlation with R-2HG sensitivity as detected by RNA-seq, followed by qPCR validation. FIG. 11A) The α-KG dependent dioxygenases that exhibited a positive correlation (r≥0.2) in expression with sensitivity of the leukemic cells to R-2HG treatment as detected by RNA-seq (see FIG. 2A). The top 10 α-KG dependent enzymes that show the most significantly positive correlation are highlighted and qPCR analysis of expression patterns of the aforementioned top 10 α-KG dependent enzymes in 30 human leukemic samples (including the 27 cell lines shown in FIG. 1A and FIG. 1B and 3 primary leukemic samples) and in an expanded cohort of healthy control samples, including 16 normal mononuclear cell (MNC) samples isolated from peripheral blood or bone marrow of healthy donors, and 10 $CD34^+$ and 12 $CD34^-$ MNC samples isolated from cord blood samples, along with Pearson correlation analysis of the correlation between expression levels of the individual α-KG dependent enzymes and sensitivity of the leukemic samples to R-2HG treatment across the 27 leukemic cell lines. The relative expression levels amongst different normal control sample groups and the leukemic sample group (upper panels) and Person correlative analysis (lower panels) of FIG. 11B) P4HB, FIG. 11C) LCP1, FIG. 11D) PHF2, FIG. 11E) PKM, FIG. 11F) PHF8, FIG. 11G) PLOD3, FIG. 11H) KDM2B, FIG. 11I) PHYH, FIG. 11J) FTO, or FIG. 11K) ALKBH7 are shown. *, P<0.05; **, P<0.01; t-test.

FIG. 12A-FIG. 12C set forth the genes that are significantly down-regulated or up-regulated by R-2HG in NOMO-1 and Ma9.3ITD cells, and expression patterns of the α-KG-dependent enzymes in these two cell lines with or without R-2HG treatment, as detected by RNA-seq. FIG. 12A) Summary of the RNA-seq results. Volcano plot representation of differential expression genes in NOMO-1 (left) and MA9.3ITD (right) cell lines with R-2HG treatment versus PBS-treatment. The red and green dots represent the genes with a significant (P<0.05, $\log_{1.5}$ (fold change)>1) increase and decrease, respectively, in expression upon R-2HG treatment. FIG. 12B) The significantly dys-regulated genes in both NOMO-1 and MA9.3ITD cell lines upon R-2HG treatment. Red and green dots represent the genes significantly increased and decreased, respectively, in both cell lines ($\log_{1.5}$ (fold change)>1). FIG. 12C) The expression changes of all the α-KG dependent/related dioxygenases (with expression values in all the four samples) after 300 uM R-2HG treated for 48 hours in NOMO-1 and MA9.3ITD cells.

FIG. 14A) a Venn diagram displaying the core enrichment genes amongst the four gene sets including 'MYC targets V1', 'MYC targets V2', 'G2M checkpoint' and 'E2F targets' shared by both 'sensitive vs. resistant' and 'sensitive vs. healthy control' comparisons. FIG. 14B) Heat map of the 146 shared core enrichment genes. They showed the highest abundance in R-2HG-resistant leukemia cells and the lowest abundance in healthy controls, with a middle level of abundance in R-2HG-sensitive leukemic cells. FIG. 14C) Venn diagram showing the core enrichment genes amongst the aforementioned four gene sets shared by both 'R-2HG-treated NOMO-1 vs. PBS-treated NOMO-1' and 'R-2HG-treated MA9.3ITD vs. PBS-treated MA9.3ITD' comparisons. FIG. 14D) Heat map of the 185 shared core enrichment genes, which were consistently and significantly suppressed by R-2HG in both NOMO-1 and MA9.3ITD cells. FIG. 14E) Relative expression of major component genes (including CCNA2, CDK2, CDK4, CDK6, DDX21, MCM2 and MCM1) of the MYC pathways in sensitive (NOMO-1) cells or FIG. 14F) resistant (K562) cells with or without R-2HG treatment, as detected by qPCR. *, P<0.05; **, P<0.001; t-test.

FIG. 15A) Schematic illustration of enzymes mediating demethylation of DNA, RNA and protein. All these enzymes are the Fe (II)/α-KG-dependent dioxygenase. TET family members (TET1/2/3) mediate demethylation of DNA through converting 5-methylcytosine (5mC) to 5-hydroxymethylcytosine (5hmC). ALKBH5 and FTO, belonging to AlkB family, are responsible for the removal of $m^6A$ modification on RNA. KDM (histone lysine demethylase) and JHMD (Jumonji Domain-containing histone demethylase) catalyzing the demethylation of histone. FIG. 15B) Relative expression of the DNA demethylase genes (TET1/2/3), FIG. 15C) RNA demethylase genes ALKBH5 and FTO, and FIG. 15D) histone demthylase genes KDM2A, KDM4A and JMJD6 in leukemia cells and healthy controls (upper panels), and Pearson correlation analysis between their expression and sensitivities to R-2HG in the leukemia cells (lower panels). FIG. 15E) The 5hmC levels in R-2HG-sensitive leukemic cells, or FIG. 15F) R-2HG-resistant leukemic cells with or without R-2HG treatment for 48 hours. 5hmC levels were determined by dot blot. MB, methylene blue as the loading control. FIG. 15G) The histone methylation status after R-2HG treatment in sensitive leukemic cells, or FIG. 15H) resistant leukemic cells. β-actin was used as loading control. *, P<0.05; **, P<0.01; t-test.

FIG. 16A) Identification of $m^6A$ peaks by two algorithms. The layers from outer to inner represents the $m^6A$ peaks identified by MACS2, exomePeak, and by both algorithms, respectively. FIG. 16B) The density distribution of $m^6A$ peaks across the length of mRNA transcripts. Each region of 5' untranslated region (5' UTR), coding region (CDS), and 3' untranslated region (3' UTR) was split into 100 segments, and the percentage of $m^6A$ peaks that fall within each segment was determined. FIG. 16C) The proportion (upper panel) and enrichment (lower panel) of the $m^6A$ peak distribution in the 5'UTR, start codon, CDS, stop codon or 3'UTR region across the mRNA transcripts. The enrichment was calculated by the number of $m^6A$ peaks normalized by the length of the region. FIG. 16D) Distribution of the $m^6A$ peaks in exonic or intronic regions of protein-coding genes or non-coding genes, or in other regions. FIG. 16E) The $m^6A$ motifs detected by HOMER using a predominant consensus motif DRACH ([G/A/U][G/A] $m^6AC$ [U/A/C]). FIG. 16F) Distribution of the increased $m^6A$ peaks in RNA regions. FIG. 16G) The pie shows the percentage of nucleotides mapped to the increased or decreased $m^6A$ peaks in 5'UTR, start codon, CDS, stop codon, 3'UTR, intron and non-coding RNA (ncRNA). FIG. 16H) Distribution of genes with a significant change in both $m^6A$ level (P<0.01) and RNA expression level in NOMO-1 cells after R-2HG treatment. FIG. 16I) The CLIP-seq data (GSE49339) indicates the predominant binding of YTHDF2 on MYC mRNA.

FIG. 17A) Effects of R-2HG on FTO and MYC expression in sensitive and resistant leukemia cell. R-2HG notably down-regulated FTO and MYC expression at mRNA levels in NOMO-1 (left panel) and MA9.3ITD (middle panel) sensitive leukemia cells, while it had little effects on FTO and MYC expression in K562 (right panel) resistant cells. FIG. 17B) Inhibition of FTO and MYC expression at protein levels by R-2HG in sensitive (NOMO-1 and MA9.3ITD) cells but not in resistant (K562) cells. FIG. 17C) Effect of FTO on MYC expression. Forced expression of wild-type FTO increased MYC expression compared with mutant FTO or control group, and FTO knockdown decreased MYC expression, in sensitive (MA9.3ITD) leukemia cells. FIG. 17D) Knockdown of YTHDF2 expression caused a significant increase in MYC expression level. **, P<0.01; t-test.

FIG. 18A) The 5 core gene sets shared by four groups comparisons, including 'IDH mutant vs. IDH WT' (i.e., AML patients with IDH mutations vs. AML patients without IDH mutations), FIG. 18B) 'IDH mutant vs. IDH WT (NK)' (i.e., AML patients with IDH mutations vs. AML patients with normal karyotype and without IDH mutations), FIG. 18C) 'sensitive vs. resistant' (i.e., R-2HG-sensitive leukemic cell lines vs. R-2HG-resistant leukemic cell lines; see the samples in FIG. 2A), and FIG. 18D) 'sensitive vs. healthy control' (i.e., R-2HG-sensitive leukemic cell lines vs. healthy control samples; see the samples in FIG. 2A). FIG. 18E) The $IC_{50}$ values of JQ-1 in AML patients with IDH mutations or wild-type IDH genes. FIG. 18F) The synergistic effects between R-2HG and clinical chemotherapeutic drugs, including ATRA, Daunorubicin, A Z A and Decitabine, on inhibiting leukemic cell viability (using MONOMAC 6 as a representative). *, P<0.05; **, P<0.01; t-test.

FIG. 19A) R-2HG suppresses cell proliferation/growth in the 8 brain tumors cells. All the cells were plated in 96-well plate at 5,000-10,000 cells/well and the cell proliferation was assessed by MTT assays. FIG. 19B) R-2HG inhibits cell viability of glioma cells in a dose-dependent manner. The relative cell viability of the 8 glioma cell lines were detected by MTT 96 hours post-treatment with 20 μM, 100 μM or 300 μM R-2HG. FIG. 19C) R-2HG decreases cell viability of glioma cells in a time-dependent manner. All the brain tumor cells were treated with 300 μM R-2HG for 24, 48, 72 or 96 hours. *, P<0.05; **, P<0.01; t-test.

DETAILED DESCRIPTION

Figure 1C:
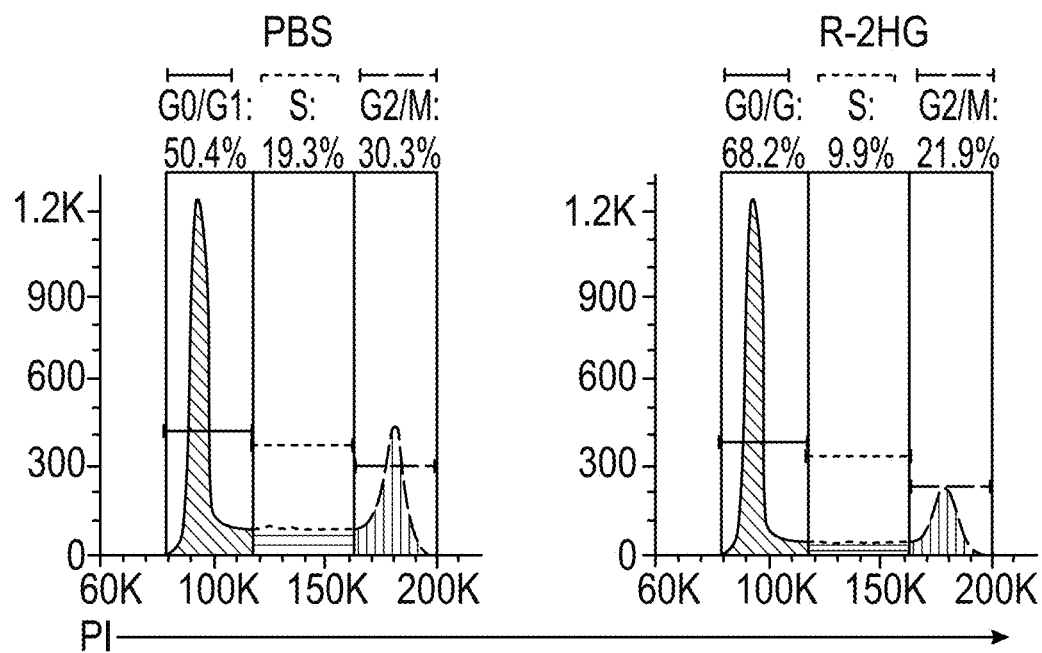

Prior to the investigations set forth herein, R-2-hydroxyglutarate (R-2HG), which is accumulated in subjects exhibiting Isocitrate Dehydrogenase 1 and 2 (IDH1 and IDH2) mutations, was widely considered to be an oncometabolite via interfering with α-ketoglutarate (α-KG)-dependent dioxygenases. However, these investigations reveal that R-2HG actually exerts a broad anti-leukemic activity in vitro and in vivo by inhibiting leukemia cell proliferation/viability and promoting cell-cycle arrest and apoptosis. Mechanistically, in R-2HG-sensitive cells, R-2HG dramatically induces global $N^6$-methyladenosine ($m^6A$) RNA modification, mainly through suppression of the expression and activity of FTO, an RNA demethylase. Consequently, the increased $m^6A$ modification causes less stability of MYC transcripts, leading to the suppression of MYC-associated signaling pathways. Mutant IDH recapitulates the effect of R-2HG. Interestingly, while high abundance of FTO sensitizes leukemic cells to R-2HG, hyperactivation of MYC signaling confers resistance, which can be reversed by pharmaceutical inhibition of MYC signaling. R-2HG also shows synergistic anti-tumor effects with other therapeutic agents in leukemia and glioma. Thus, the data highlights the therapeutic potential and efficacy of treatment of cancer with R-2HG.

Notably, R-2HG predominantly increases global $m^6A$ RNA modification, rather than histone or DNA methylation, in sensitive leukemia cells, as detected by both $m^6A$ dot blot and transcriptome-wide $m^6A$-seq assays. The sensitivity of leukemic cells to R-2HG is positively correlated with the expression level of FTO, an Fe(II)/α-KG dependent $m^6A$ demethylase[33,41], and R-2HG binds directly to FTO (suppressing its enzymatic activity) and strikingly, R-2HG treatment also causes the down-regulation of FTO expression through unrecognized mechanism(s). Experiments set forth herein show that FTO plays an oncogenic role in leukemia and its knockdown mimics effect of R-2HG. Together, our data suggest that FTO is a direct target of R-2HG and its functional/expressional suppression caused by R-2HG is likely responsible for R-2HG-mediated anti-leukemic effect and increase of global $m^6A$ modification. Further, the high abundance of FTO expression is a feature of R-2HG-sensitive leukemic cells, and manipulating expression level of FTO can change the sensitivity/resistance of leukemic cells to R-2HG.

A few leukemic cell lines are resistant to R-2HG treatment. RNA-seq profiling assays indicate that R-2HG-resistant leukemic cells have a hyper-activation of the MYC, G2M and E2F signaling pathways, relative to R-2HG-sensitive leukemic cells, while the latter has a relatively higher activation of these pathways than healthy controls. Interestingly, these signaling pathways are also highly activated in AML patients carrying IDH mutations. Moreover, forced expression of MYC, a master transcript regulator and universal transcriptional amplifier that regulates all these pathways[38,39], renders R-2HG-sensitive leukemic cells resistant to R-2HG. Conversely, JQ1 inhibition of MYC signaling confers R-2HG-sensitivity in R-2HG-resistant leukemic cells. Thus, the R-2HG resistance in leukemic cells may be attributed to the hyper-activation of MYC signaling (and the associated pathways).

Figure 4A:
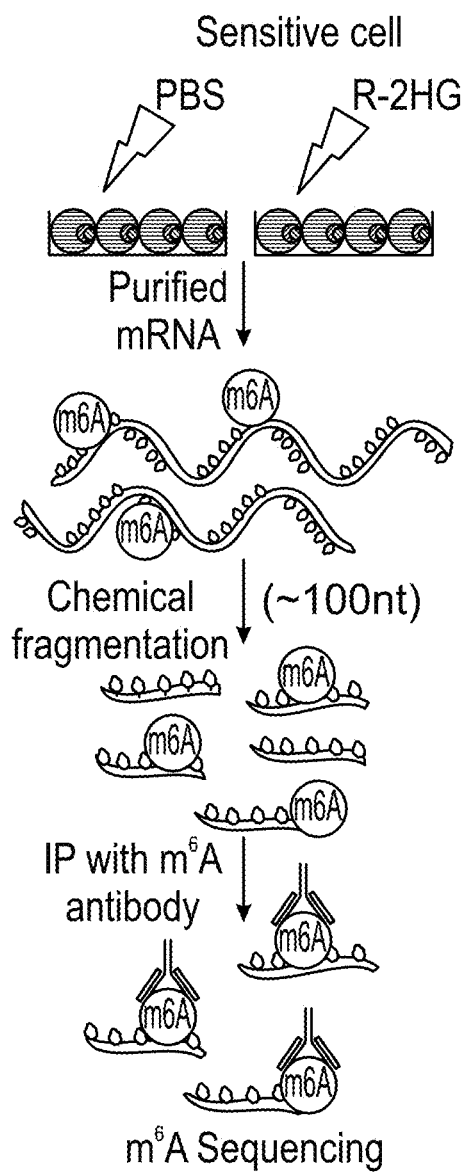
Figure 4B:
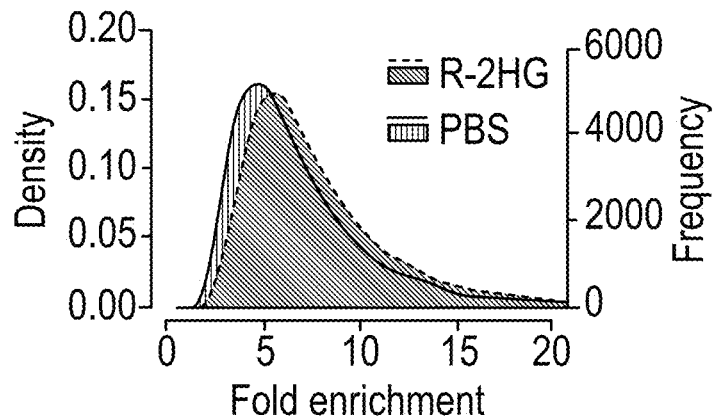
Figure 4C:
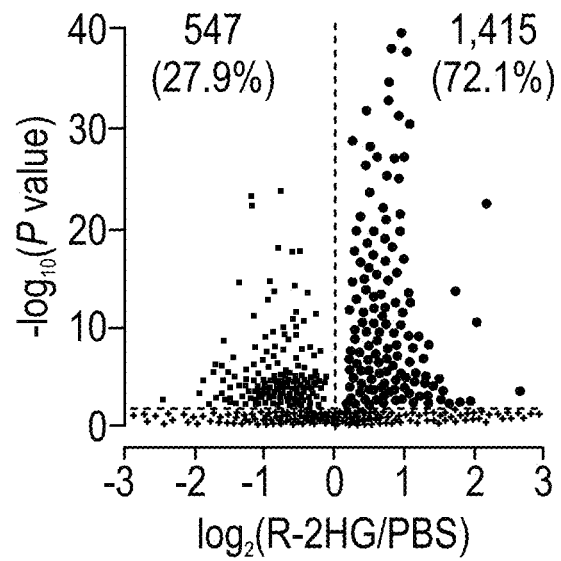
Figure 4D:
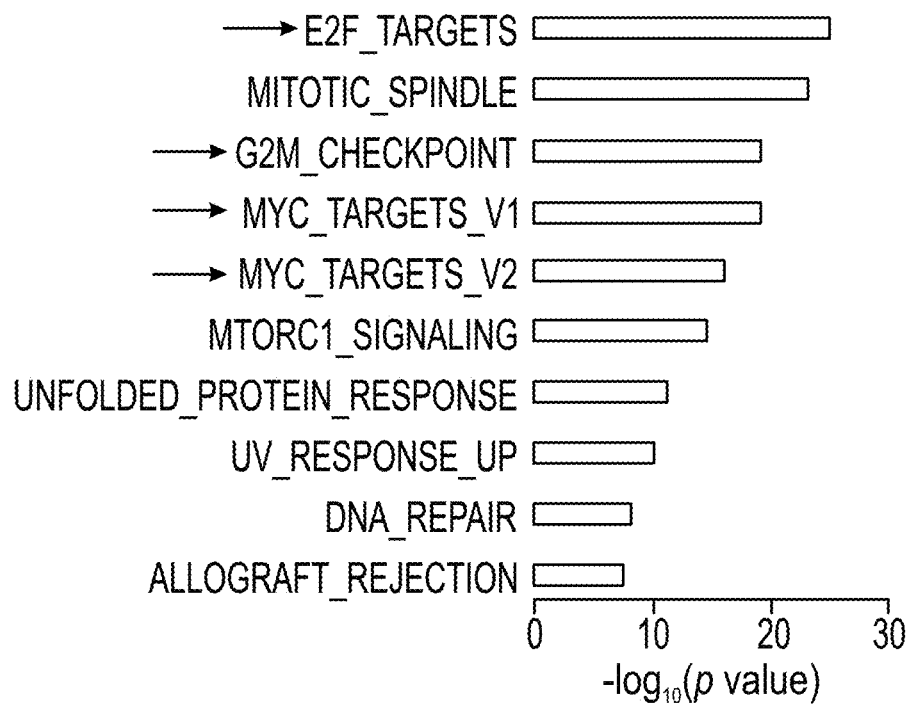
Figure 4E:
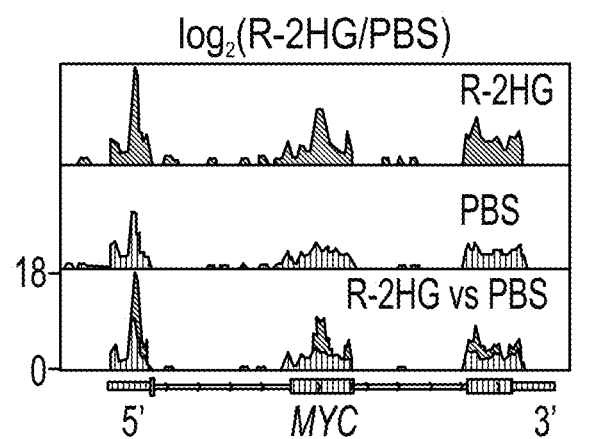
Figure 4I:
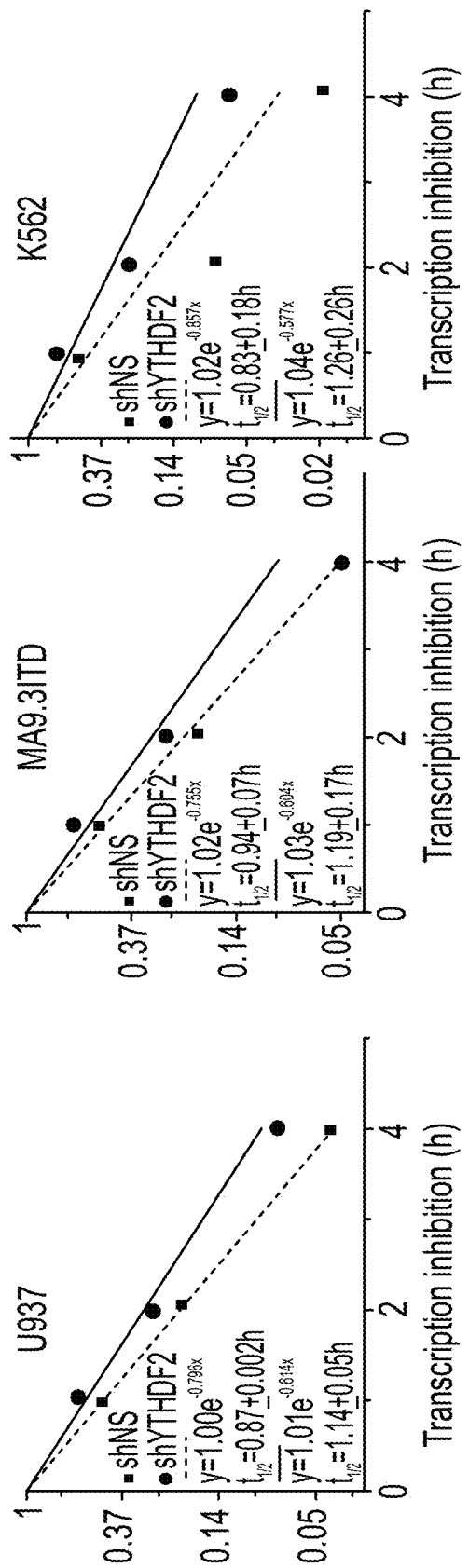
Figure 4J:
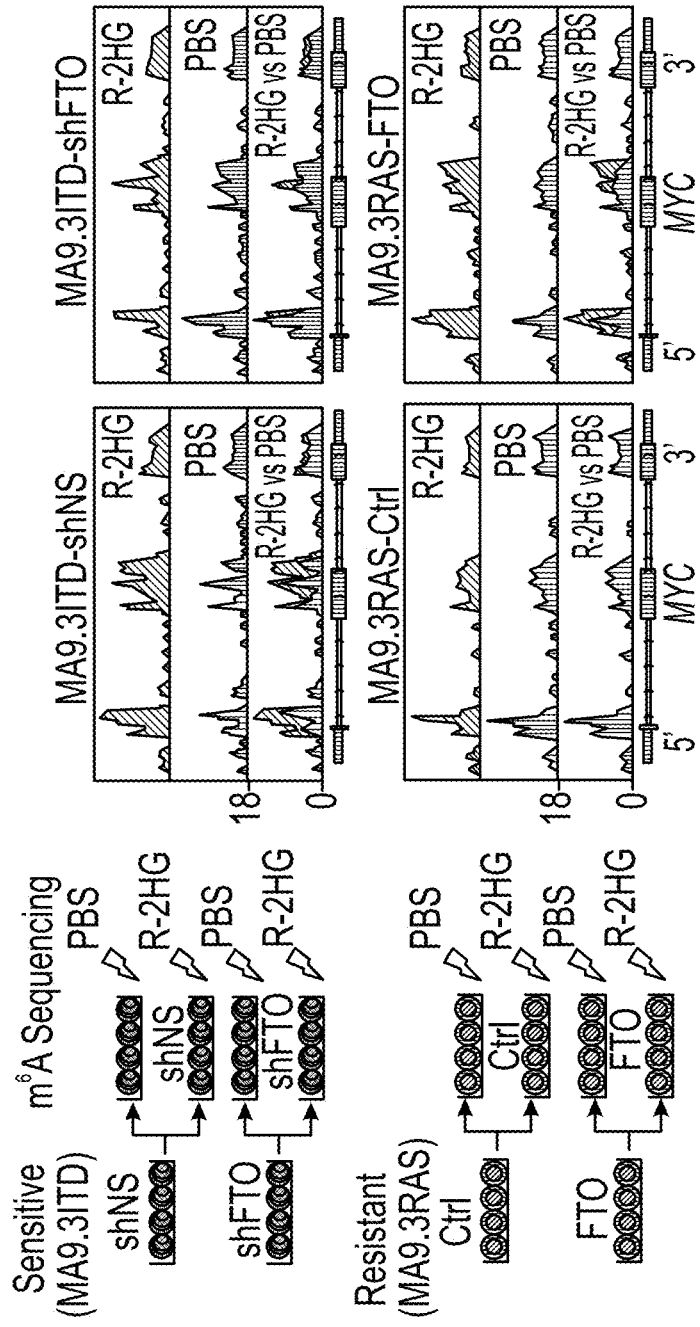
Figure 4K:
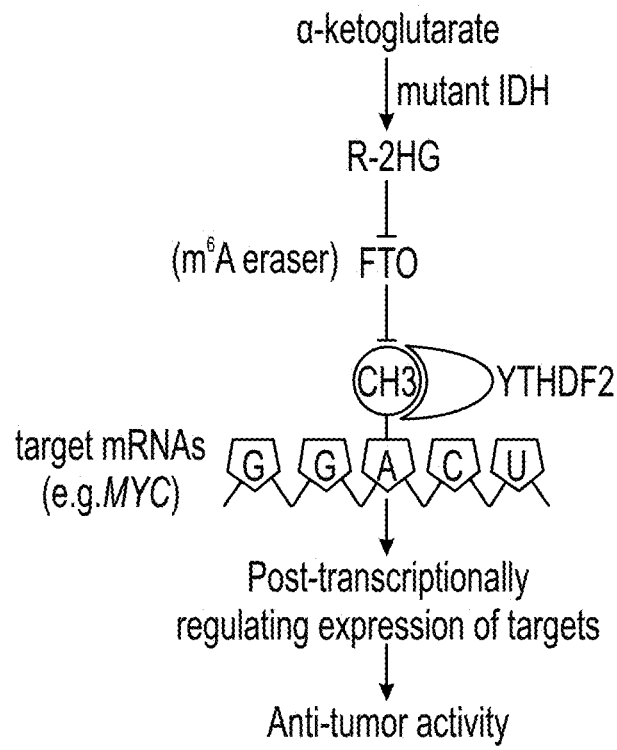

Intriguingly, the MYC, G2M and E2F signaling pathways are also the most responsive pathways suppressed by R-2HG in sensitive leukemic cells. Examples set forth herein show that R-2HG treatment causes a substantial increase in the abundance of $m^6A$ modification on MYC mRNA transcripts, especially at the 5'UTR and CDS regions, in R-2HG-sensitive leukemic cells (but not in R-2HG-resistant ones), associated with a substantial down-regulation of MYC expression. Rescue assays and luciferase reporter/mutagenesis assays suggest that the effect of R-2HG on $m^6A$ modification and regulation of MYC expression relies on R-2HG-mediated suppression of FTO activity/expression and FTO's demethylase activity, as well as the associated changes in $m^6A$ modification on MYC transcripts. Moreover, R-2HG-mediated increase of $m^6A$ modification on MYC transcripts tends to be recognized by $m^6A$ "reader" YTHDF2[37] and eventually leads to mRNA degradation. Thus, these studies reveal a new molecular mechanism by which R-2HG suppresses the activity/expression of FTO, and thereby increases the $m^6A$ abundance on key downstream target transcripts (e.g., MYC) and post-transcriptionally regulates their expression (e.g., through RNA degradation), leading to anti-tumor effect (FIG. 4K). Together, this work reveals a previously unrecognized, $m^6A$-modification-associated oncogenic signaling (i.e., FTO→$m^6A$ modification→MYC, etc.) in leukemic cells and its suppression by R-2HG is a major mechanism responsible for R-2HG's broad anti-leukemic effect.

Collectively, the data suggest that the sensitivity/resistance of leukemic cells to R-2HG is controlled by the concentration of FTO and MYC, and is dose-dependent. The higher level of FTO abundance is often associated with the higher sensitivity of the leukemic cells to R-2HG, likely attributed to the higher functional importance of FTO and its associated oncogenic signaling on the survival of such leukemic cells. Although MYC and its associated signaling pathways are critical downstream targets of FTO and R-2HG, too high abundance of MYC likely cannot be sufficiently depressed by R-2HG (or FTO suppression) to a threshold that can trigger anti-leukemic effect. Thus, hyperactivation of MYC signaling pathway(s) renders leukemic cells resistant to R-2HG.

While exogenous mutant IDH displays a similar anti-leukemic effect to R-2HG in R-2HG-sensitive leukemic cells, it shows no inhibitory effect in resistant cells in which MYC signaling is hyper-activated. Interestingly, R-2HG treatment causes a substantial decrease in global 5hmC abundance (FIG. 16F) in R-2HG-resistant cells, which might be due to R-2HG-mediated inhibition of the activity of TET2[13,42], a well-recognized tumor suppressor gene[42,43]. Thus, while IDH mutant's potential anti-leukemic effect is abrogated by hyper-activated MYC signaling, IDH mutant may also contribute to leukemic cell survival to some degree by inhibition of TET2, and this may explain why IDH mutations still occur in 10%-20% of AML cases[17,18] and such AML patients are more responsive to hypo-methylating agents[44].

Also as demonstrated herein, R-2HG decreases cell proliferation and viability in human brain tumor cells, suggesting that R-2HG may have an intrinsic anti-tumor activity in a broad array of tumors; although such activity can be compromised by a strong oncogenic signaling (e.g., MYC signaling) in patients with IDH mutations. Remarkably, this data demonstrates that R-2HG exhibits a synergistic effect with JQ1 and a cohort of first-line therapeutic agents (e.g., azacitidine, decitabine, ATRA, and daunorubicin) in inhibition of leukemic cell growth/survival. Consistent with these findings, previous studies show that leukemia patients with IDH mutations tend to be more sensitive to treatment with hypomethylating agents such as azacitidine and decitabine[44], ATRA[45], or standard chemotherapy (daunorubicin and others)[20,21], than those without. Similarly, glioma patients carrying IDH mutations also have a more favorable overall survival than those without[2,19], which might also be attributed to the possibility that endogenous R-2HG sensitizes tumor cells to standard therapies (e.g., TMZ) applied to brain tumor patients. Thus, besides its intrinsic anti-tumor activity, R-2HG likely also contributes to the drug response of cancer cells. Thus, the combinations of R-2HG (exogenous one, or that induced by endogenous IDH mutations) with MYC inhibitor(s) and other widely used therapeutic agents (e.g., Azacitidine, Decitabine, ATRA, or Daunorubicin) may represent more effective novel therapeutic strategies to treat leukemia and glioma (and likely also other cancer types). It is contemplated that different subtypes of cancers may need different combinations of treatment.

Some embodiments provide methods of treating a tumor or a cancer in a subject in need thereof comprising administering to the subject an effective amount of R-2-hydroxyglutarate (R-2HG). According to more specific embodiments, the subject is suffering from a brain tumor, and according to even more specific embodiments the brain tumor comprises a primary brain tumor/glioma. In other specific embodiments, the cancer comprises a hematologic cancer, and even more specifically, the cancer comprises leukemia. According to very specific embodiments, the cancer comprises acute myeloid leukemia (AML). Notably, recent data generated by the present investigators suggests that S-2HG may be equally as effective in the methods disclosed herein and work is currently underway to confirm with respect to both S-2-HG and racemic 2-HG.

According to one embodiment, at least one agent effective for inhibiting MYC signaling prior is administered to the patient prior to administering the R-2HG. Exemplary such agents are set forth in Table 4. Patients exhibiting a resistant phenotype either prior to commencing treatment or acquired epigentically after initiation of treatment may be particularly benefited by this embodiment. For example, the patient may exhibit a mutant form of IDH1 and/or an IDH2.

According to another embodiment, one or more chemotherapeutic agents may be administered in conjunction with the R-2HG. Exemplary chemotherapeutic agents include but are not limited to all trans retinoic acid (ATRA), azacitidine (AZA), daunorubicin, and decitabine. "In conjunction" as utilized herein is intended to mean as part of the same therapeutic regimen and includes, for example, prior to, subsequent to, and cotemporaneous with administration of R-2HG. In specific embodiments administering comprises cotemporaneous administration. In other specific embodiments administering comprises administering as a secondary therapeutic subsequent to tolerance. In additional specific embodiments, administering comprises administering at least one small molecule MYC-signaling inhibitor selected from Table 4, R-2HG, and at least one chemotherapeutic agent in the same therapeutic regimen.

In some embodiments, R-2HG may be modified, for example to increase membrane permeability. According to specific embodiments, the R-2HG is ester modified. For purposes of the Examples set forth herein "R-2HG" is ester-modified R-2HG. In very specific embodiments, the R-2HG is ester modified in accordance with the following structure:

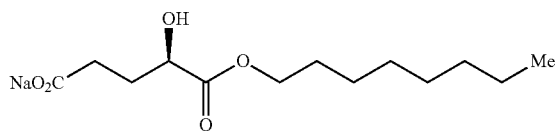

Another embodiment is directed to a pharmaceutical composition comprising R-2HG (or S-2HG, or a racemic mixture thereof), and one or more pharmaceutically-acceptable carriers and/or excipients. According to more specific embodiments, the pharmaceutical composition further comprises at least one agent that inhibits MYC signaling. Exemplary such agents are set forth in Table 4.

In one aspect, the R-2HG may be recombinant R-2HG. Recombinant forms of R-2HG are known in the art, for example production of recombinant R-2HG suitable for the instant methods and compositions is disclosed in Losman, J. A. et al. Science 2013, Mar. 29:339(6127) pp 1621-5, the entire disclosure of which is incorporated herein by reference. R-2HG may be administered as modified R-2HG, for example as ester-modified R-2HG. Pharmaceutical dosage forms suitable for administration include oral and parenteral.

Embodiments of the pharmaceutical composition may be formulated for oral or parenteral administration. According to preferred embodiments, the pharmaceutical compositions are formulated for parenteral administration, for examples as injectable suspensions. Generally, pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exits. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils. In some embodiment, the active may be loaded into/onto nano-carriers, including nano-carriers functionalized to target specific tumor or cancer cells.

R-2HG is typically stored in millimolar concentrations of between 100 and 300 mM. The molecular weight of ester-modified R-2HG is 282.31 g/mol. Specific embodiments of the pharmaceutical compositions formulated as injectable suspensions comprise between about 10 and 500, 50 and 400, 100, and 300, 150 and 250, or about 200 µM R-2HG by weight, and may be administered in a dose of about 1-10 mg R-2HG per kg body weight. However, it will be readily apparent to a person of ordinary skill in the art that specific concentrations and doses will vary according to the characteristics and disease status of an individual patient, and as with most pharmaceutical compositions formulated for the treatment of cancer, the concentrations of active will be variable and personalized; yet readily determinable by the ordinary clinician.

According to other embodiments, kits for convenient clinical treatment of a patient suffering from a glioma or leukemia are also provided. In specific embodiments the kit may comprise a first vial comprising R-2HG, and at least one second vial comprising an agent effective for inhibiting MYC signaling. According to specific embodiments a kit is packaged as relevant to a treatment time frame, and comprises more than one sets of first and second vials. According to very specific embodiments, the at least one second vial comprises an agent selected from the group consisting of the agents set forth in Table 4.

The experiments set forth herein demonstrate that contrary to previously widely-embraced beliefs otherwise, R-2HG actually exhibits a broad anti-leukemia function in the vast majority cases of a variety of human leukemia cell lines, as well as in primary leukemia patient samples. Mechanistically, R-2HG directly binds to and inhibits the enzymatic activity of FTO, a major demethylase of $N^6$-methyladenosine ($m^6A$) that is the most abundant internal modification of messenger RNA (mRNA)[23] that results in increased global $m^6A$ modification and down-regulation of MYC signaling. The high abundance of FTO and the hyper-activation of MYC signaling confer R-2HG sensitivity and resistance, respectively, in leukemic cells. Pharmaceutical inhibition (e.g., by JQ1[24]) of MYC signaling sensitizes R-2HG-resistant leukemic cells to R-2HG treatment. R-2HG also exhibits a synergistic or additive effect with standard therapeutic agents on inhibiting leukemic cell viability. Moreover, R-2HG also displays anti-tumor effect on a variety of human brain tumor cell lines.

EXAMPLES

The Examples are set forth to describe and support embodiments of the invention by providing detailed illustration of specific aspects and elucidation of underpinning mechanisms. The scope of the invention should not be construed as limited to the illustrated embodiments and aspects, but is understood to be commensurate with the appended claims.

The following assays and methodologies apply generally to the Experiments set forth below.

Culture of Cell Lines and Treatment with R-2HG.

For leukemia cells, U937, THP1, MV4-11, JURKAT and HEL were obtained from America Type Culture Collection (ATCC) and cultured at 37° C. in RPMI with 10% fetal bovine serum (FBS) (Gemini Bio-Products), 1% Penicillin-Streptomycin (Life Technologies) and 1% HEPES (Life Technology); TF-1 (ATCC) was maintained in RPMI with 10% FBS, 1% Penicillin-Streptomycin, 1% HEPES and 2 ng/ml GM-CSF (PeproTech); K562 (ATCC) was cultured in IMDM with 10% FBS, 1% Penicillin-Streptomycin and 1% HEPES; NOMO-1, ML-2, PL21, ME-1 and NB4 were obtained from DSMZ and kept in RPMI with 10% FBS, 1% Penicillin-Streptomycin and 1% HEPES; SKNO-1 (DSMZ) was maintained in RPMI with 10% FBS, 1% Penicillin-Streptomycin, 1% HEPES and 10 ng/ml GM-CSF; KOPN-1, KOCL69, KOCL48, KOCL50, KOCL45 and KOCL51 were maintained in RPMI with 10% FBS, 1% Penicillin-Streptomycin and 1% HEPES; MA9.3 (MLL-AF9-transformed human CD34+ cord blood cell), MA9.3ITD (MLL-AF9 plus FLT3-ITD), MA9.3RAS (MLL-AF9 plus NRasG12D), MA9.6 (MLL), MA9.6ITD (MLL-AF9 plus FLT3-ITD) and MA9.6RAS (MLL-AF9 plus NRasG12D) were established by the Mulloy group[26]. For the gliablastoma cell lines, including 8MGBA, A172, U87MG, GAMG, T98G, LN229, LN18 and DK-MG, were originally maintained by the Plas group. All of the cells, with exception of DK-MG, were cultured in DMEM with 10% FBS, 1% Penicillin-Streptomycin and 1% HEPES; DK-MG was maintained in RPMI with 10% FBS, 1% Penicillin-Streptomycin and 1% HEPES. All the cells are only used for research study, and not among commonly misidentified cells lines, and confirmed to be *mycoplasma*-free. All the cells were treated with cell membrane-permeable version of R-2-Hydroxyglutarate (R-2HG) (Toronto Research Chemicals) with indicated concentration.

Leukemic Patient and Healthy Control Samples and In Vitro Colony Forming Assays.

All the AML patient samples were obtained at the time of diagnosis or relapse and with informed consent at the University of Chicago Hospital (UCH), City of Hope (COH) or the First Affiliated Hospital of Zhejiang University, and were approved by the institutional review board of the institutes/hospitals. The information about AML patients was exhibited in Table 3. The BM mononuclear cells (MNCs) were isolated with NycoPrep 1.077A (Axis-Shield) and stored at liquid nitrogen until used. The healthy PB and BM MNCs were purchased from AllCells; the healthy CD34+ hematopoietic stem/progenitor cells (HSPCs) and CD34-cells were isolated from cord blood samples, which were purchased from Cincinnati Children's Hospital. For colony forming assay of BM progenitors, 10,000 cells were plated in 24-well plate with 1 mL human methylcellulose complete media (R&D Systems) and the colonies were counted 12 days later.

TABLE 3

The detailed information for AML patients.

| Sample ID | Molecular abnormalities | Cytogenetics |
|---|---|---|
| 22162 | — | t(11; 19) |
| 20507 | — | t(8; 21) |
| 13295 | — | t(9; 11) |
| 9084 | — | t(9; 11) |
| 9003 | — | t(8; 21) |
| A2233 | FLT3 ITD Neg., FLT3 TKD Neg., NPM1 Pos., CEBPA Neg., IDH1 Pos., IDH2 Neg. | Normal |
| A2535 | FLT3 ITD Neg., FLT3 TKD Neg., NPM1 Neg., C-Kit Neg., CEPBA Neg., IDH1 Neg., IDH2 Pos. | 47, XY, +8[20] |
| A2786 | FLT3 ITD Neg., FLT3 TKD Neg., NPM1 Neg., CEPBA Neg., IDH1 Neg., IDH2 Pos. | Normal |
| A2324 | FLT3 ITD Neg., FLT3 TKD Neg., NPM1 Neg., IDH1 Neg., IDH2 Pos. | Normal |
| A2061 | FLT3 ITD Neg., FLT3 TKD Neg., IDH1 Neg., IDH2 Pos. | Normal |
| A1951 | FLT3 ITD Neg., FLT3 TKD Neg., NPM1 Neg., CEPBA Neg., IDH1 Neg., IDH2 Pos., BCR-ABL | Trisomy 8 |
| A2408 | FLT3-ITD Neg., FLT3-TKD Neg., CEBPA Neg., IDH1 Neg., IDH2 Neg., NPM1 Neg., JAK2 Neg. | Del(8) |
| A2418 | FLT3 ITD Neg., FLT3 TKD Neg., NPM1 Neg., C-Kit Neg., CEBPA Neg., IDH1 Neg., IDH2 Neg. | Del (5) |

Cell Proliferation/Viability, Cell Cycle and Cell Apoptosis Assays.

To study the effects of R-2HG, FTO, or IDH1$^{R132H}$ on viability, the cells were seeded into 96-well plates at the concentration of 5,000-10,000 cells/well in triplicates and MTT (G4000, Promega) was used to assess cell proliferation and viability following the manufacturer's instructions. For cell cycle analysis, Propidium iodide (PI) DNA staining was used to assess the cells at G0/G1, S and G2/M phases, while Hoechst 33342 and Pyronin Y were used to determine the cells at G0, G1 and S/G2/M stages. For the PI staining, cells were resuspended in Krishan's reagent (0.05 mg/ml PI, 0.1% trisodium citrate, 0.02 mg/ml ribonuclease A, 0.3% NP-40), incubated at 37° C. for 30 minutes and then applied to the flow cytometer; For Hoechst/Pyronin Y staining, the cells were suspended in cell culture medium, incubated at 37° C. for 45 minutes with existence of 10 ug/mL Hoechst 33342 and further incubated at 37° C. for 15 minutes with existence of Pyronin Y before flow cytometry. Cell apoptosis assay was conducted with FITC Annexin V Apoptosis Detection Kit I (BD Pharmingen) according to the manufacturer's instructions.

"Human-in-Mouse" Xeno-Transplantation Models.

The NOD/LtSz-scid IL2RG-SGM3 (NSGS) mice were used for "human in mouse" xeno-transplanation model. The NSGS mouse was created by the Mulloy group[27]. NOMO-1 and MA9.3ITD cells, exposed to 300 uM R-2HG or PBS for 4 days, were collected, washed twice with PBS and transplanted via tail vein injection into 6- to 8-week-old NSGS recipient mice. For each recipient mouse, 0.2-0.5×10$^6$ human leukemia cells were transplanted. The mice were euthanized by CO2 inhalation if they displayed typical leukemic symptoms, i.e. hunched posture, labored breathing and decreased activity.

Flow Cytometry.

All the samples were analyzed by FACSAria II or LSR-Fortessa cell analyzer (BD Bioscience). Flow cytometry analysis of mouse BM cells were performed as described previous[46] with some modifications. Data were analyzed with FlowJo software. The following antibodies were used for staining cells, Pacific blue labeled-anti-mouse/human CD11b (Mac-1) (BioLegend), APC labeled anti-mouse CD117 (c-kit) (2B8) (eBioscience), PE-conjugated anti-human CD45 (ThermoFisher), FITC-labeled Annexin V (BD Pharmingen), propidium iodide (PI) (BD Pharmingen), Hoechst 33342 (Sigma) and Pyronin Y (Sigma).

Plasmid Construction.

The wild type FTO-CDS and mutant FTO-CDS (coding region sequence) were amplified from pcDNA3.1_FTO and pcDNA3.1_mutFTO (the two plasmids were kindly provided by Dr. Chuan He) by PCR using the following primers: forward 5'-AGAGCTCTAGAACCACCATGGAT-TACAAAGATGAC-3' and reverse 5'-CTAAGAT-TGCGGCCGCCTAGGGTTTTGCTTCCAGAAGC-3', and then subsequently cloned into lentivector-based pMIRNA1 (SBI). The shRNAs against FTO and YTHDF2 were inserted into pLKO.1 vector. The IDH1$^{R132H}$ (provided by the Sasaki group) was inserted into pTRIPZ lentiviral inducible vector.

RNA Extraction, cDNA Synthesis, qPCR and m$^6$A Dot Blot.

RNA was extracted with miRNeasy Mini Kit (QIAGEN) according to the manufacturer's guidelines. For cDNA synthesis, 200 ng RNA was used for reverse transcription in 10 ul reaction volume with Qiagen's RT kit following the manufacturer's instructions. Then qPCR was performed with 2×SYBR green qPCR Master Mix (Thermo Fisher) in the AB 7900HT Fast Real-Time PCR system (Applied Biosystem). GAPDH or ACTIN was used as endogenous control and each reaction was run in triplicate. The m$^6$A dot blot was conducted as previously described with some modifications[47]. RNA samples were denatured at 65° C. for 5 minutes with existence of 3 volume of RNA incubation buffer, added equal volume of chilled 20×SSC buffer (Sigma-Aldrich), and spotted on the Amersham Hybond-N+ membrane (GE Healthcare) with a Bio-Dot Apparatus (Bio-Rad). After UV crosslinking, the membrane was washed with 1×PBST buffer (Thermo Scientific), blocked with 5% non-fat milk and incubated with anti-m$^6$A antibody (Synaptic Systems) overnight at 4° C. Then the HRP-conjugated goat anti-rabbit IgG (Santa Cruz Biotechnology) was added to the blots for 1 hour at room temperature and the membrane was developed with Amersham ECL Prime Western Blotting Detection Reagent (GE Healthcare). The relative signal density of each dot was quantified by Gel-Pro analyzer software.

DNA Extraction and 5hmC Dot Blot.

DNA was isolated with DNeasy Blood & Tissue Kit (Qiagen) according to the manufacturer's instructions. To assess 5hmC levels, dot blot was performed as follows: DNA samples were added into 0.1N NaOH, denatured at 99° C. for 5 minutes, neutralized by adding 0.1 volume of 6.6M ammonium acetate, and spotted on Amersham Hybond-N+. After UV crosslinking, the membrane was staining with 0.02% methylene blue (Sigma-Aldrich), washed with 1×PBST buffer, blocked with 5% non-fat milk and incubated with 5hmC antibody (Active Motif) overnight at 4° C. Then the HRP-conjugated goat anti-rabbit IgG (Santa Cruz Biotechnology) was added to the blots for 1 hour at room temperature and the membrane was developed with Amersham ECL Prime Western Blotting Detection Reagent (GE Healthcare). The relative signal density of each dot was quantified by Gel-Pro analyzer software.

Protein Extraction and Western Blotting.

For western blotting, cells were placed on iced, washed twice with ice-cold PBS. Proteins were extracted with RIPA buffer (Sigma-Aldrich) with protease inhibitor cocktail and phosphatase inhibitor cocktail (Thermo Fisher). The protein concentration was determined with BCA protein assay kit (Thermo Scientific). An estimated 30-60 ug protein was loaded per well on 10% SDS-PAGE gel and transferred onto PVDF membrane (Fisher Scientific), activated by methanol. Membranes were washed with 1×PBST, blocked with 5% milk and incubated with antibodies against FTO (ab124892, Abcam), ALKBH5 (ab174124, Abcam), GAPDH (sc-47724, Santa Cruz), β-Actin (3700S, Cell Signaling), MYC (sc-764, Santa Cruz), Flag (F1804, Sigma Aldrich), H3K9me3 (ab8898, Abcam) and H3K36me3 (ab9050, Abcam). Secondary antibodies and detection were according to routine laboratory practices.

Drug Affinity Responsive Targets Stability (DARTS).

To identify the potential target of R-2HG, DARTS was conducted following the published protocol[48]. 50×10$^6$ cells were lysed in M-PER (78501, Thermo Fisher Scientific) with protease inhibitor cocktail and phosphatase inhibitor cocktail. TNC buffer (50 mM Tris-HCL pH8.0, 50 mM NaCl and 10 mM CaCl$_2$) was added into the lysate and the protein concentration was determined by BCA assay. Cell lysates were incubated with varying concentration of R-2HG or PBS (vehicle) for 1 hour at room temperature and digested with Pronase (1:300 for ALKBH5; 1:1000 for FTO) (10165921001, Roche) for 30 minutes at room temperature. The digestion was stopped by protease inhibitor cocktail and the samples were immediately placed on ice. For R-2HG target identification, western blot was performed. GAPDH was used as a negative control.

Lentivirus Preparation, Precipitation and Infection.

Lentivirus particles for pMIRNA1-FTO, pMIRNA1-FTO-Mut, pMIRNA1, pLKO.1-shFTO, pLKO.1-shYTHDF2 and pLKO.1 were packaged with pMD2.G, pMDLg/pRRE and pRSV-Rev (Addgene). Briefly, 0.5 µg pMD2.G, 0.3 µgpMDLg/pRRE, 0.7 µg pRSV-Rev and 1.5 µg construct for overexpression or knockdown of specific genes were co-transfected into HEK-293T cells in 60 mm cell culture dish with Effectene Transfection Reagent (301427, QIAGEN). The pTRIPZ-IDH1$^{R1321-1}$ was packaged with psPAX2 and pMG2.G. The lentivirus particles were harvested at 48 and 72 hours and concentrated with PEG-it virus precipitation solution (LV810A-1, SBI). For infection, the lentivirus were directly added into with cells with existence of 8 ug/ml polybrene (H9268, Sigma-Aldrich) and then spinoculation was conducted at 32° C., 1000 rmp for 90 min. The positive infected cells were selected with GFP expression (for FTO and FTO-Mut) or 1 ug/ml puromycin (for shFTO, shYTHDF2 and IDH1$^{R1321-1}$) (P8833, Sigma-Aldrich). After selection, 1 ug/ml Doxycycline (D9891, Sigma-Aldrich) was added to to induce expression of IDH1$^{R132H}$.

RNA-Seq and Relative Data Analysis.

RNA from R-2HG sensitive, resistant and healthy controls cell lines were extracted by mirVana miRNA Isolation Kit (Thermo Fisher, Grand Island, N.Y.) with total RNA extraction protocol. NEBNext Poly(A) mRNA Magnetic Isolation Module (New England BioLabs, Ipswich, Mass.) was used for polyA RNA purification. Library was prepared by PrepX mRNA Library kit (WaferGen) combined Apollo 324 NGS automated library prep system. Libraries at the final concentration of 15 pM were clustered onto a single read (SR) flow cell using Illumina TruSeq SR Cluster kit v3, and sequenced to 50 bp using TruSeq SBS kit on Illumina HiSeq system. Differential gene expression was analyzed by standard Illumina sequence analysis pipeline. The data have been deposited in the GEO repository with the accession number GSE87187.

RNA samples from R-2HG- or PBS-treated sensitive leukemia cells were also extracted, purified as described above, library was prepared by or NEBNext Ultra Directional RNA Library Prep Kit (New England BioLabs, Ipswich, Mass.). The libraries were sequenced and analyzed following the same protocol as above. The data have been deposited in the GEO repository with the accession number GSE87189.

Gene Set Enrichment Analysis (GSEA)[28] was used to analyze the signal pathway enrichment in different groups of samples. "H: hallmark gene sets" and "C2: curated gene sets" obtained from The Molecular Signatures Database (MsigDB)[28] were used as the "gene sets database" input.

m$^6$A-Seq Assays and Data Analysis.

The m$^6$A-seq procedure was performed as published protocol[36]. Total RNA was isolated with TRIZOL (15596-018, Life technology). Polyadenylated RNA was extracted using FastTrack MAG Maxi mRNA isolation kit (Life technology). RNA fragmentation Reagents (Ambion) was used to randomly fragment RNA. m$^6$A antibody (Synaptic Systems) was applied for m$^6$A pull down (i.e., m$^6$A IP). Both input and m$^6$A IP samples were prepared for next-generation sequencing (NGS). The library preparation was constructed by TruSeq Stranded mRNA Sample Prep Kit (Illumina) and was quantified by BioAnalyzer High Sensitivity DNA chip, and then was deeply sequenced on the Illumina HiSeq 2500. The data have been deposited in the GEO repository with the accession number GSE87190.

For the data analysis, the following pipeline was used to identify m$^6$A peaks. The reads from input and m6A IP samples were aligned to GRCh38 reference genome using Tophat[49]. Both MACS2[50] callpeak function with parameter extsize 85 and exomePeak[51] with default settings were used to call m$^6$A peaks based on the .bam files generated by Tophat. To achieve high specificity, only the m$^6$A peaks called by both MACS2 and exomePeak were retained for the further analysis. The m$^6$A peaks were annotated using an ad hoc perl script. Sequence motifs enriched in m$^6$A peak regions compared to control regions were identified using HOMER[52]. The differentially methylated m$^6$A peaks were also identified by MACS2 bdgdiff function and exomePeak, the peaks called by both MACS2 and exomePeak were retained. Circos[53] and Integrative Genomics Viewer (IGV)[54] were used to visualize the distributions of the m6A peaks. The RNA-seq reads were normalized using Cufflinks[55]. Cuffdiff[56] was used to calculate differentially expressed genes.

Gene-Specific m$^6$A qPCR.

To assess the relative abundance of specific mRNA in m$^6$A IP and input groups, qPCR was performed. The m$^6$A RNA immunoprecipitation (MeRIP) was performed with Magna MeRIP m$^6$A kit (17-10499, Millipore) according to the manufacturer's instructions. Reverse transcription and qPCR were performed with Qiagen's RT kit and 2×SYBR green qPCR Master Mix. Cycle threshold ($C_t$) values were used to determine the relative enrichment of mRNA.

RNA Stability Assay.

The actinomycin D (A9415, Sigma-Aldrich) was added into leukemia cells at 5 ug/ml to assess RNA stability. After 0, 2, 3, 4 or h hours of incubation, the cells were collected, RNA samples were extracted for reverse transcription and qPCR. The mRNA degradation rate was estimated according to the published paper[57]. With actinomycin D, the mRNA transcription was closed and the degradation rate of RNA ($K_{decay}$) was estimated by following equation:

$$ln(C/C_0) = -K_{decay}t$$

$C_0$ is the concentration of mRNA at time 0 hour. And t is the transcription inhibition time, C is the mRNA concentration at the time t. Thus the $K_{decay}$ can be derived by the exponential decay fitting of $C/C_0$ versus time t. The half-time ($t_{1/2}$), which means $C/C_0=50\%/100\%=\frac{1}{2}$, can be calculated by the following equation:

$$ln(\frac{1}{2}) = -K_{decay}t_{1/2}$$

Rearrangement of the above equation leads to the mRNA half-life time value, $t_{1/2} = ln2/K_{decay}$.

Dual-Luciferase Reporter and Mutagenesis Assays.

To determine whether FTO-induced expression of MYC is dependent on m$^6$A modification, we performed dual-luciferase reporter and mutagenesis assays with pMIR-REPORT-MYC-CDS-WT (wild type CDS of MYC), pMIR-REPORT-MYC-CDS-Mut (mutant CDS of MYC, m$^6$A was replaced by T in the m$^6$A motifs), pGL3-Basic-MYC-5'UTR-WT (wild type 5'UTR of MYC) and pL3-Basic-MYC-5'UTR-Mut (mutant 5'UTR of MYC, m$^6$A was replaced by T in the m6A motifs). All the plasmids were transfected into HEK-293T cells with pRL-TK (control reporter vector) and pMIRNA1-FTO, or pMIRNA1-FTO-Mut or pMIRNA1. The relative luciferase activities were assessed with Dual-luciferase reporter assay system (E1910, Promega) at 48 hours. Each group was repeated in triplicate.

Example 1

R-2HG Shows a Broad Anti-Leukemic Activity

To define the pathological effect of R-2HG in leukemia in general, 27 leukemia cell lines (Table 1) were exposed to a series of concentrations (i.e., 20, 100 and 300 µM) of cell membrane-permeable ester-modified R-2HG (as set forth structurally herein).

Figure 1D:
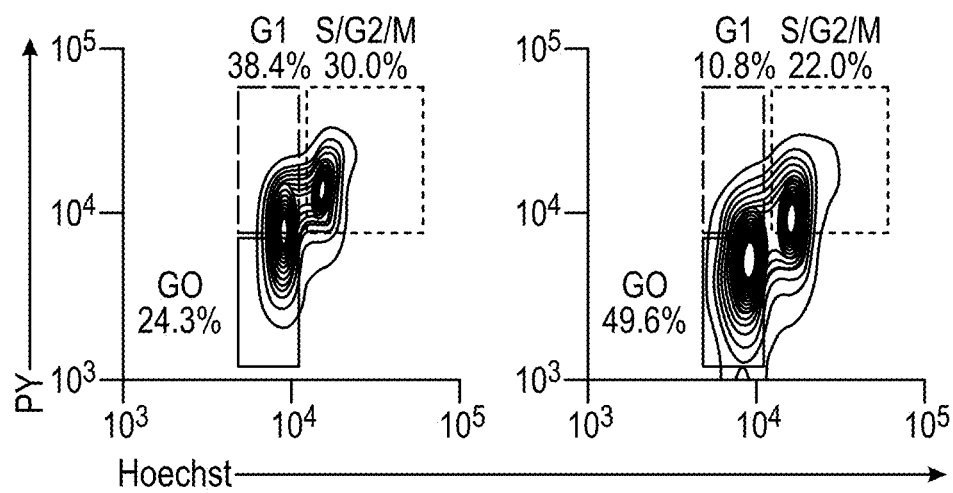
Figure 1E:
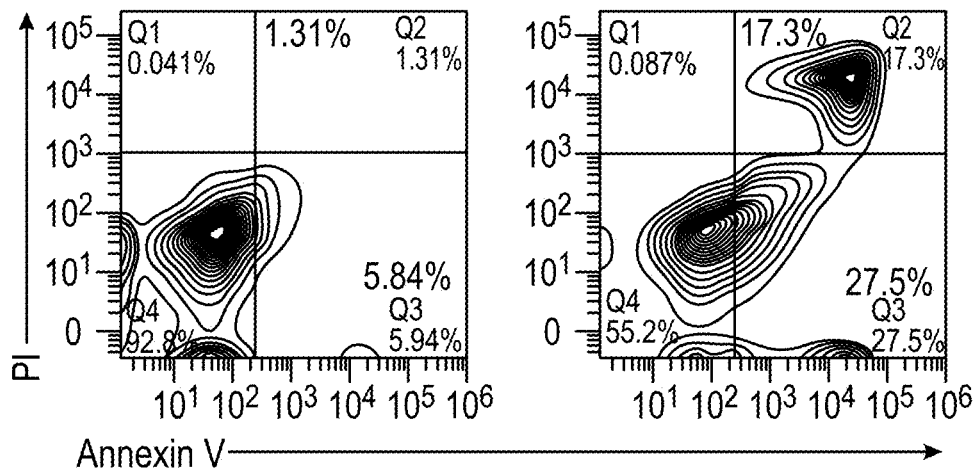
Figure 1F:
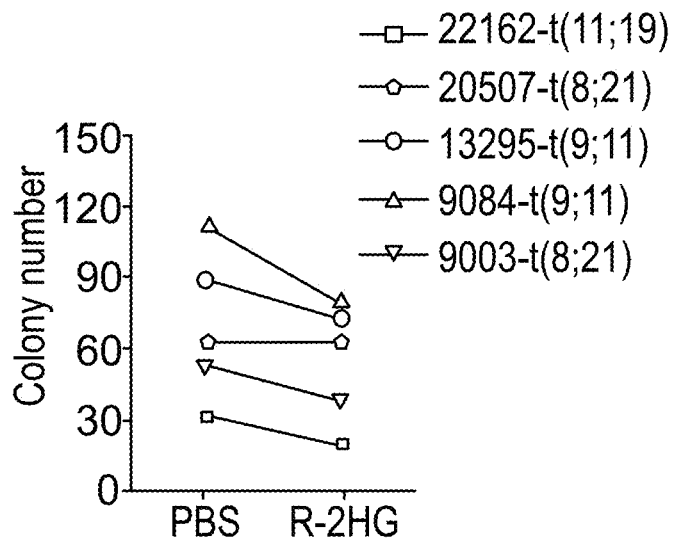
Figure 1G:
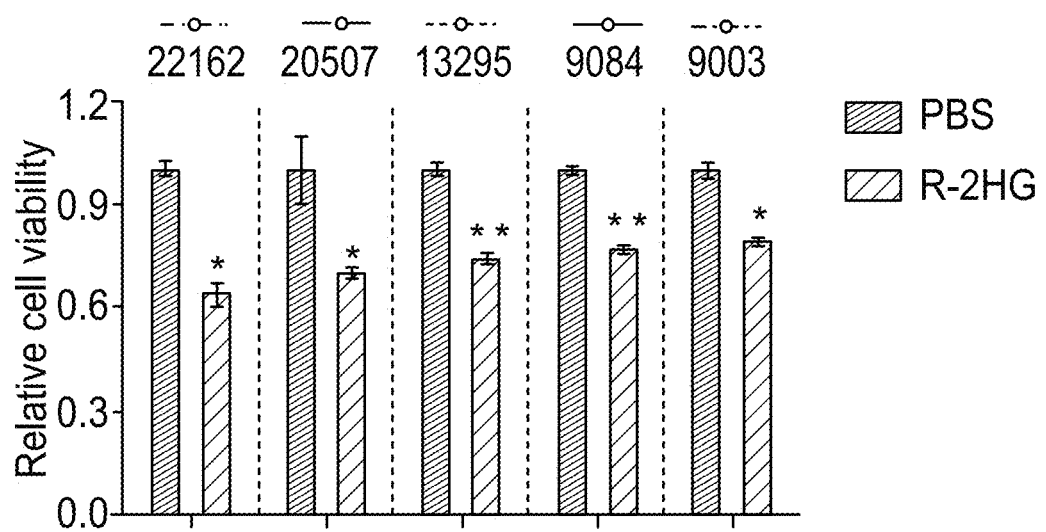
Figure 6A:
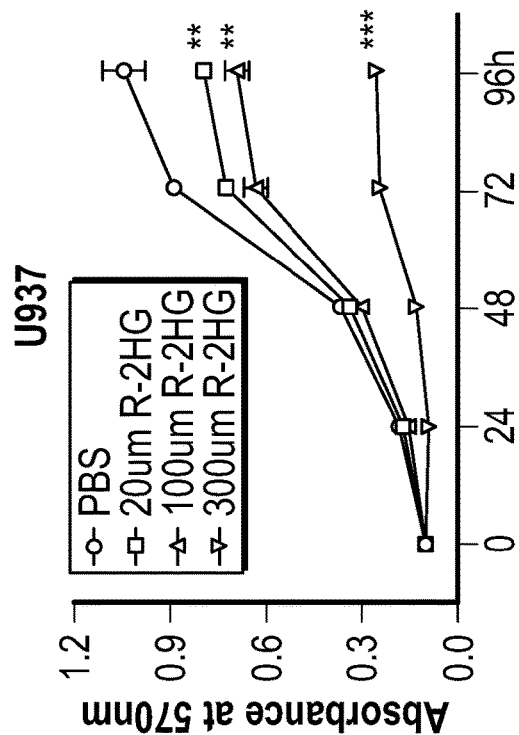
FIGS. 6A-6AA demonstrates the effects of R-2HG on the proliferation/growth of leukemic cells. Individual 27 leukemic cell lines were seeded in 96-well plate at 10,000 cells/well, under the treatment with 20 uM, 100 uM, or 300 uM cell-permeable R-2HG, or with vehicle control (PBS), with FIG. 6A) depicting NOMO-1, FIG. 6B) U937, FIG. 6C) MA9.3ITD, FIG. 6D) ML-2, FIG. 6E) MONOMAC-6, FIG. 6F) MA9.3, FIG. 6G) THP1, FIG. 6H) MA9.6, FIG. 6I) PL21, FIG. 6J) MA9.6ITD, FIG. 6K) KOPN-1, FIG. 6L) SKNO-1, FIG. 6M) MA9.6RAS, FIG. 6N) MV4-11, FIG. 6O) ME-1, FIG. 6P) KASUMI-1, FIG. 6Q) KOCL69, FIG. 6R) JURKAT, FIG. 6S) KOCL481, FIG. 6T) KOCL50, FIG. 6U) KOCL45, FIG. 6V) MA9.3RAS, FIG. 6W) TF-1, FIG. 6X) HEL, FIG. 6Y KOCL51, FIG. 6Z) K562, and FIG. 6AA) NB4. The cell proliferation was detected by MTT assay via recording absorbance at 570 nm at indicated time points (i.e., 0, 24, 48, 72 and 96 hours post seeding). Detailed information about the 27 leukemia cell lines, including fusion genes, karyotype and FAB subtypes, is set forth in Table 1. *, P<0.05; , P<0.01; *, P<0.001; t-test.
Figure 6B:
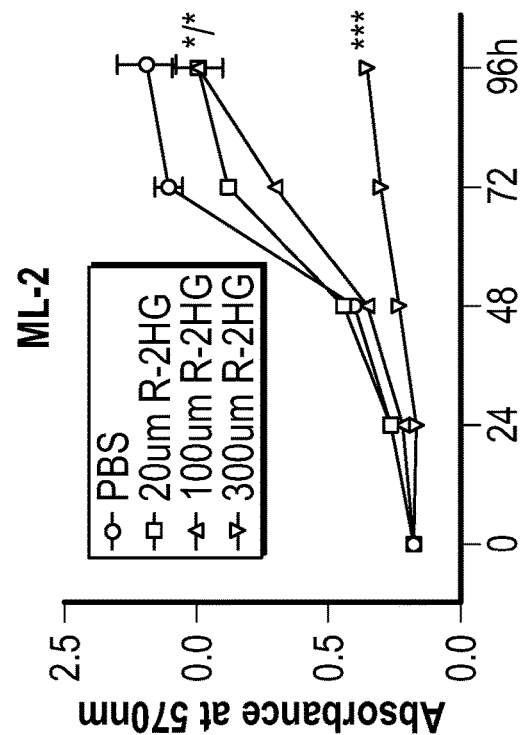
Figure 6C:
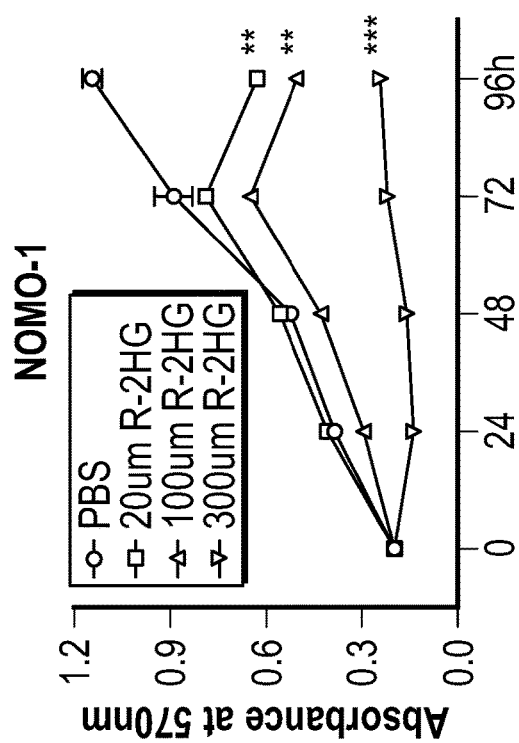
Figure 6D:
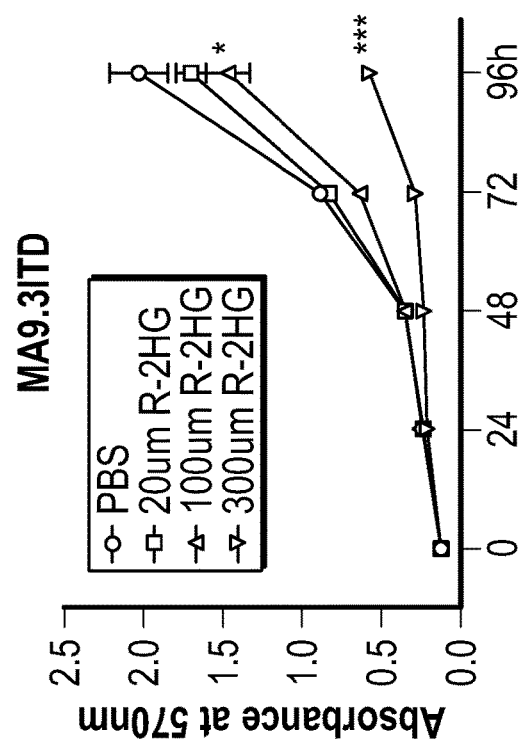
Figure 6F:
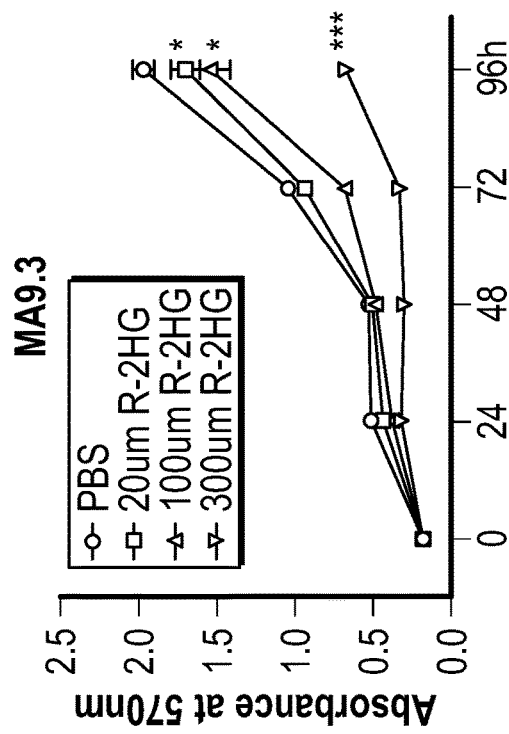
Figure 6H:
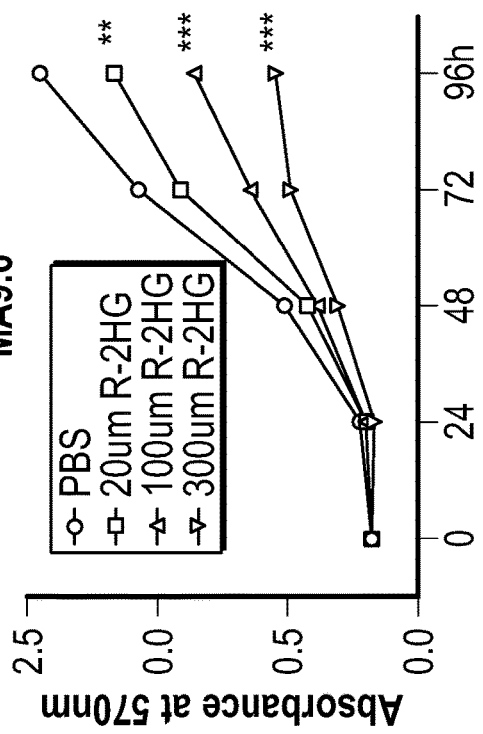
Figure 6E:
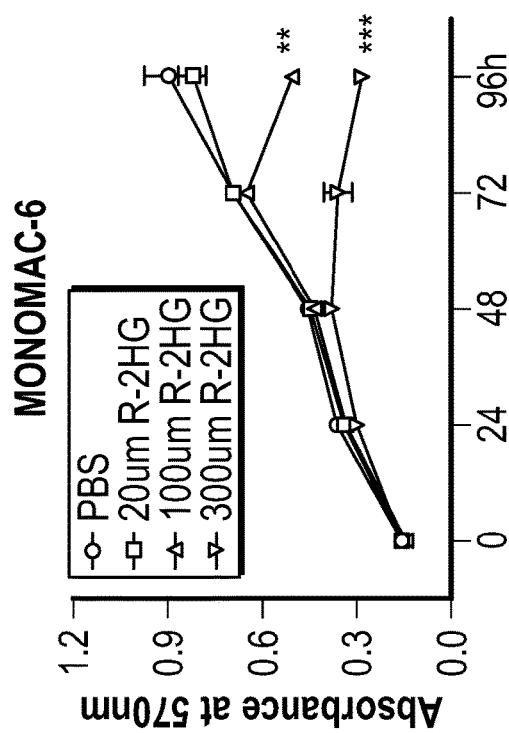
Figure 6G:
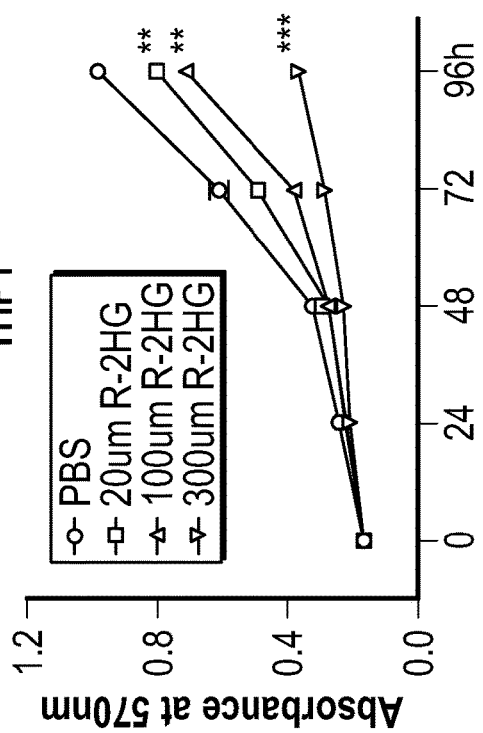
Figure 6I:
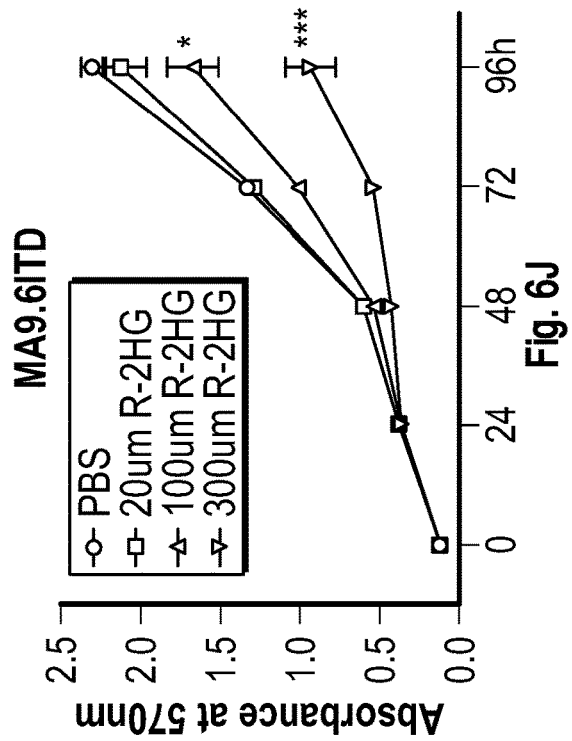
Figure 6J:
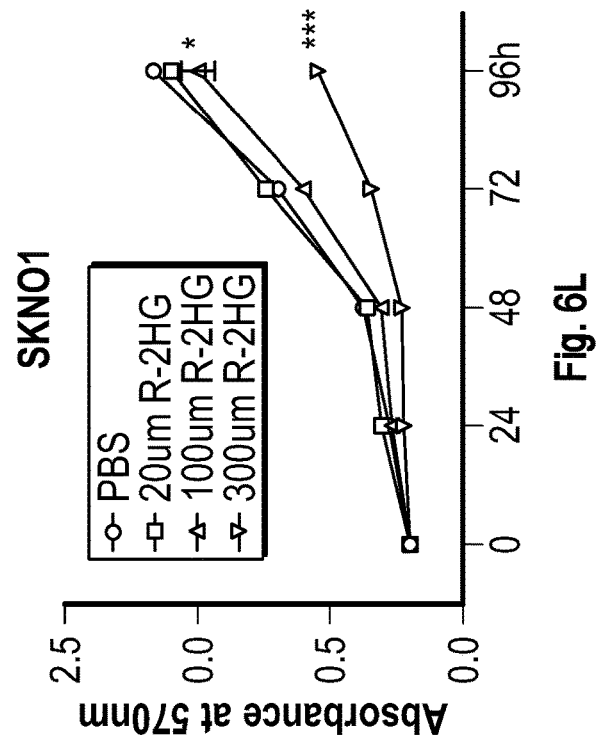
Figure 6K:
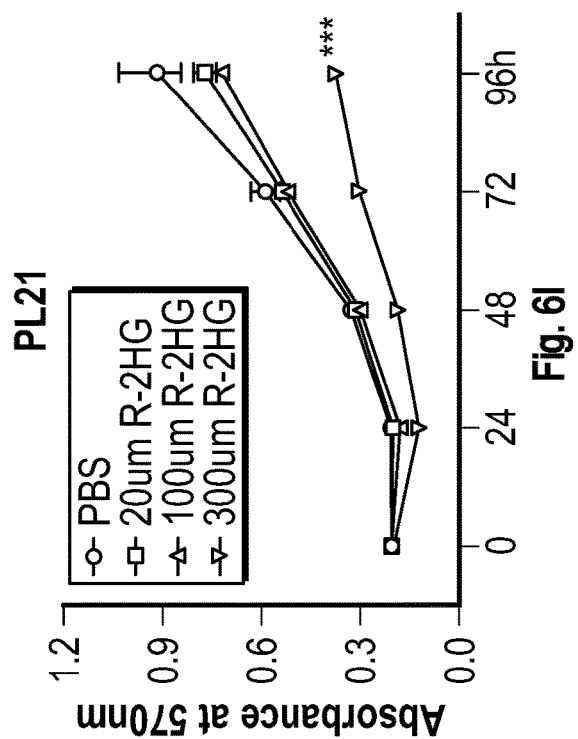
Figure 6L:
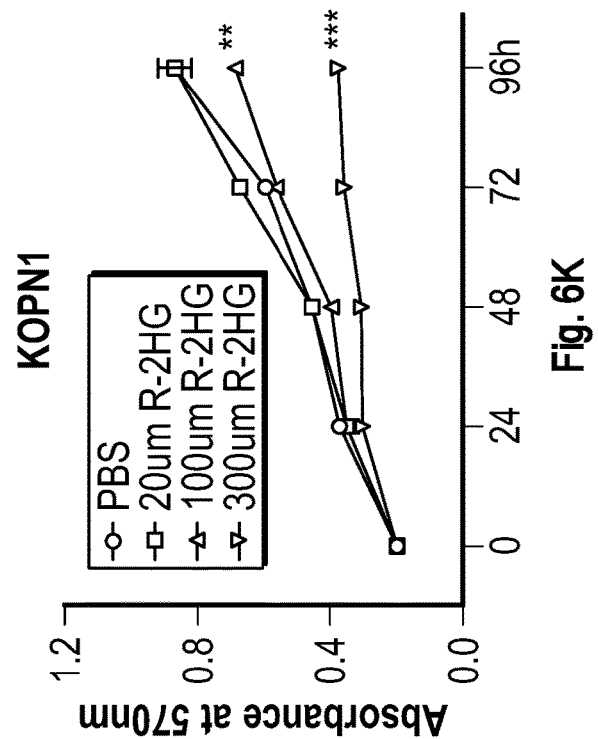
Figure 6Q:
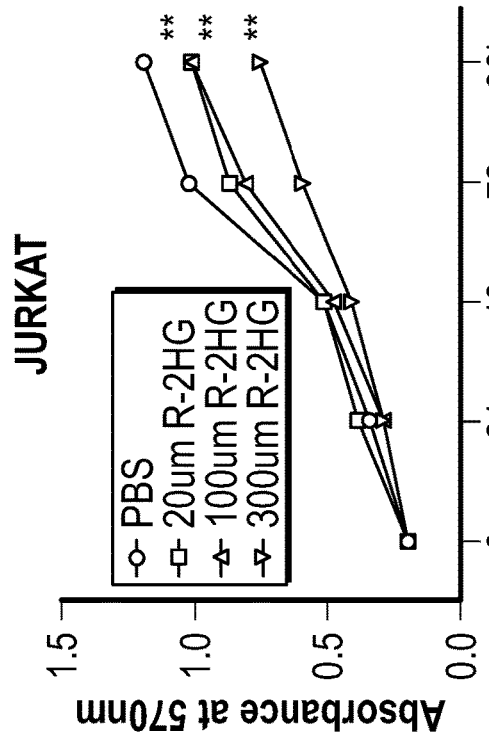
Figure 6R:
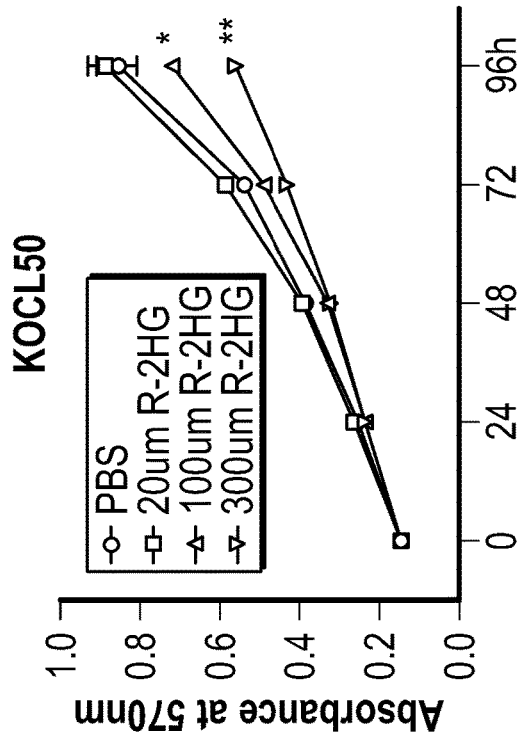
Figure 6S:
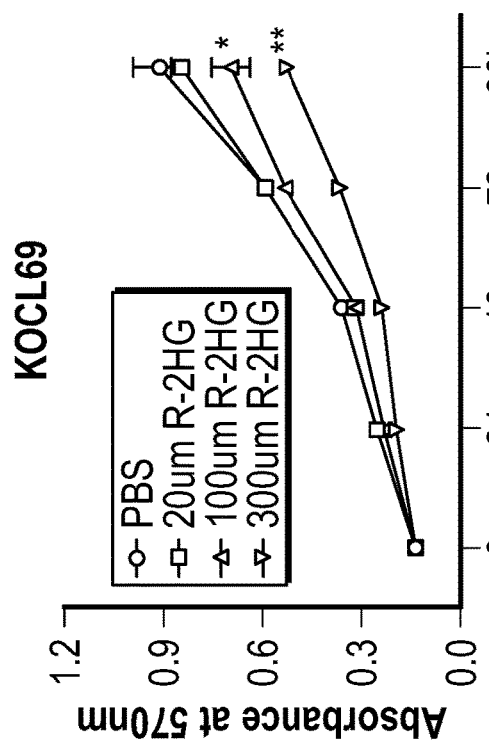
Figure 6T:
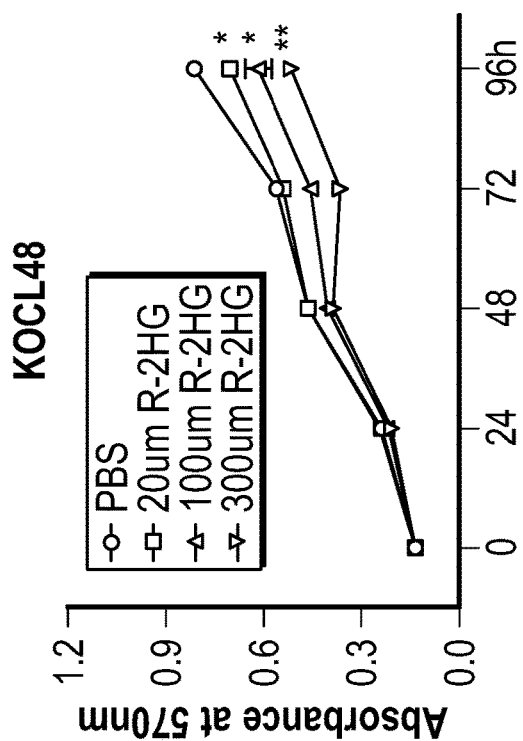
Figure 6U:
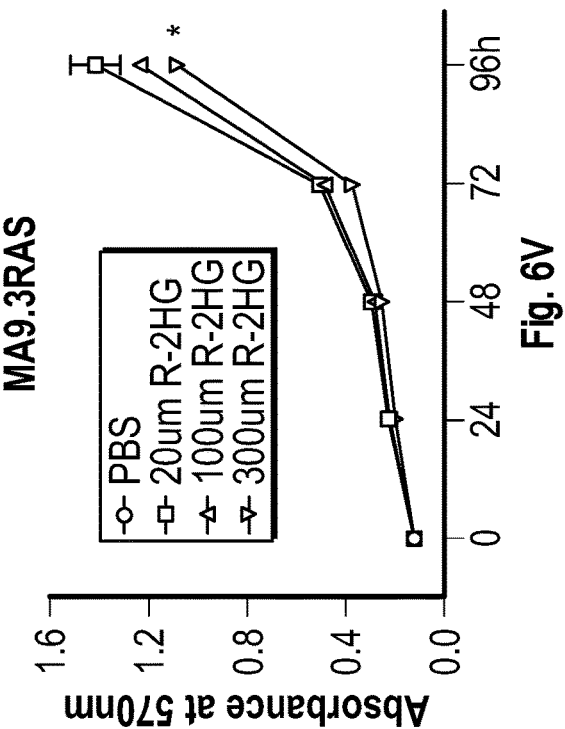
Figure 6V:
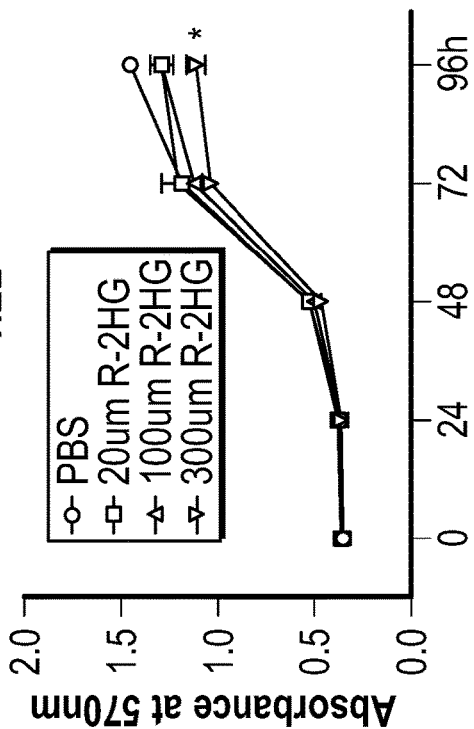
Figure 6W:
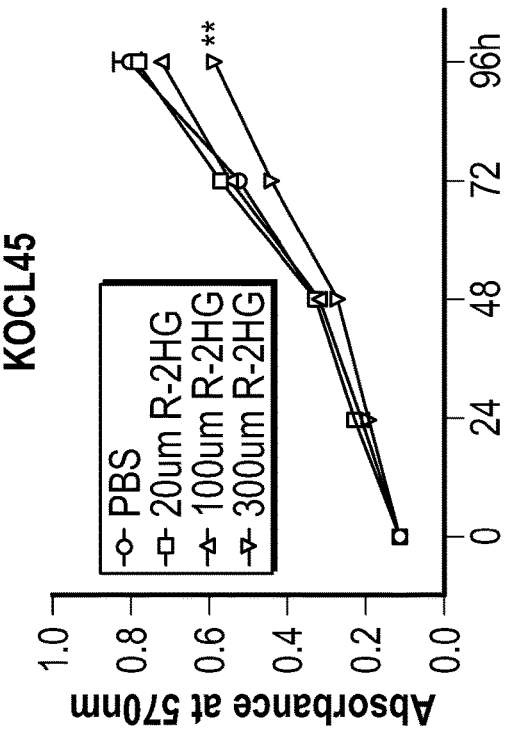
Figure 6X:
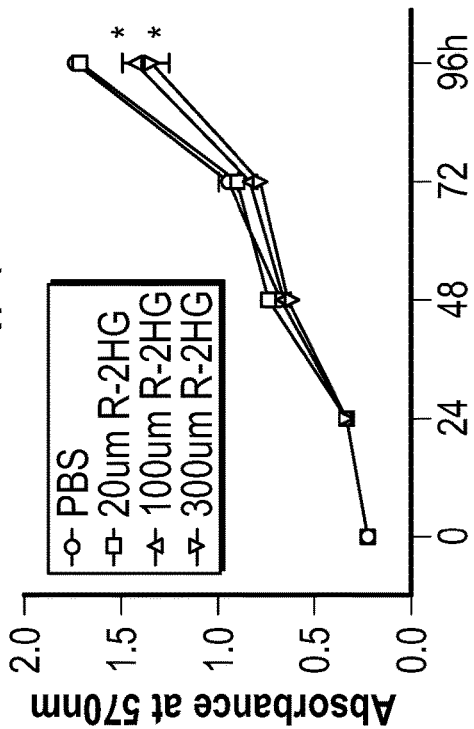
Figure 8A:
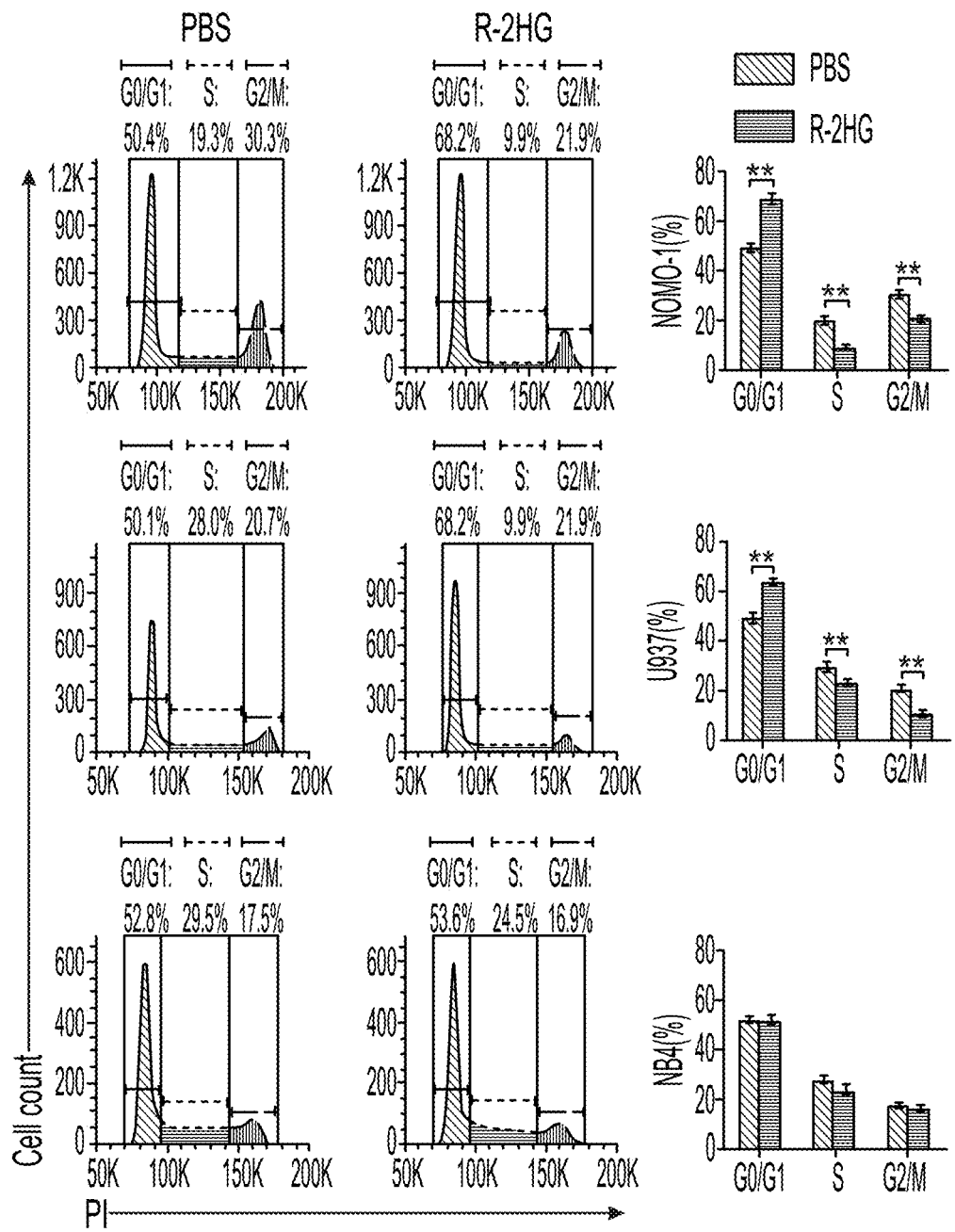
FIG. 8A-FIG. 8C demonstrate the effects of R-2HG on cell cycle and apoptosis.
Figure 8B:
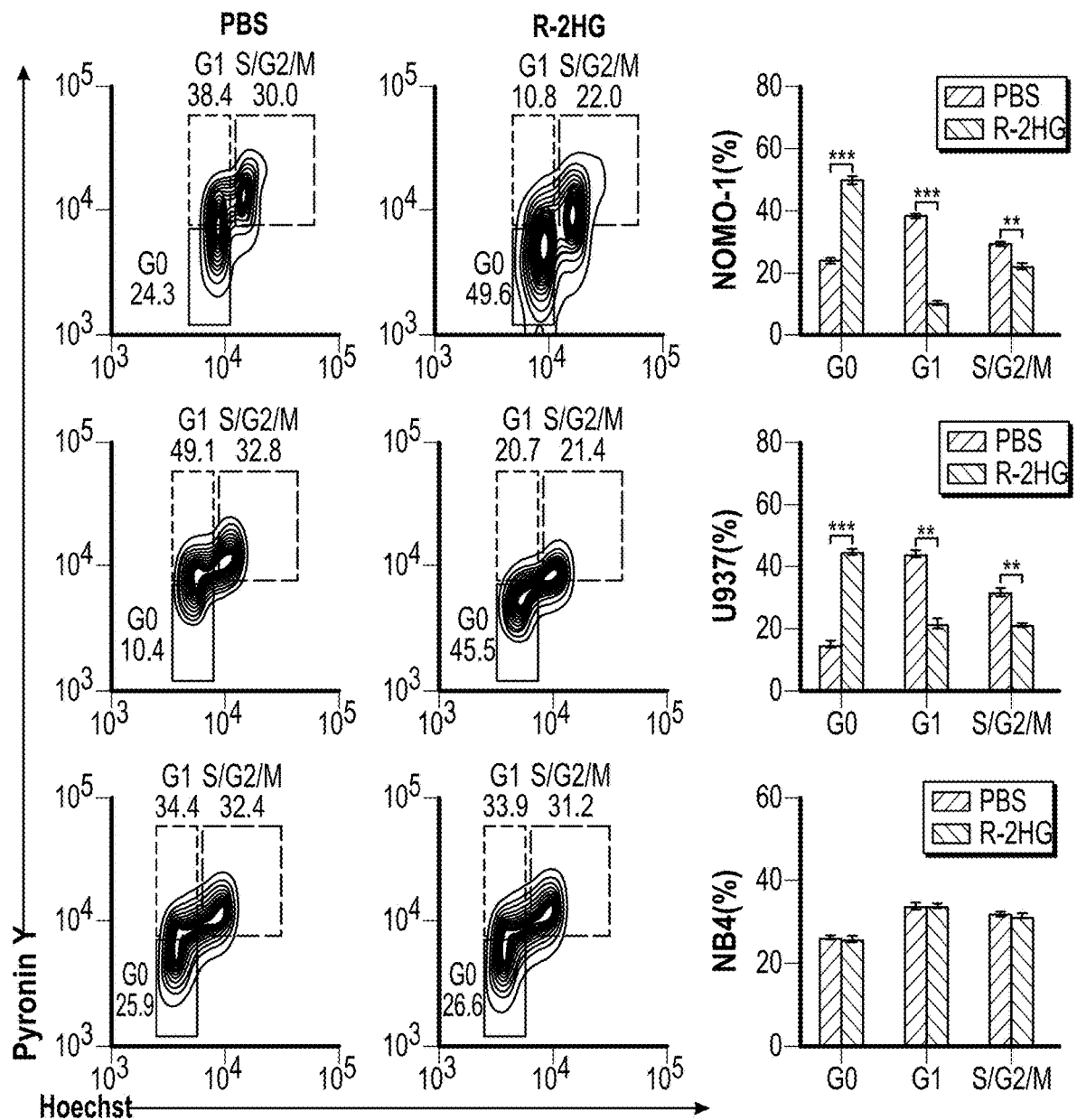
Figure 8C:
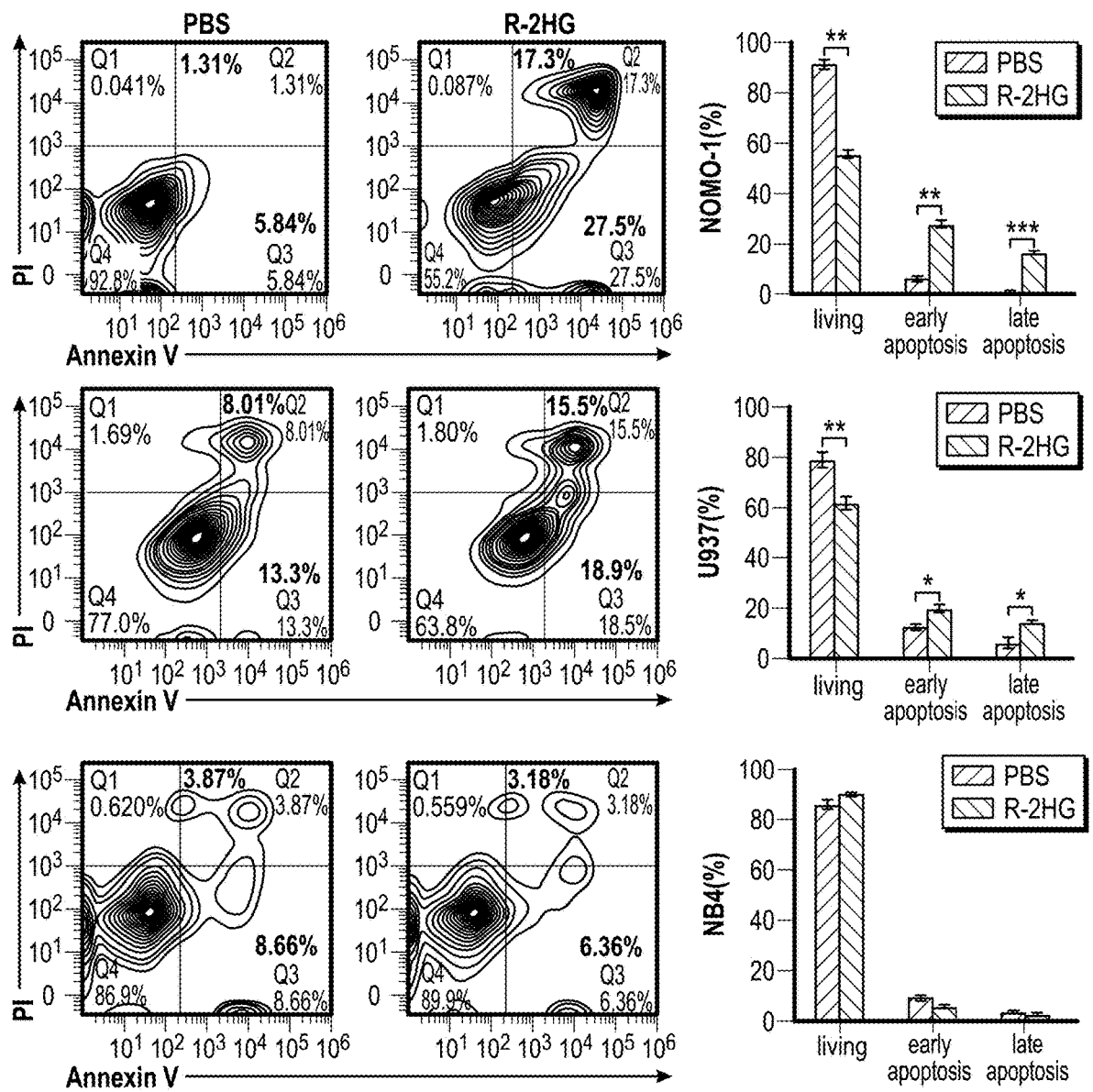
Figure 9A:
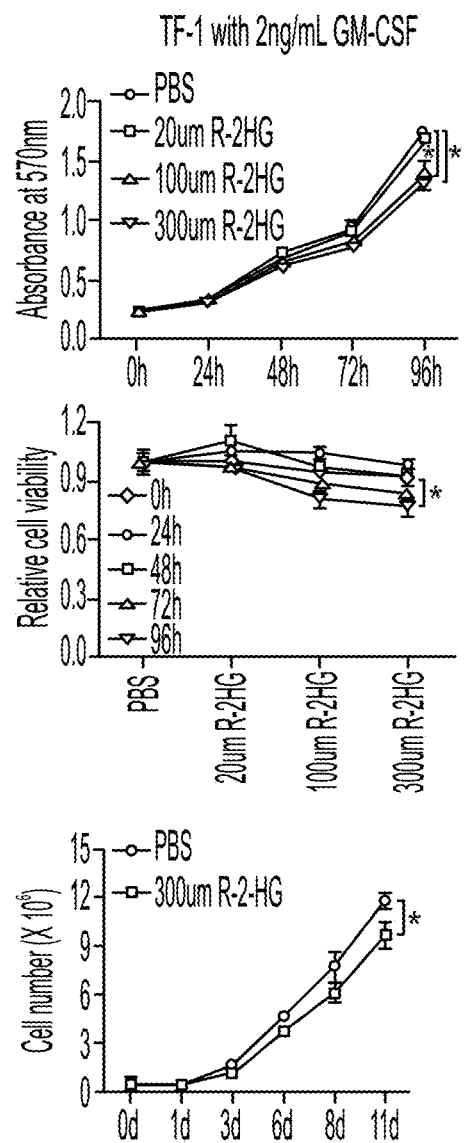
Figure 9B:
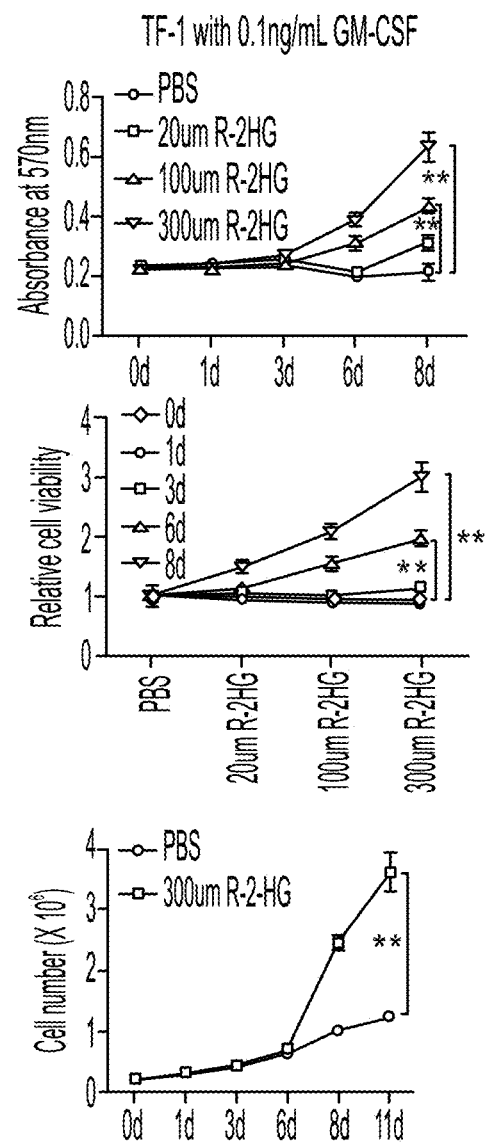

Very strikingly, R-2HG inhibited cell growth/proliferation and viability in a time- and dose-dependent manner in the vast majority of the leukemia cell lines, though with variable inhibitory degrees; no promoting effect on cell growth/viability was observed (FIG. 1A and FIG. 1B; FIG. 6A-6AA, FIG. 7A-7AA). The inhibition of cell proliferation/viability is likely related to R-2HG-induced cell-cycle arrest and apoptosis (FIGS. 1C-1E; FIGS. 8A-8C). Since it was previously reported that R-2HG promoted cell proliferation and induced leukemic transformation in TF-1 cells under a GM-CSF poor condition[13], it was considered important to attempt to replicate the experiments. Consistent with the previous report[13], the data show that R-2HG slightly decreased cell growth/viability in normal condition (2 ng/ml of GM-CSF), while significantly increasing cell proliferation in cytokine-poor condition (0.1 ng/ml of GM-CSF) (FIGS. 9A and 9B). Nonetheless, in SKNO-1, another GM-CSF-dependent leukemia cell line[25], R-2HG notably inhibited cell proliferation and viability at cytokine-normal and -poor conditions (FIGS. 9C and 9D), suggesting that the proliferation-promotion effect of R-HG observed in TF-1 cells is unique and not simply due to a low concentration of GM-CSF. Moreover, it was shown that R-2HG also decreased colony-forming activity (FIG. 1F) and cell viability (FIG. 1G) of human primary AML cells.

TABLE 1

The selected 27 leukemia cell lines for detecting R-2HG response.

| Cell line name | Diagnosis | Karyotype |
|---|---|---|
| HEL | AML-M6 | Normal |
| JURKAT | ATL | Normal |
| K562 | CML | t(9; 22) |
| KASUMI-1 | AML-M2 | t(8; 21) |
| KOCL-45 | ALL-L1 | t(4; 11) |
| KOCL-48 | AML-M4 | t(4; 11) |
| KOCL-50 | ALL-L1 | t(11; 19) |
| KOCL-51 | ALL-L1 | del(11)(q23) |
| KOCL-69 | ALL-L1 | t(4; 11) |
| KOPN-1 | ALL-L1 | t(11; 19) |
| MA9.3 | AML | Normal |
| MA9.3ITD | AML | Normal |
| MA9.3RAS | AML | Normal |
| MA9.6 | AML | Normal |
| MA9.6 RAS | AML | Normal |
| MA9.6ITD | AML | Normal |
| ME-1 | AML-M4 | inv(16) |
| ML-2 | AML-M4 | t(6; 11) |
| MONOMAC 6 | AML-M5 | t(9; 11) |
| MV4-11 | AML-M5 | t(4; 11) |
| NB4 | AML-M3 | t(15; 17) |
| NOMO-1 | AML-M5 | t(9; 11) |
| PL-21 | AML-M3 | t(15; 17) |
| SKNO-1 | AML-M2 | t(8; 21) |
| TF-1 | AML-M6 | Normal |
| THP-1 | AML-M5 | t(9; 11) |
| U937 | AML-M5 | t(10; 11) |

Note:
AML, acute myeloid leukemia;
CML, chronic myeloid leukemia;
ALL, acute lymphoid leukemia;
ATL, adult T-cell leukemia.
MA9.3 and MA9.6 are derived from CD34+ HSPCs transformed with MLL-AF9 fusion gene;
MA9.3ITD and MA9.6ITD are transformed with while MLL-AF9 plus FLT3-ITD;
MA9.3RAS and MA9.6RAS are transformed with MLL-AF9 plus NRasG12D.

Figure 1H:
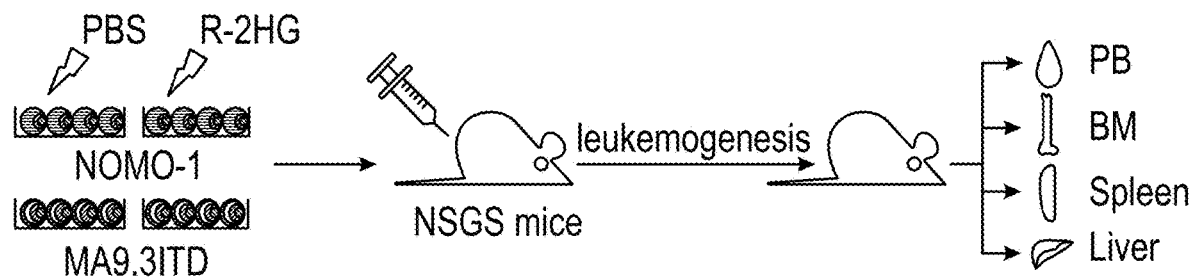
Figure 1I:
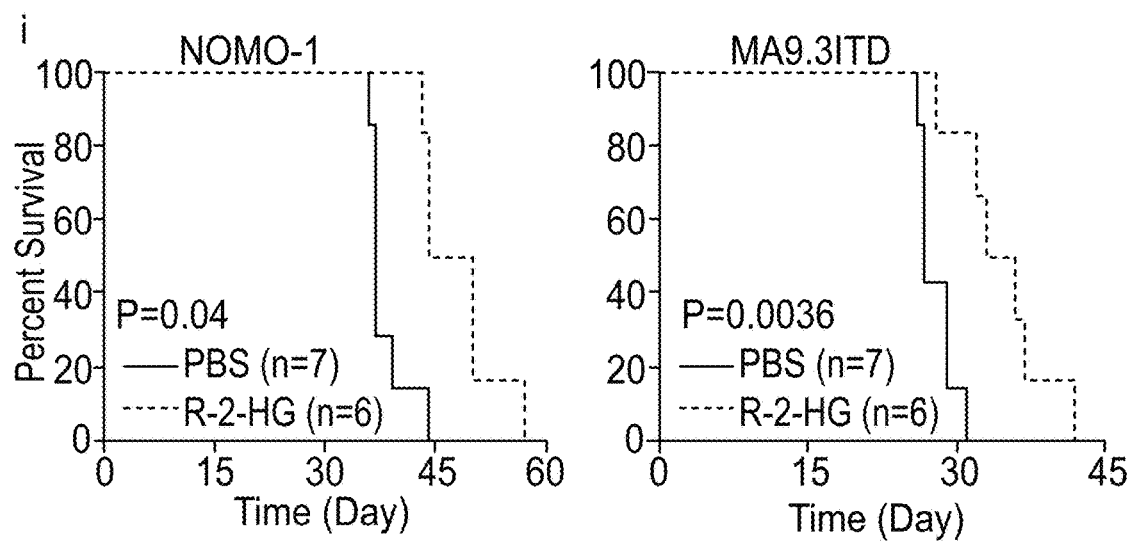
Figure 1J:
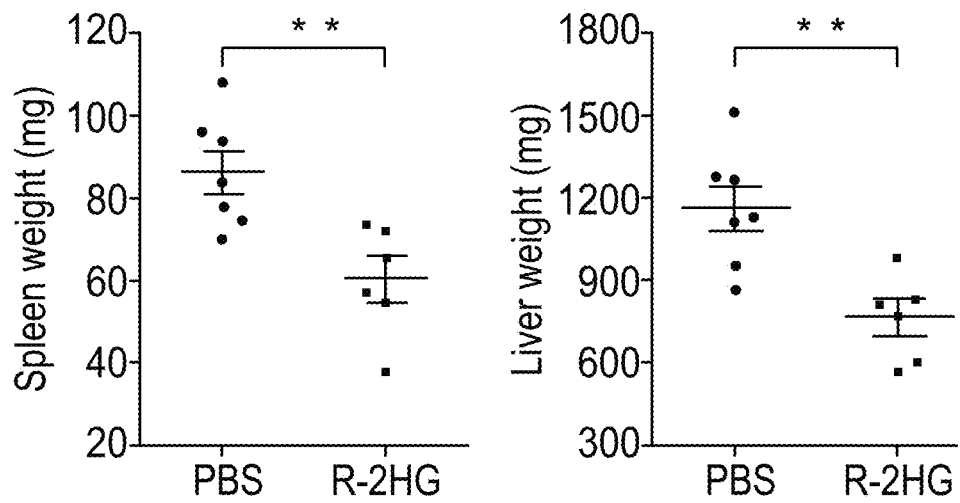
Figure 1K:
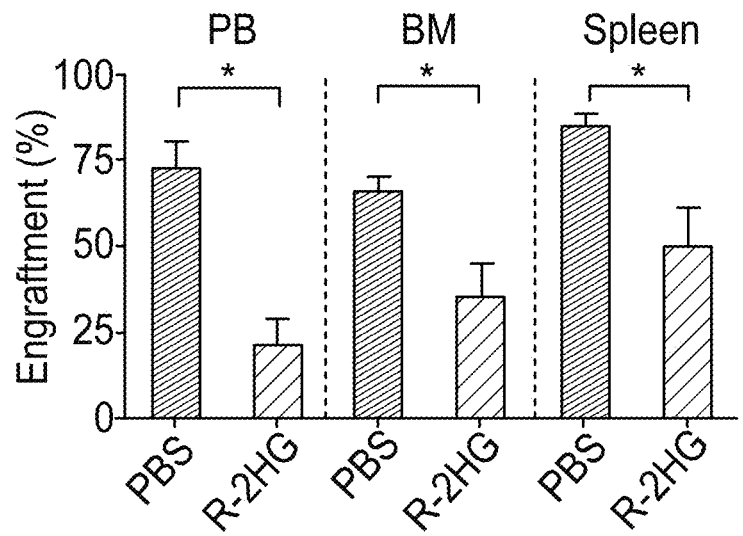
Figure 10A:
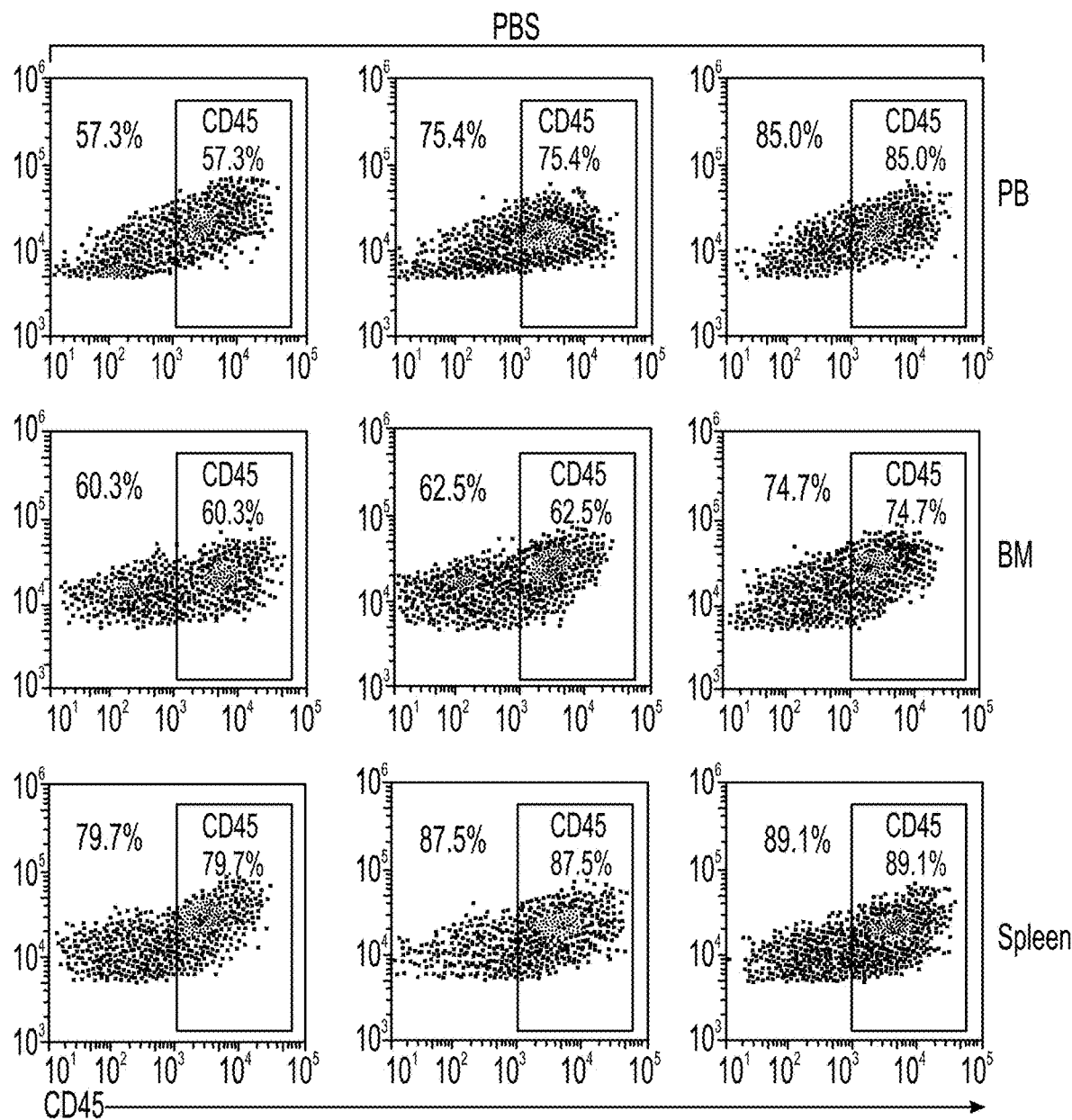
FIG. 10A-FIG. 10D set forth the effects of R-2HG on the engraftment and leukemic blast cell proportion of R-2HG-sensitive leukemic cells in NSGS recipient mice.
Figure 10B:
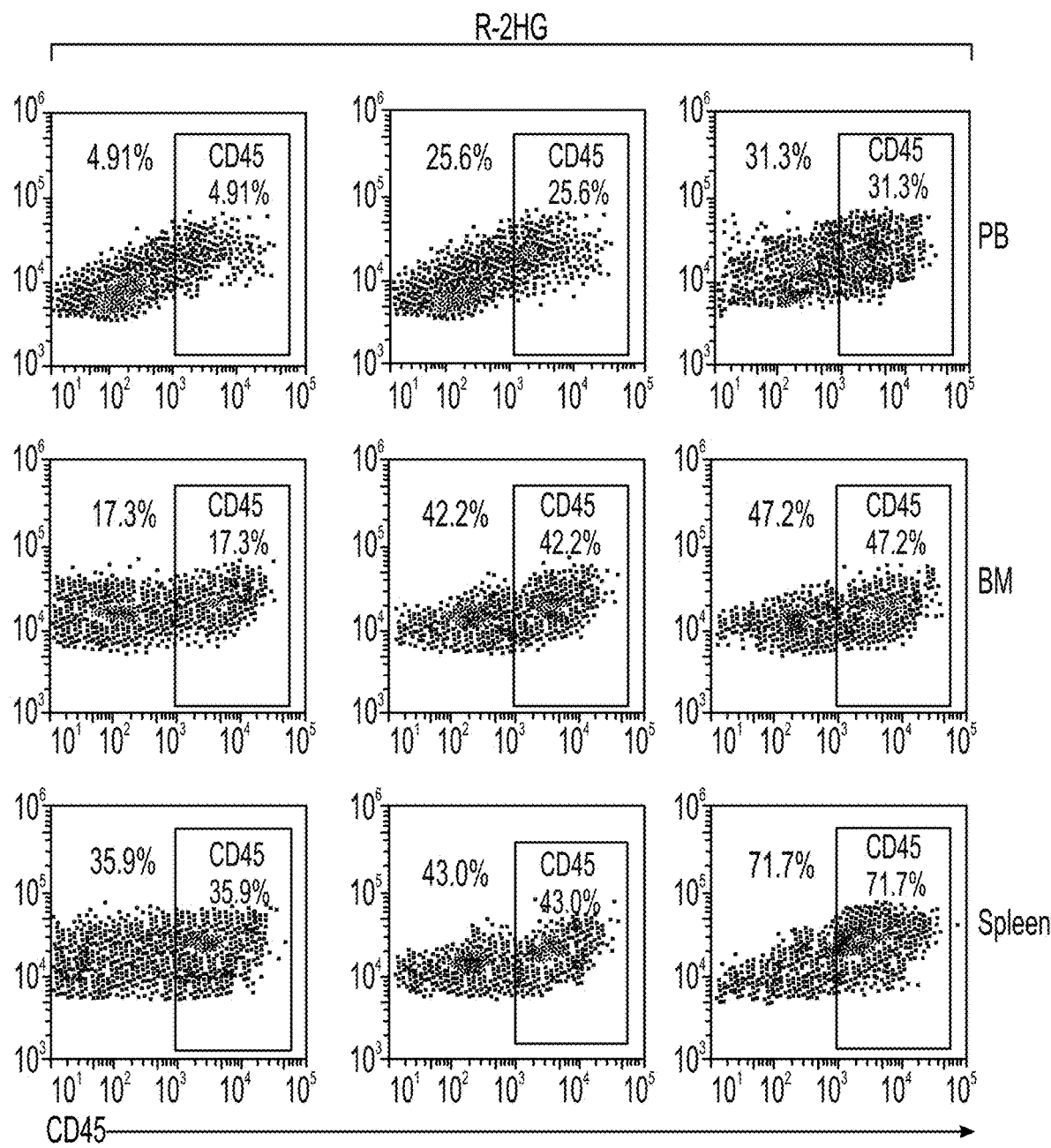
Figure 10C:
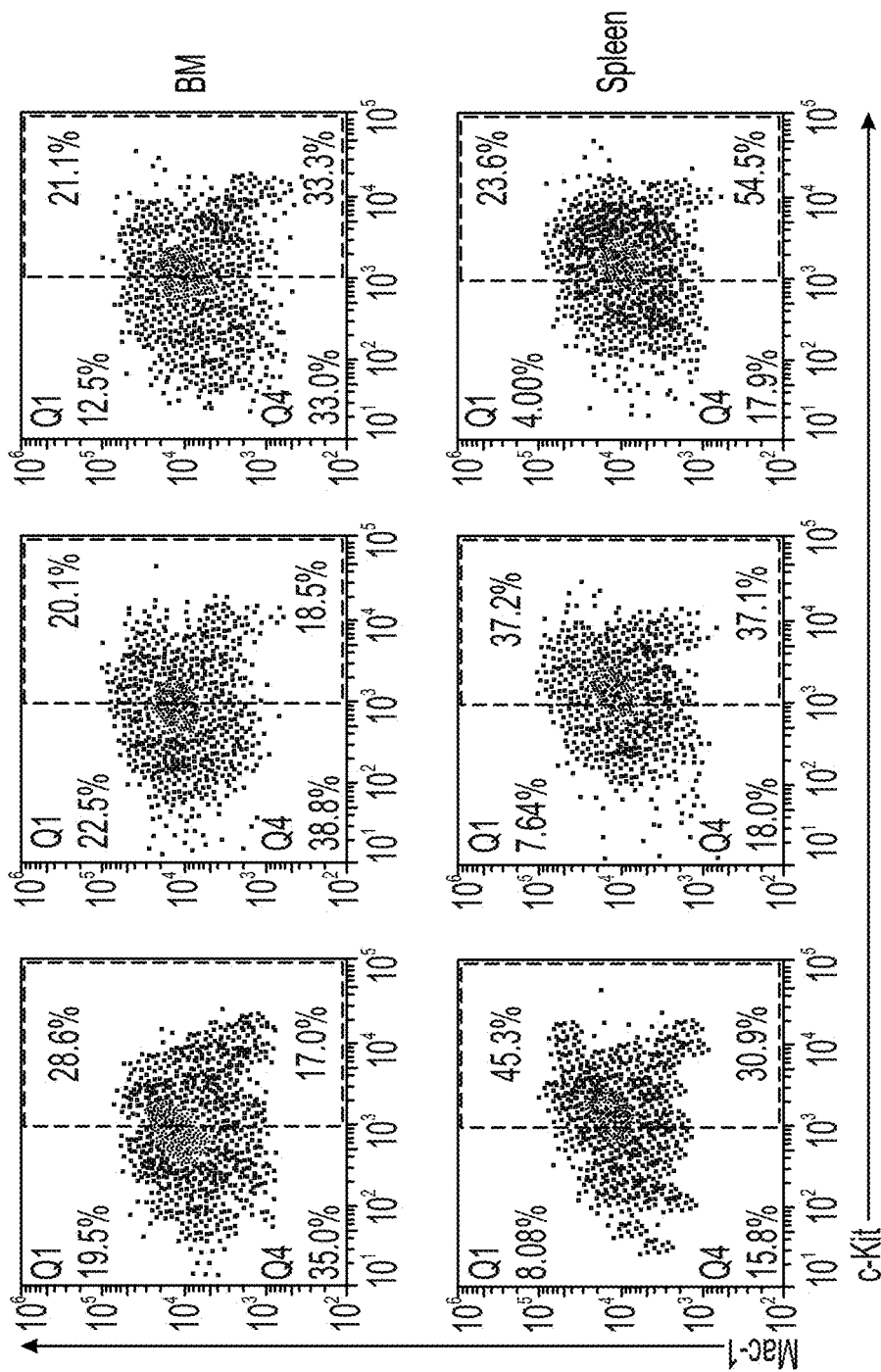
Figure 10D:
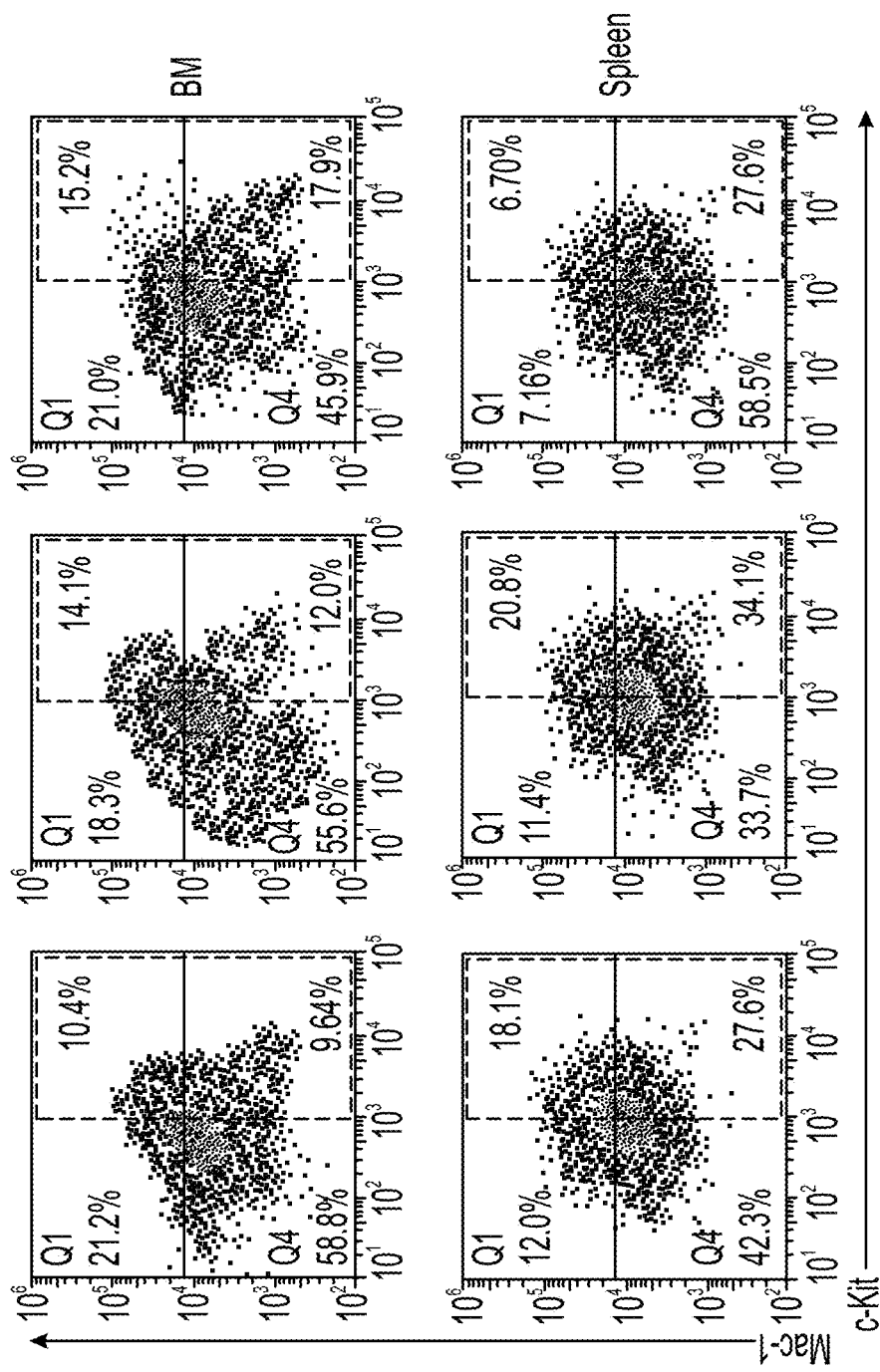

The "human-in-mouse" xeno-transplantation leukemic model was selected to evaluate the effect of R-2HG on in vivo leukemia progression. Two sensitive cells, NOMO-1 and MA9.3ITD (MLL-AF9 plus FLT3-ITD-transformed human cord blood $CD34^+$ cells)[26], were treated with R-2HG for 4 days in vitro and then directly injected into NSGS (NOD-scid IL2Rgnull-3/GM/SF, NSG-SGM3)[27] mice by tail vein injection (FIG. 1h). Compared with the control group, mice injected with R-2HG-treated cells experienced delayed development of full-blown AML (FIG. 1I), with suppressed splenomegaly and hepatomegaly (FIG. 1J), inhibited engraftment of leukemic cells (FIG. 1K, FIGS. 10A and 10B) and decreased of leukemic immature blast cells (FIGS. 10C and 10D). Thus, the in vitro and in vivo evidence demonstrate the unanticipated broad anti-leukemic activity of R-2HG, which was previously widely considered as an oncometabolite.

Example 2

Factors Correlating with R-2HG Sensitivity in Leukemic Cells

Figure 2A:
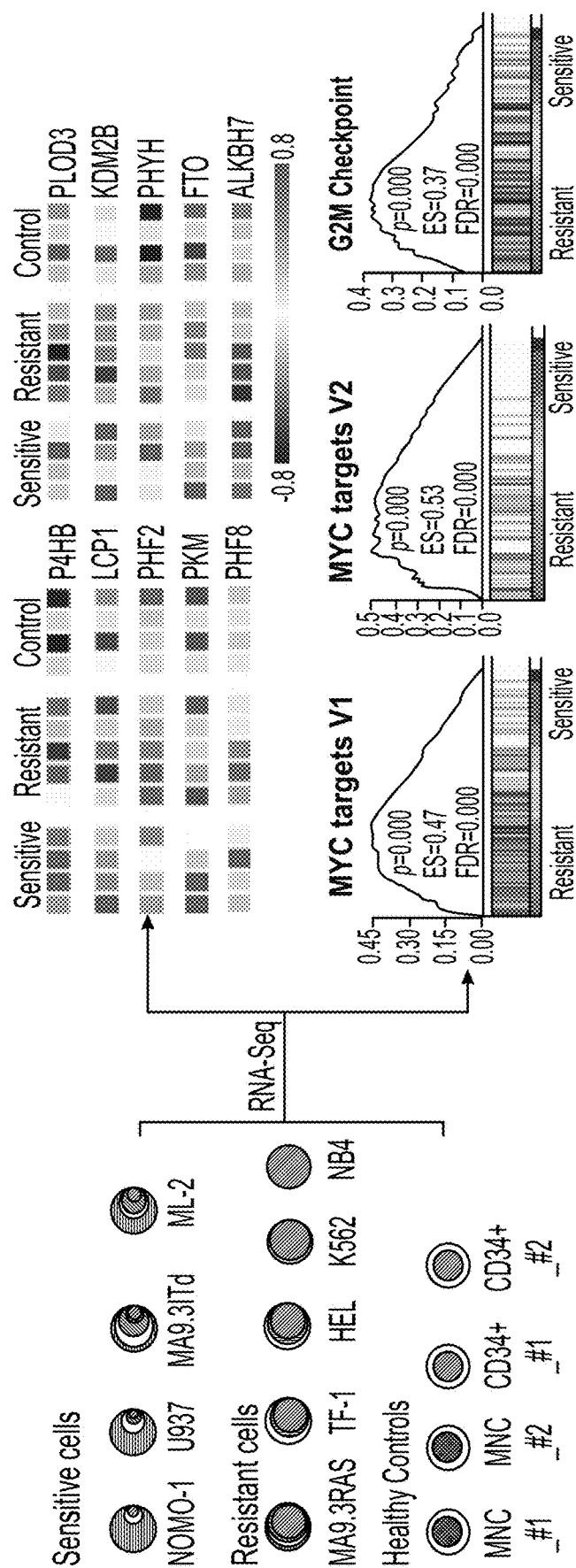
FIG. 2A-FIG. 2D identify genes and pathways related to R-2HG response.
Figure 2B:
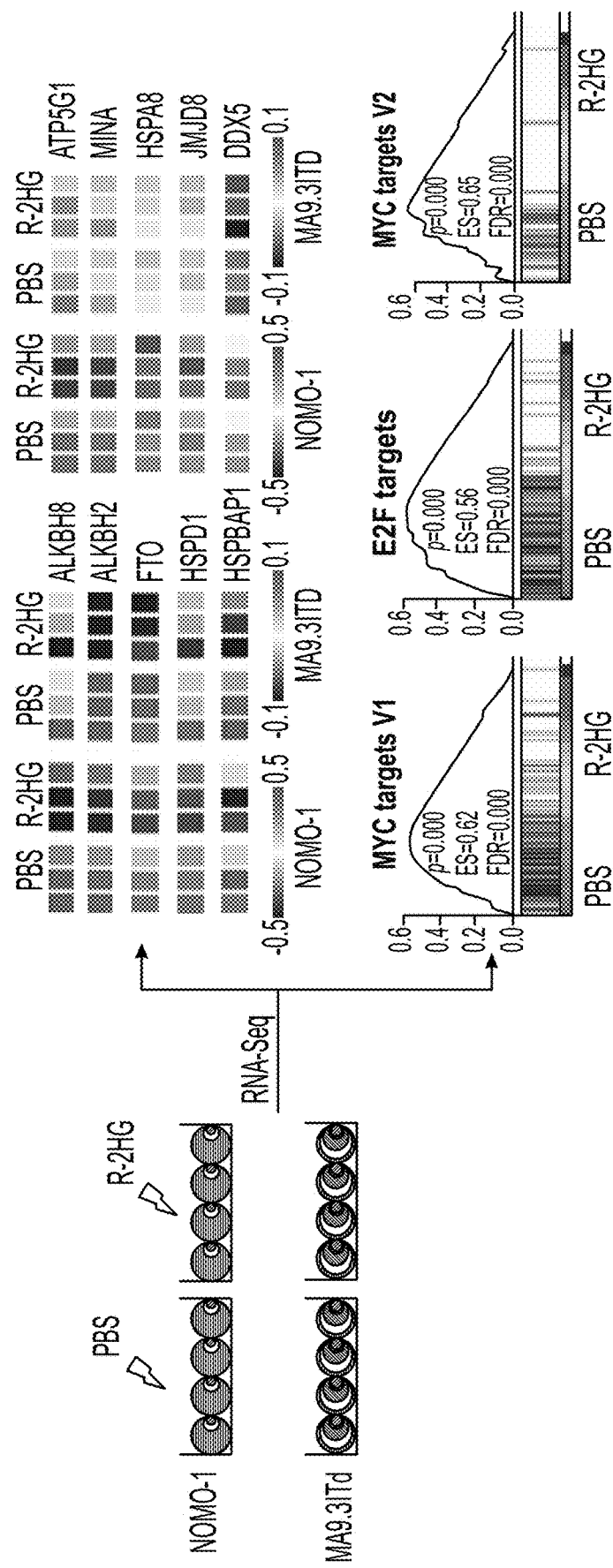
Figures 2C, 2D:
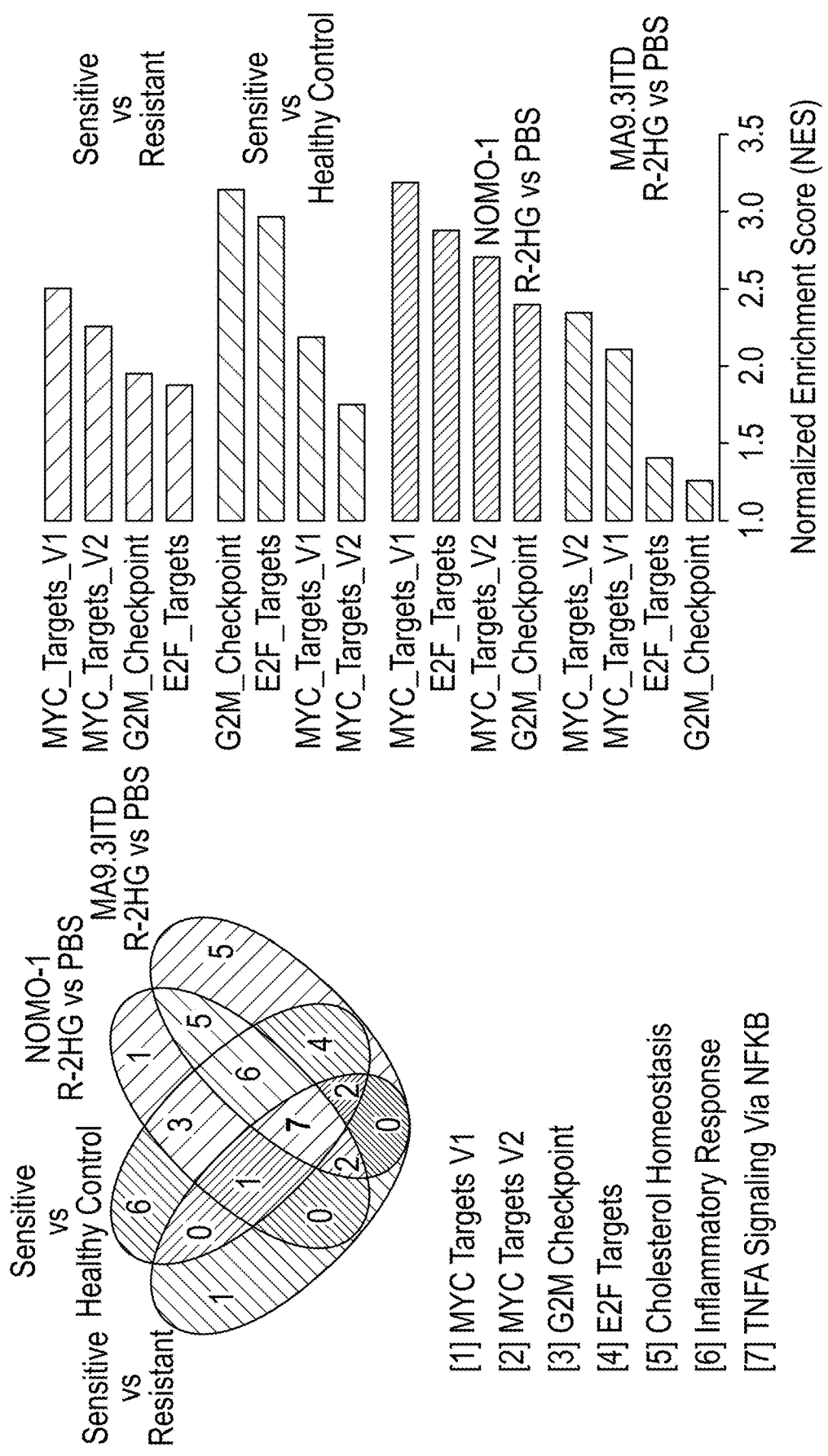
Figure 11A:
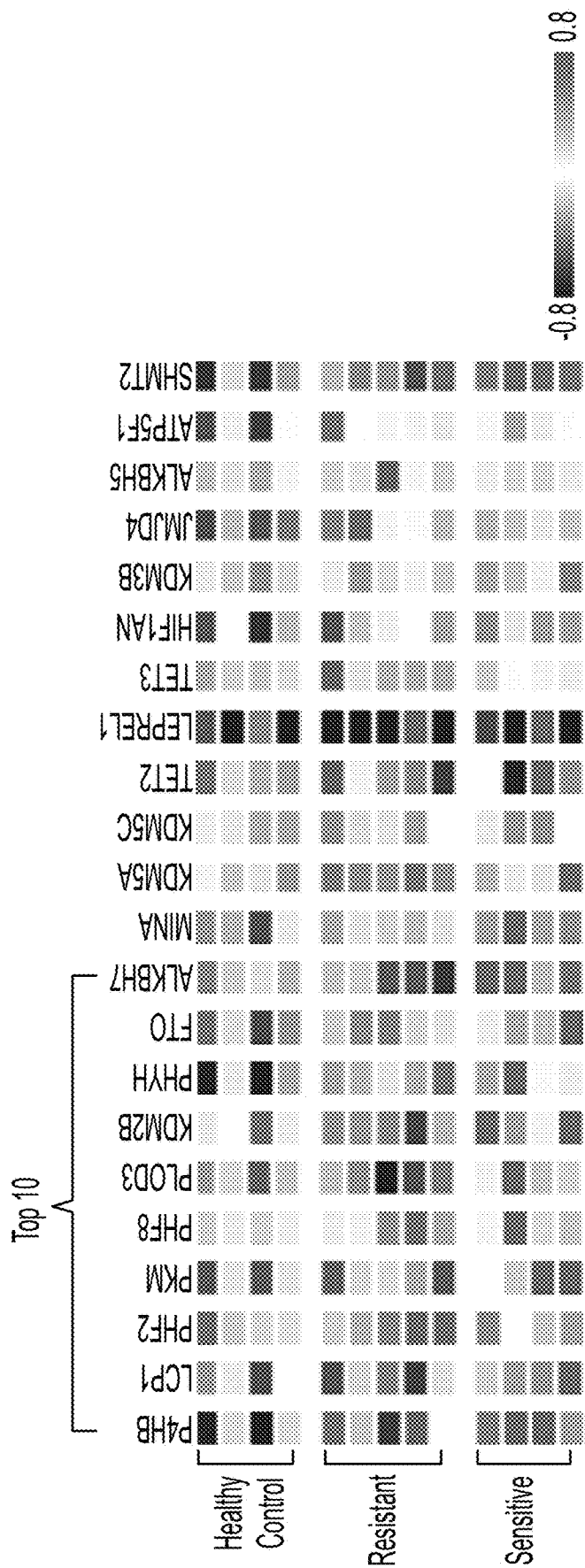
Figures 11I, 11J, 11K:
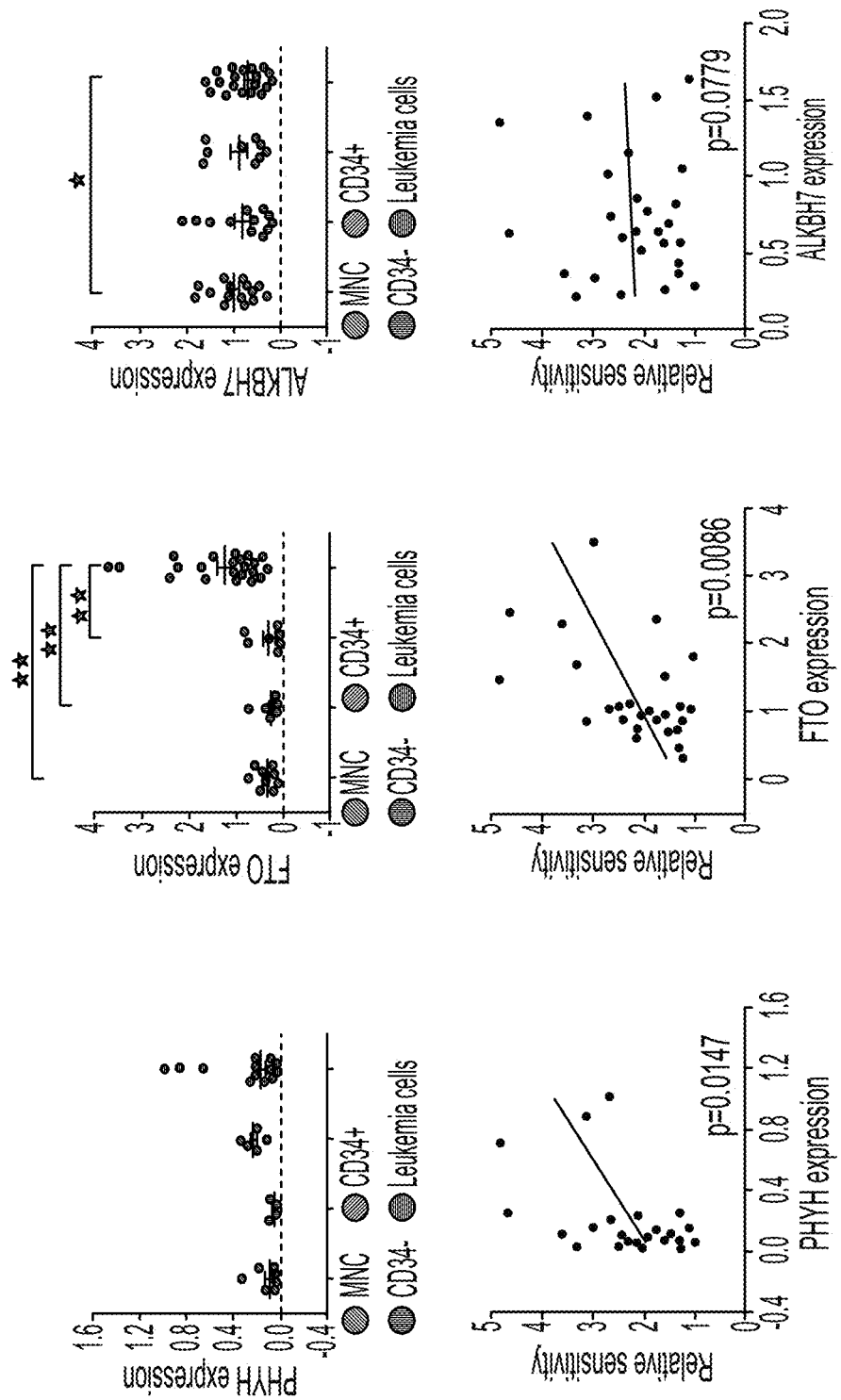
Figure 12C:
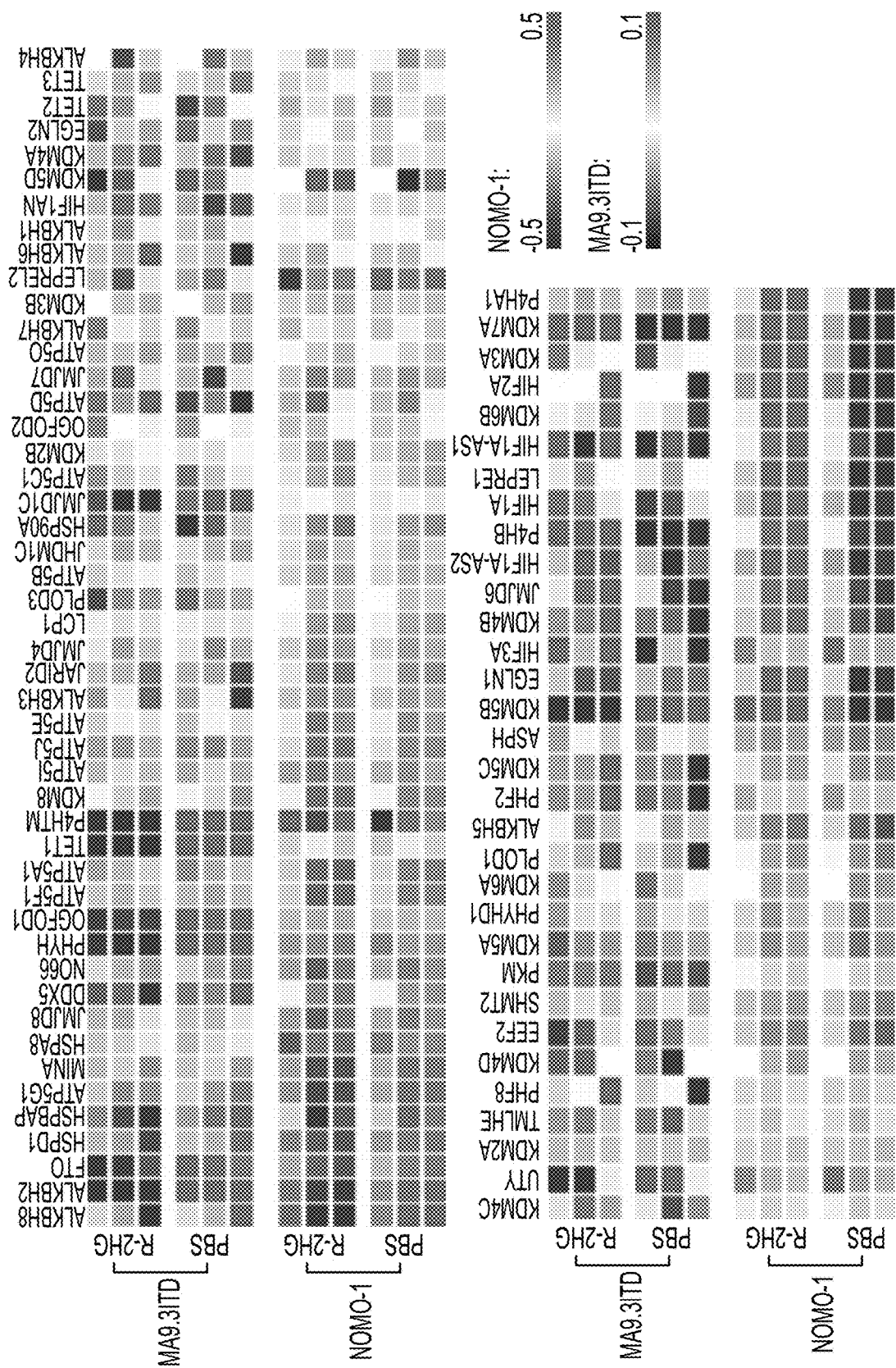
Figure 13A:
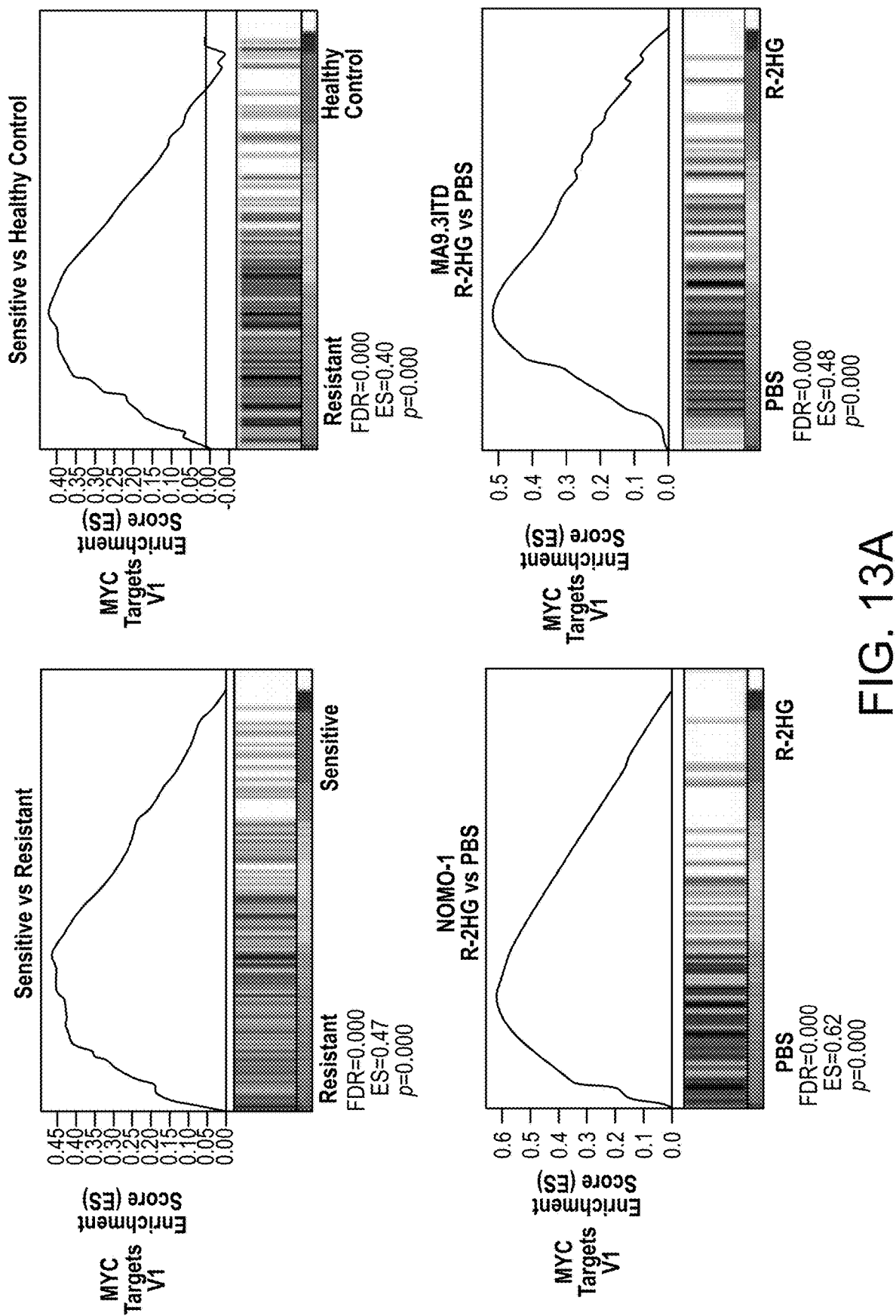
FIG. 13A-FIG. 13G show the core signaling pathways identified by RNA-seq. Based on the RNA-seq data from the samples shown in FIG. 2A (i.e., four R-2HG-sensitive leukemic samples, five R-2HG-resistant leukemic samples, and four healthy control samples) and the RNA-seq data from the samples shown in FIG. 2B (i.e., NOMO-1 and MA9.3ITD leukemic samples treated with PBS or R-2HG), GSEA identified 7 core enriched gene sets (or signaling pathways) from the following four groups of comparisons: sensitive leukemia cells vs. resistant leukemia cells; sensitive leukemia cells vs. healthy control cells; R-2HG-treated NOMO-1 vs. PBS-treated NOMO-1; and R-2HG-treated MA9.3ITD vs. PBS-treated MA9.3ITD. Among the 7 gene sets, FIG. 13A) MYC targets V1, FIG. 13B) MYC targets V2, FIG. 13C) G2M checkpoint and FIG. 13D) E2F targets were consistently enriched in resistant cells compared with sensitive cells, and also enriched in sensitive cells compared with healthy controls, and notably suppressed by R-2HG treatment in both NOMO-1 and MA9.3ITD cells, whereas the other three genes sets including FIG. 13E) Cholesterol homeostasis, FIG. 13F) Inflammatory response and FIG. 13G) TNFA signaling via NF-kB show the largely opposite patterns. ES, enrichment score. P<0.001 and FDR<0.05 were used as cut-off for statistic significance.
Figure 13B:
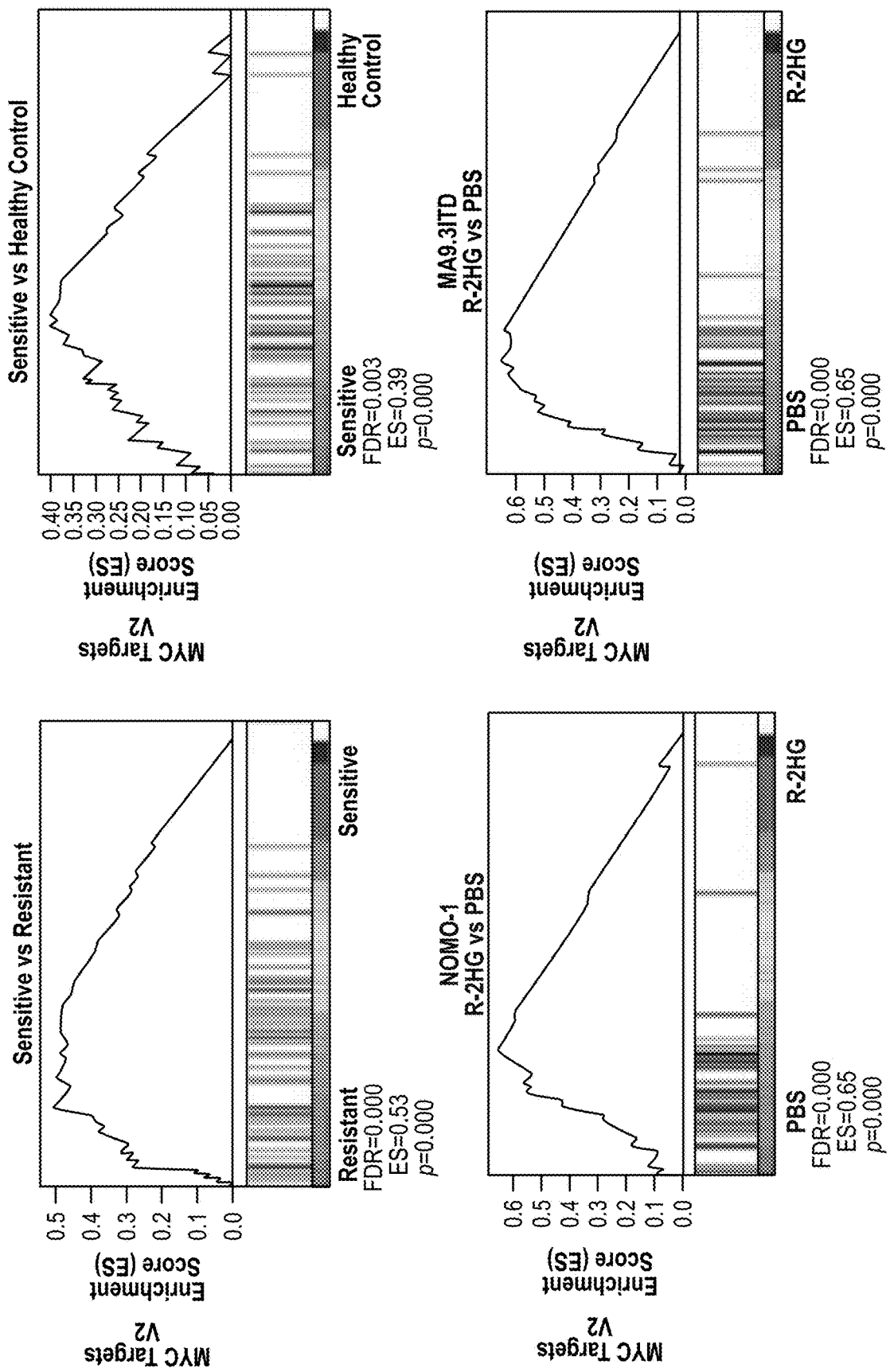
Figure 13C:
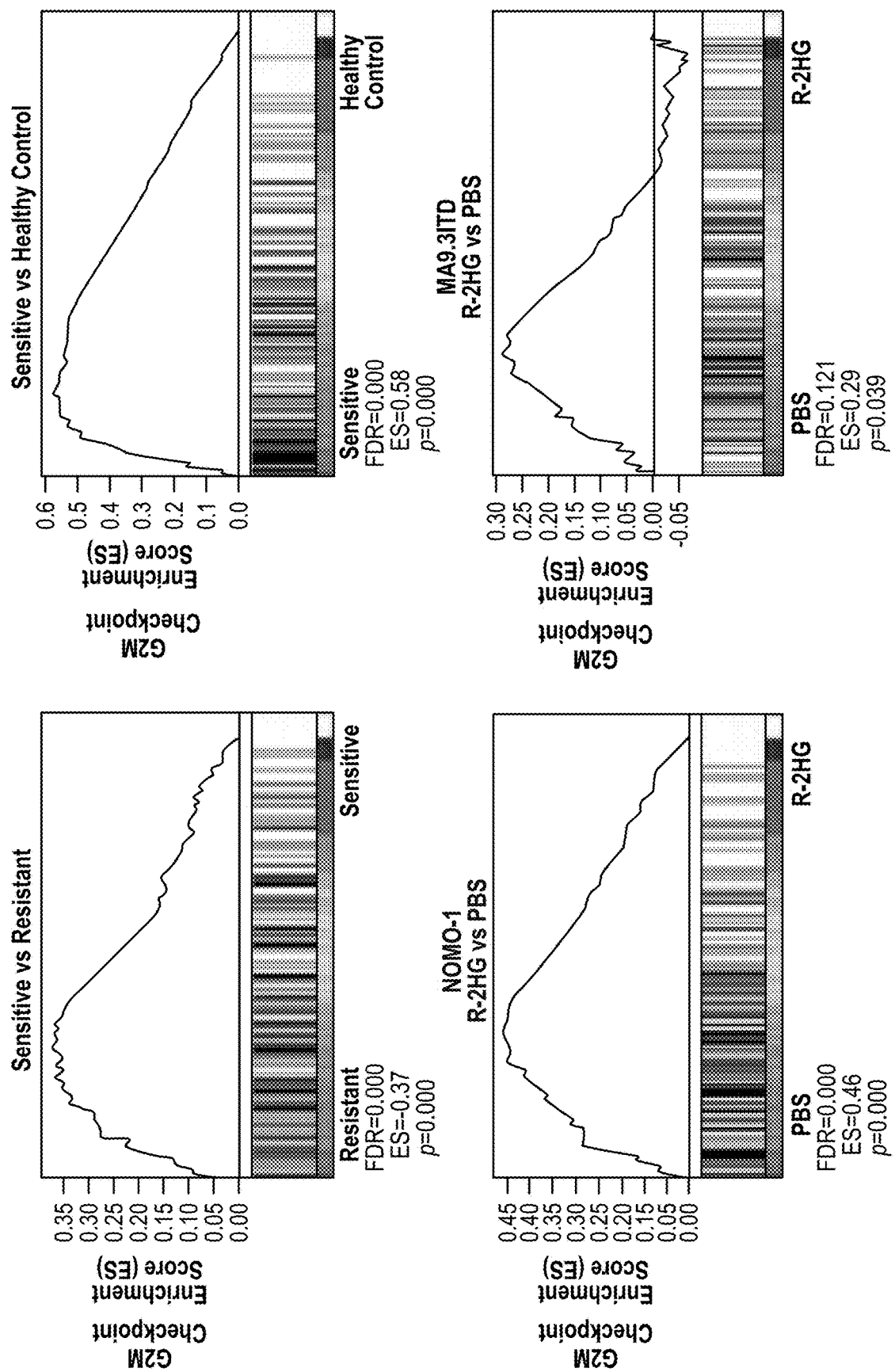
Figure 13D:
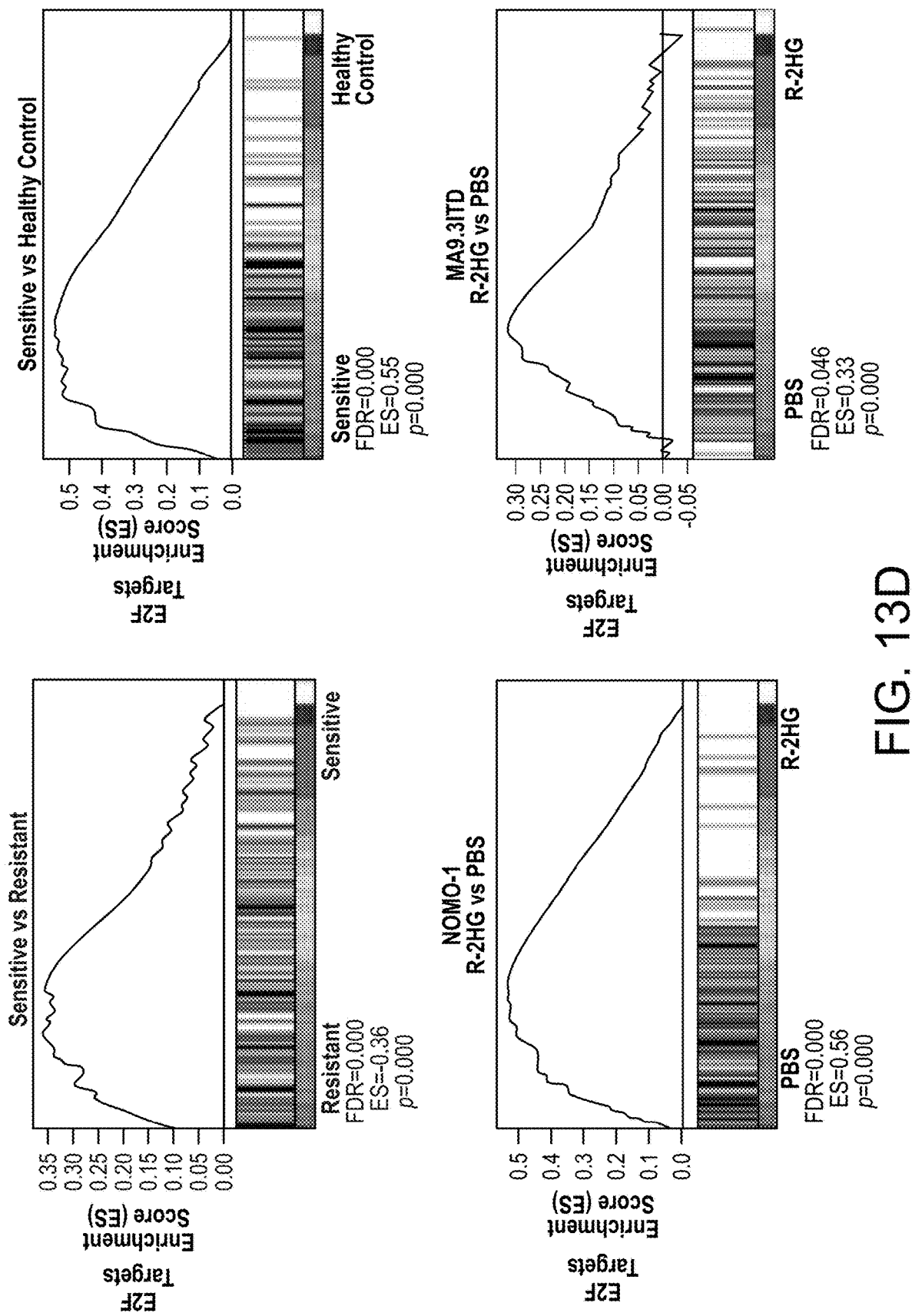
Figure 13E:
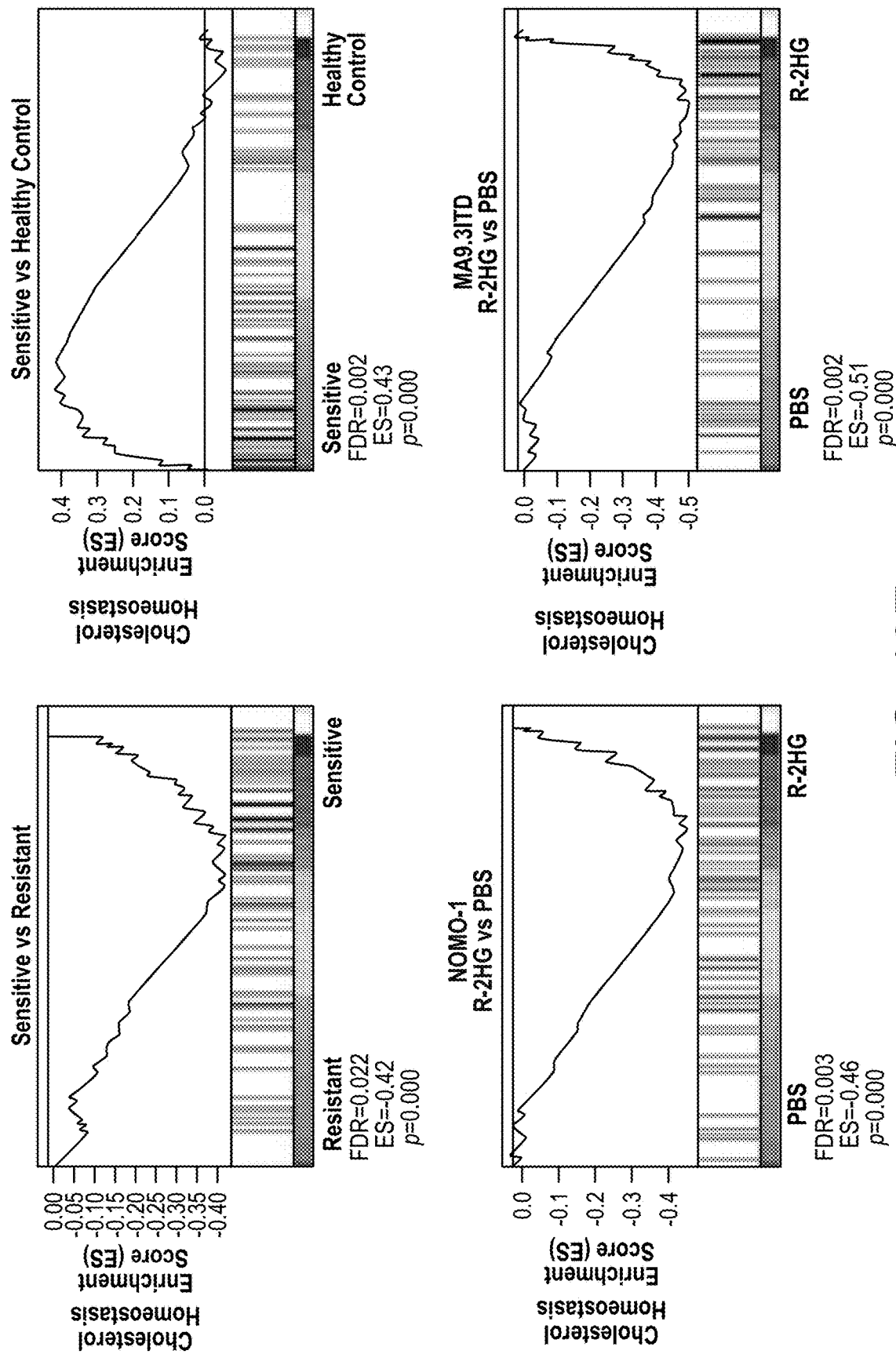
Figure 13F:
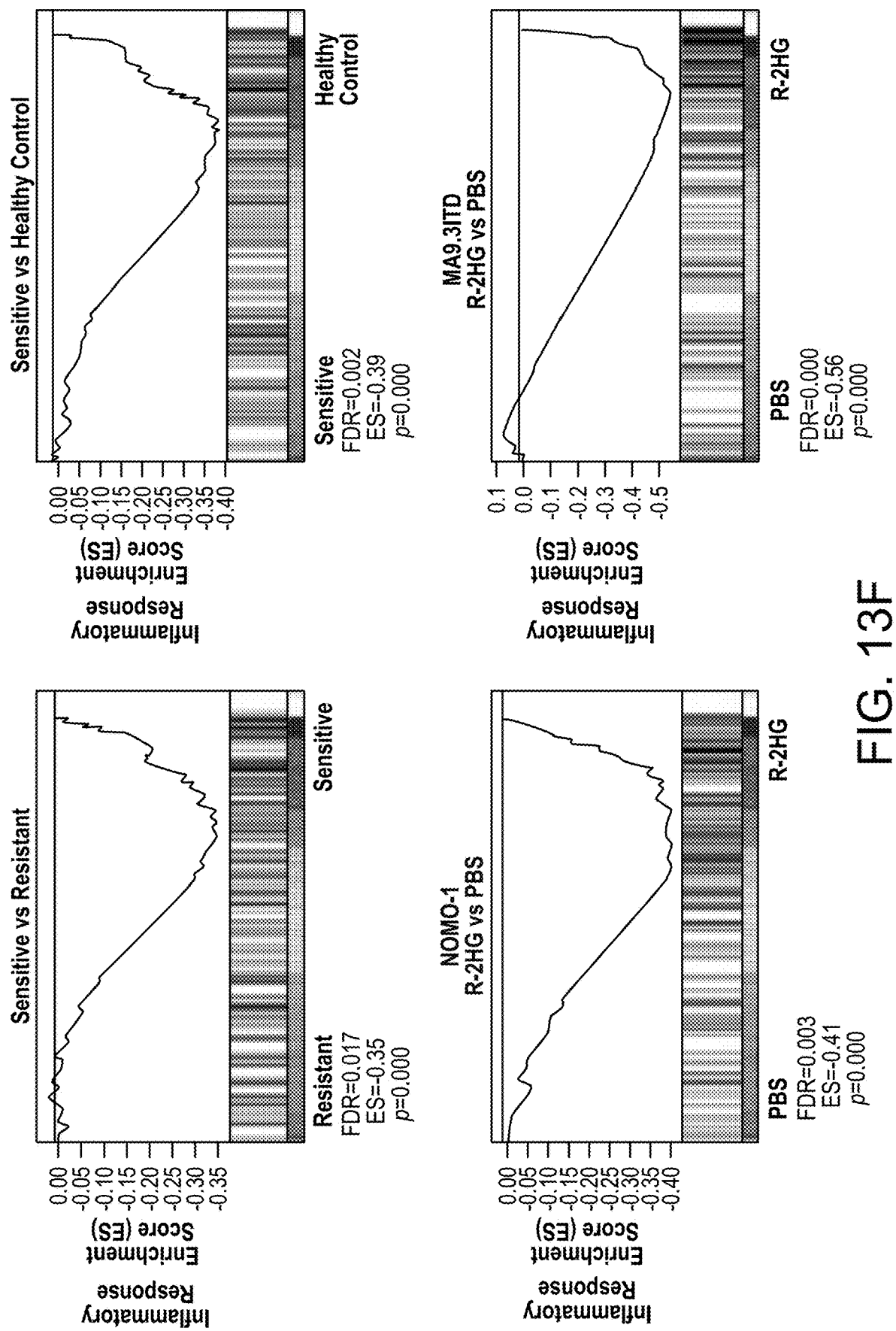
Figure 13G:
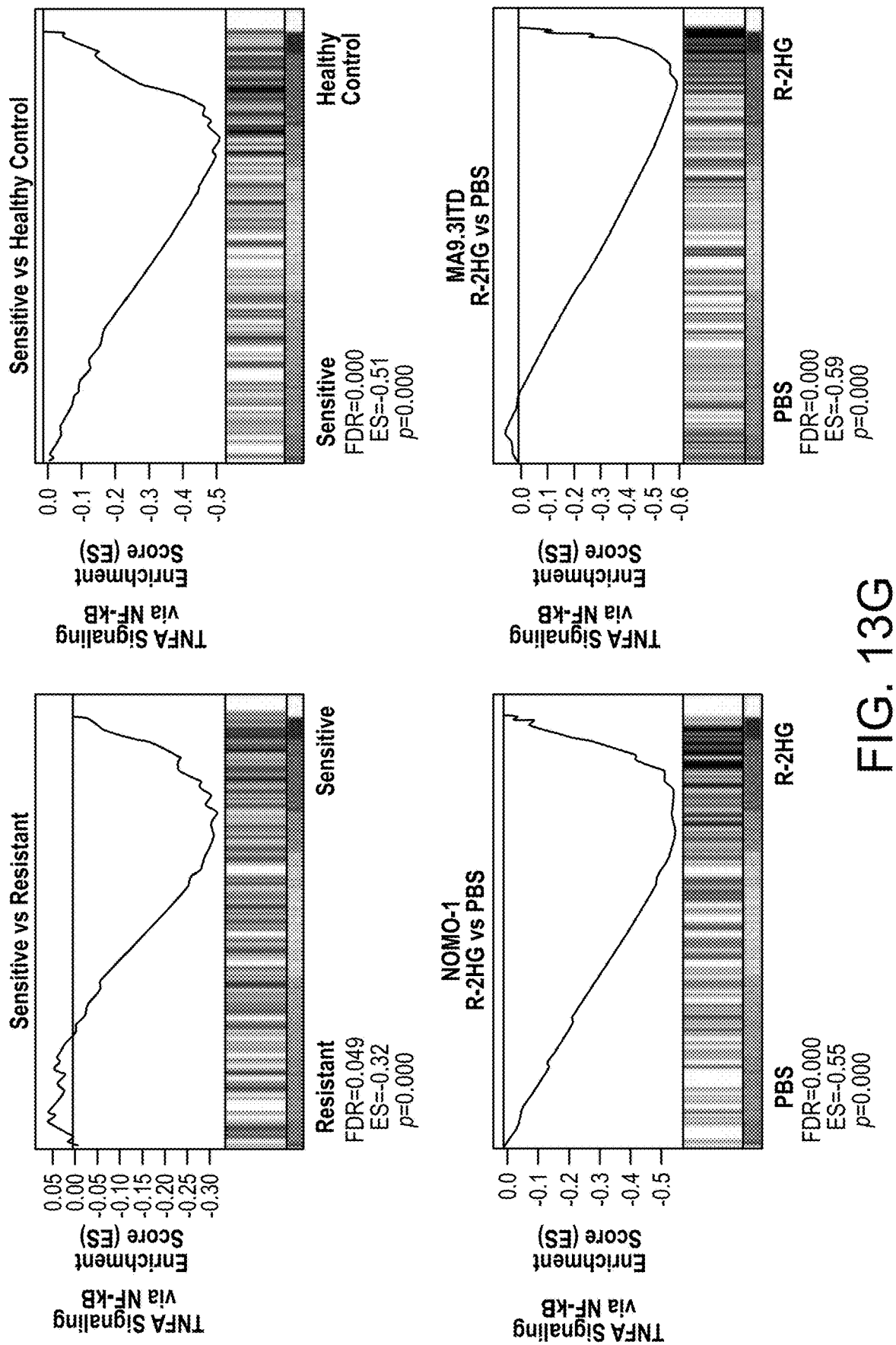

Functionally, R-2HG acts as a competitive inhibitor of Fe(II)/α-ketoglutarate (α-KG)-dependent dioxygenases (Table 2)[9]. To determine which dioxygenase(s) and signaling pathway(s) are responsible for the response of leukemic cells to R-2HG, RNA-seq with 4 (R-2HG-)sensitive and 5 resistant leukemia cell lines, along with 4 healthy control samples were performed (FIG. 2A). A set of dioxygenases were identified to be highly expressed in R-2HG-sensitive AML cells and exhibit a positive correlation in expression with the degree of R-2HG inhibitory effect across the AML samples (FIG. 2A, FIG. 11A); thus, they are potential targets of R-2HG that mediate R-2HG effect. A qPCR analysis with an expanded cohort of leukemic and normal control samples confirmed the positive correlation between gene expression levels and degrees of R-2HG effect across leukemic samples for 7 out of the top 10 dioxygenase genes (FIG. 2A and FIGS. 11B-11K); however, only FTO is expressed at a significantly higher level in leukemic samples compared to all three types of normal control (mononuclear, $CD34^+$ and $CD34^-$) cells (FIG. 11J). RNA-seq assays of NOMO-1 and MA9.3ITD samples with and without R-2HG treatment were then conducted. It was found that FTO is also amongst the dioxygenase genes that are significantly down-regulated by R-2HG in both leukemic cell lines (FIG. 2B and FIGS. 12A-12C).

TABLE 2

List of the potential α-KG-dependent/related enzymes.

ALKBH1
ALKBH2
ALKBH3
ALKBH4
ALKBH5
ALKBH6
ALKBH7
ALKBH8
APHD1
APHD2
ASPH
ATP5A1
ATP5B
ATP5C1
ATP5D
ATP5E
ATP5F1
ATP5G1
ATP5I
ATP5J
ATP5O
BBOX1
BBOX2
DDX5
EEF2
EGLN1
EGLN2
EGLN3
FIH1
FTO
HIF1AN
HR
HSP90AA1
HSPA8
HSPBAP1
HSPD1
JARID2
JHDM1C
JMJD1C
JMJD4
JMJD6
JMJD6
JMJD7
JMJD8
KDM2A
KDM2B
KDM3A
KDM3B
KDM4A
KDM4B
KDM4C
KDM4D
KDM5A
KDM5B
KDM5C
KDM5D
KDM6A
KDM6B

TABLE 2-continued

List of the potential α-KG-dependent/related enzymes.

KDM7A
KDM8
LCP1
LEPRE1
LEPREL1
LEPREL2
MINA
NO66
OGFOD1
OGFOD2
P4HA1
P4HA2
P4HA3
P4HB
P4HTM
PAHX-AP1
PHF2
PHF8
PHYH
PHYH
PHYHD1
PKM2
PLOD1
PLOD2
PLOD3
SHMT2
TET1
TET2
TET3
TMLHE
UTY

Figures 14A, 14B:
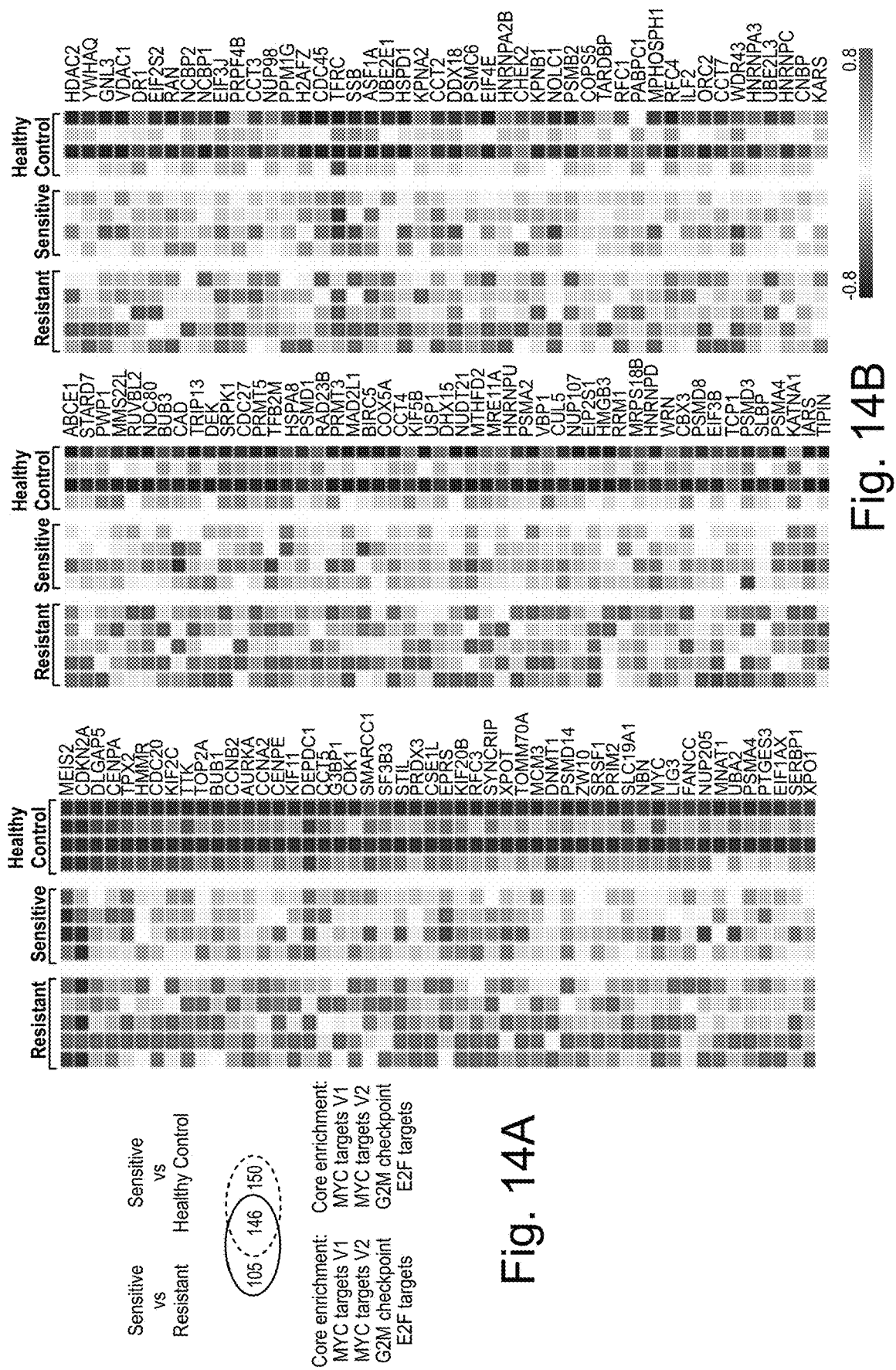
FIG. 14A-FIG. 14F show the core genes from enriched MYC, G2M and E2F signaling pathways.
Figures 14C, 14D:
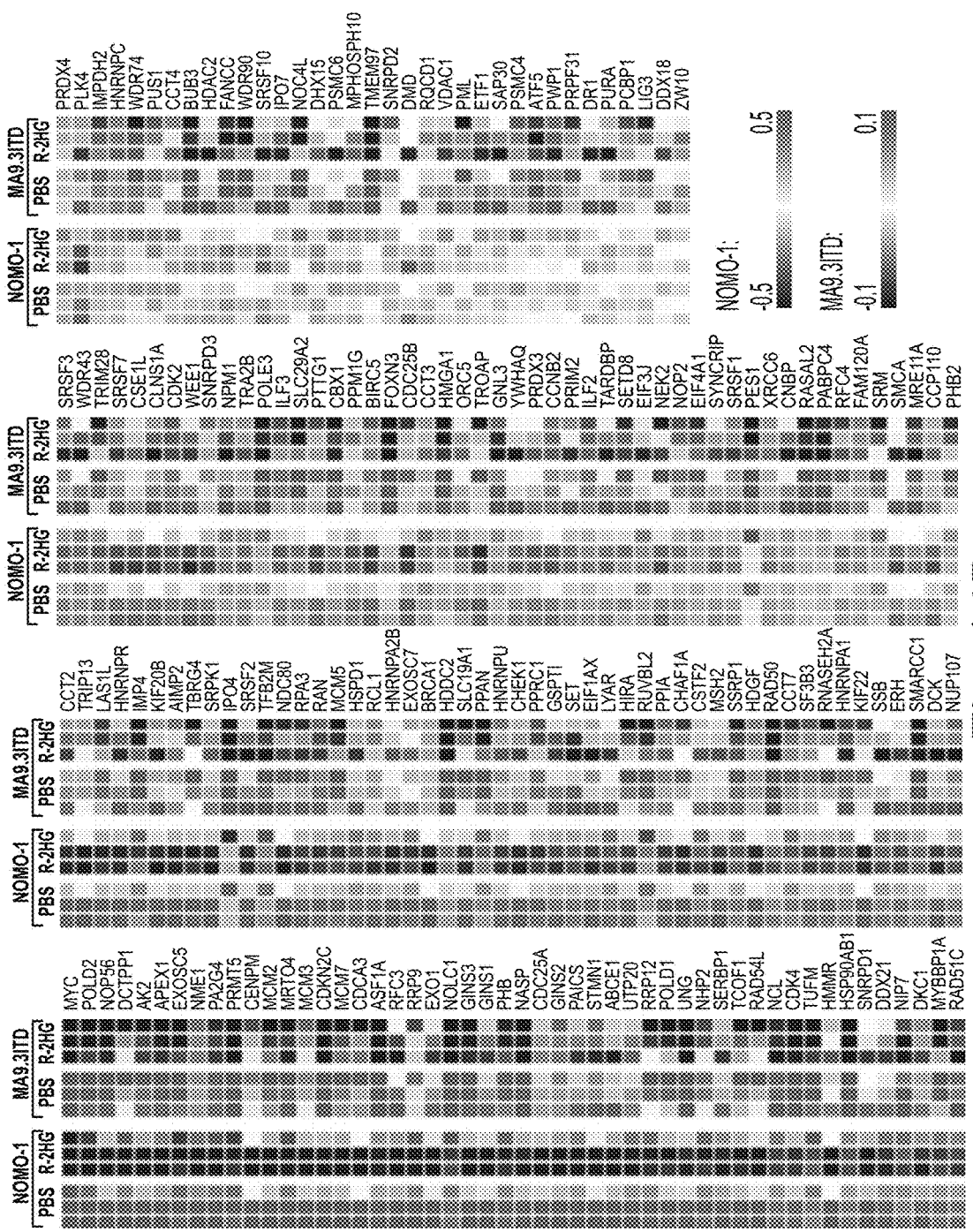
Figure 14E:
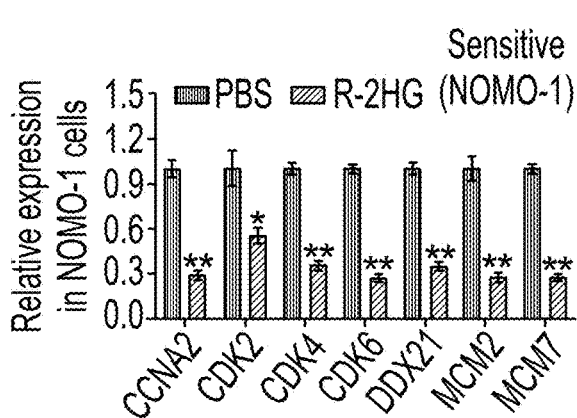
Figure 14F:
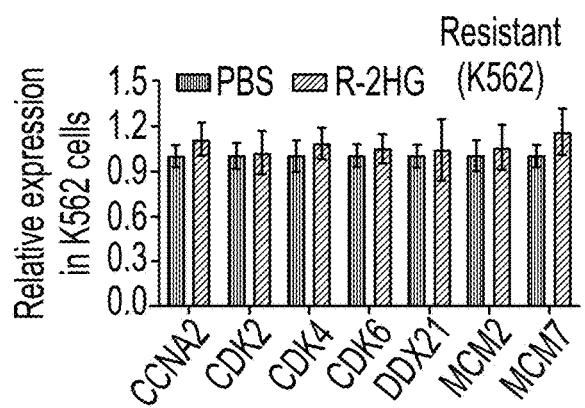

Through gene set enrichment analysis (GSEA)[28] of the two RNA-seq datasets, 7 gene sets were identified that are strongly correlated with R-2HG sensitivity/response, especially the MYC targets sets (FIGS. 2A-2C and FIGS. 13A-13G). Among these pathways, MYC, G2M and E2F signaling are hyper-activated in R-2HG-resistant leukemic samples while moderately activated in R-2HG-sensitive samples, relative to normal control samples (FIG. 2D and FIGS. 13A-13G, 14A and 14B), suggesting their hyper-activation might be responsible for the resistance to R-2HG. Importantly, R-2HG also suppressed the activities of MYC, G2M and E2F signaling pathways in R-2HG sensitive cells (FIGS. 2B-2D, FIGS. 13A-13G, and FIGS. 14C and 14D). qPCR data also confirmed that R-2HG inhibited the major component genes of the MYC signaling in sensitive cells, but not in resistant cells (FIGS. 14E-14F). The fact that MYC, G2M and E2F signaling act concordantly to regulate G1/S and G2/M cell cycle transition[29,30] might be the major mechanism by which R-2HG causes cell cycle arrest and apoptosis in sensitive cells (see FIGS. 1C-1E, and FIG. 8).

Example 3

R-2HG Targets FTO in Sensitive Leukemic Cells

Figure 3A:
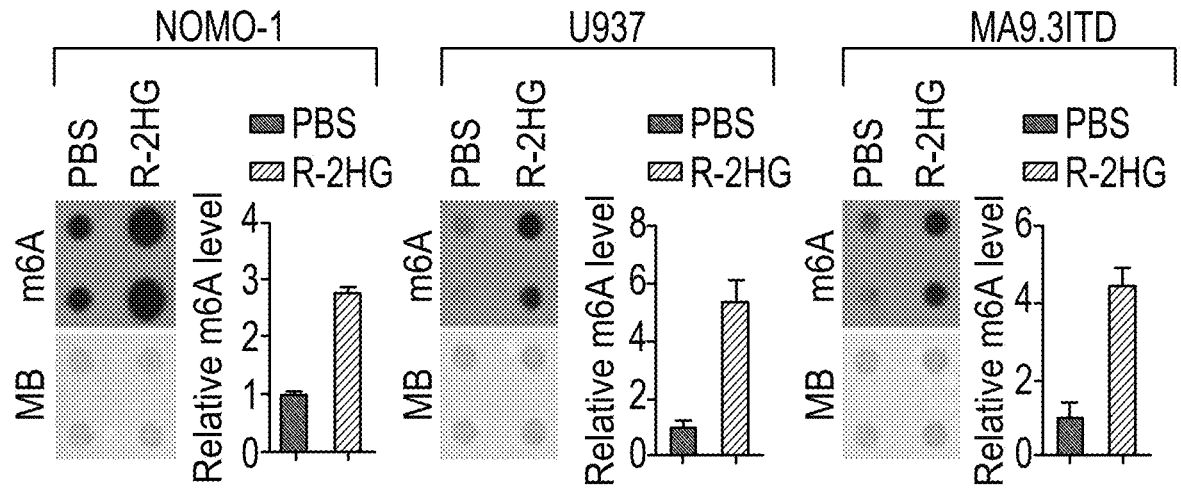
FIG. 3A-FIG. 3J set forth data demonstrating that R-2HG induces $m^6A$ modification via inhibiting FTO.
Figure 3B:
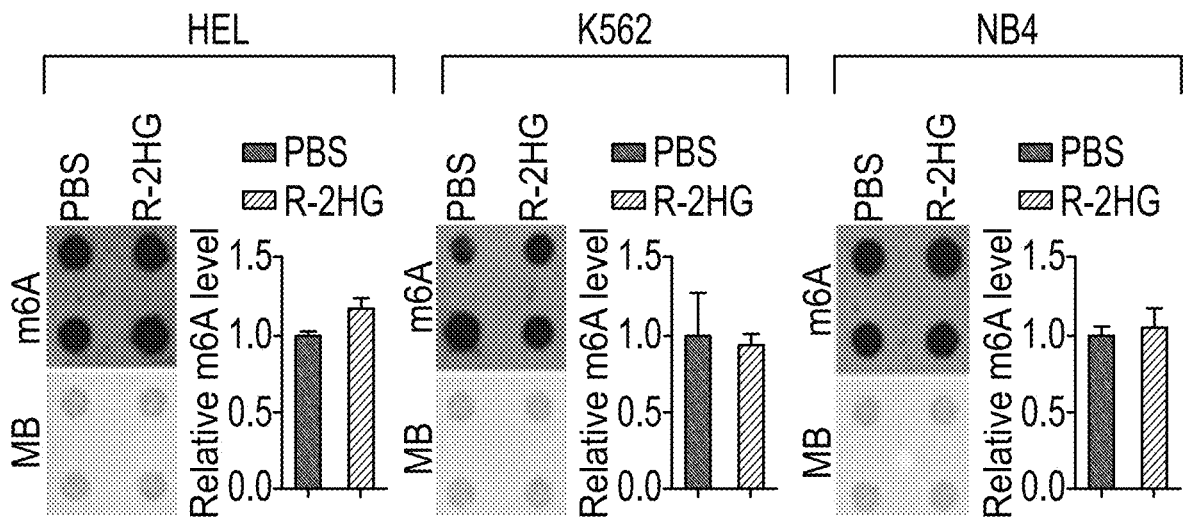
Figure 15A:
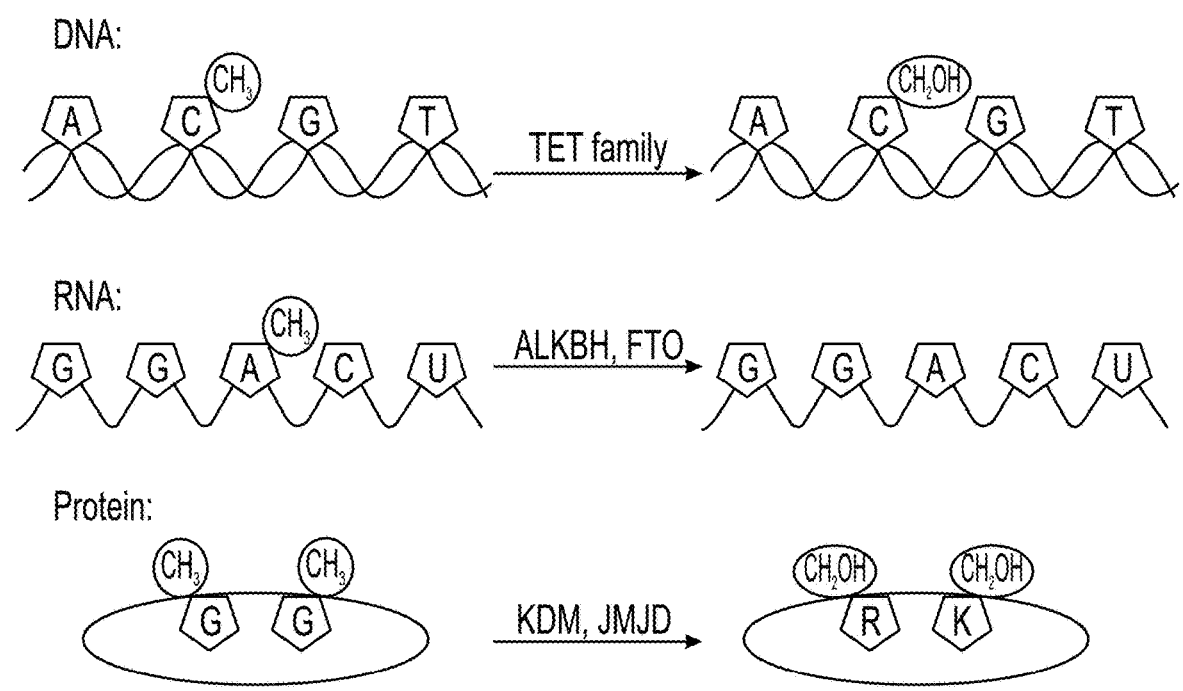
FIG. 15A-FIG. 15H set forth a correlation analysis between DNA/RNA/histone demethylases expression and sensitivity to R-2HG, as well as the effects of R-2HG on DNA and histone methylation.
Figure 15B:
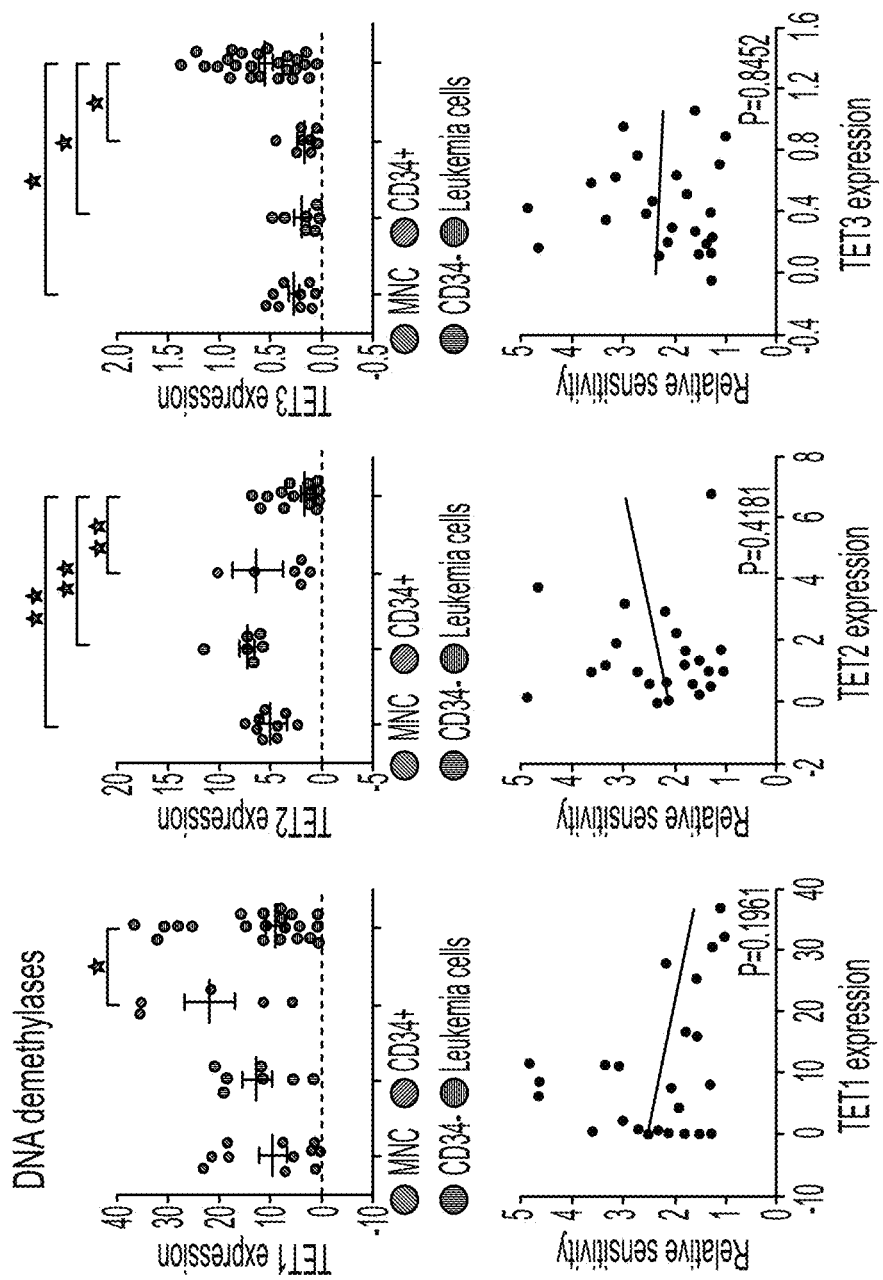
Figure 15C:
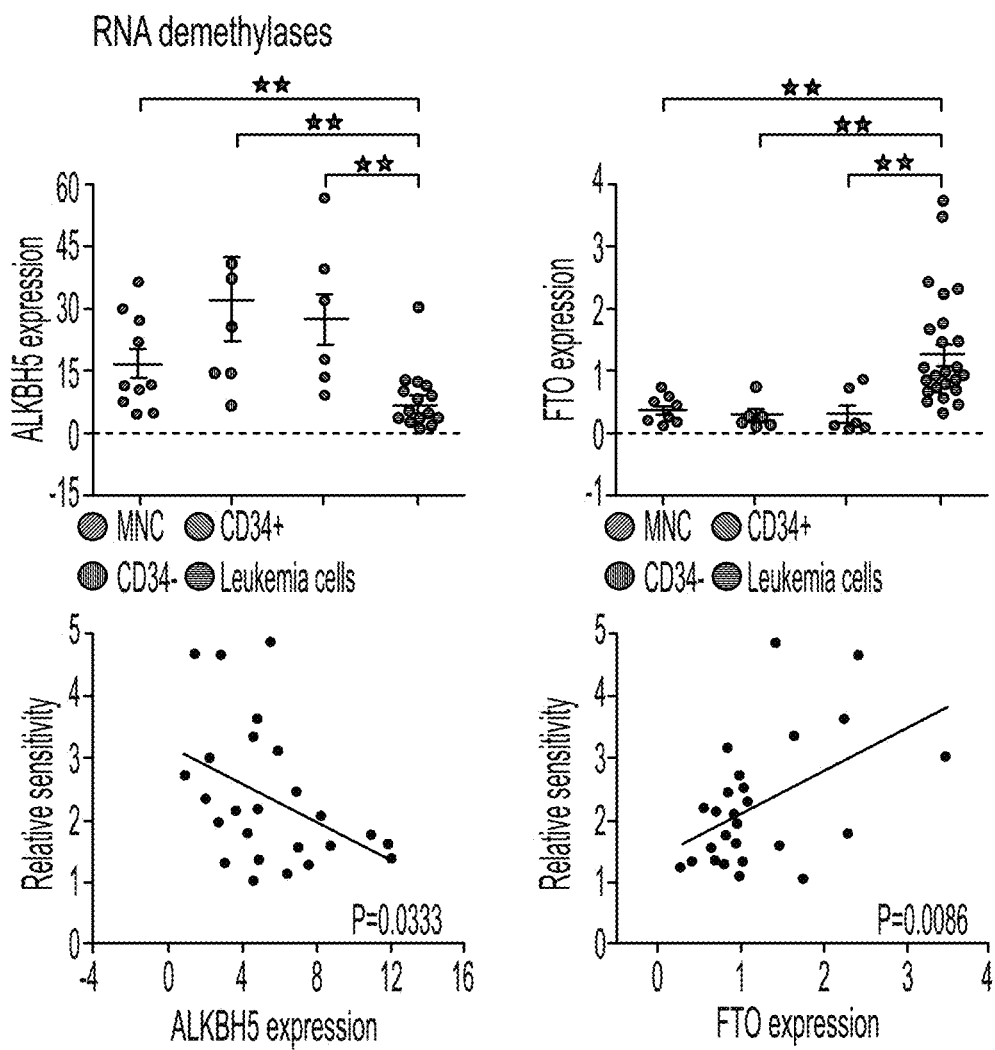
Figure 15D:
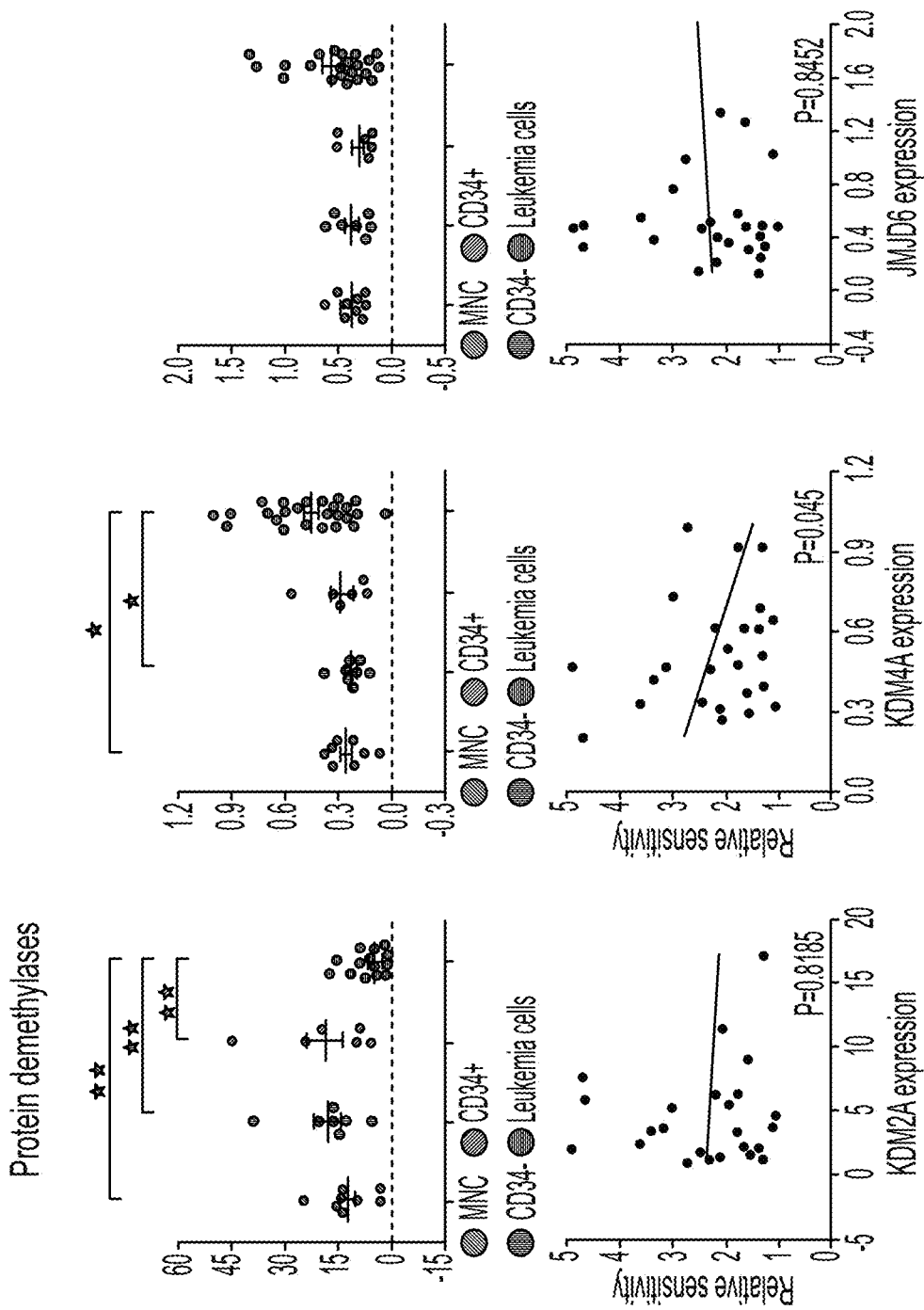
Figure 15E:
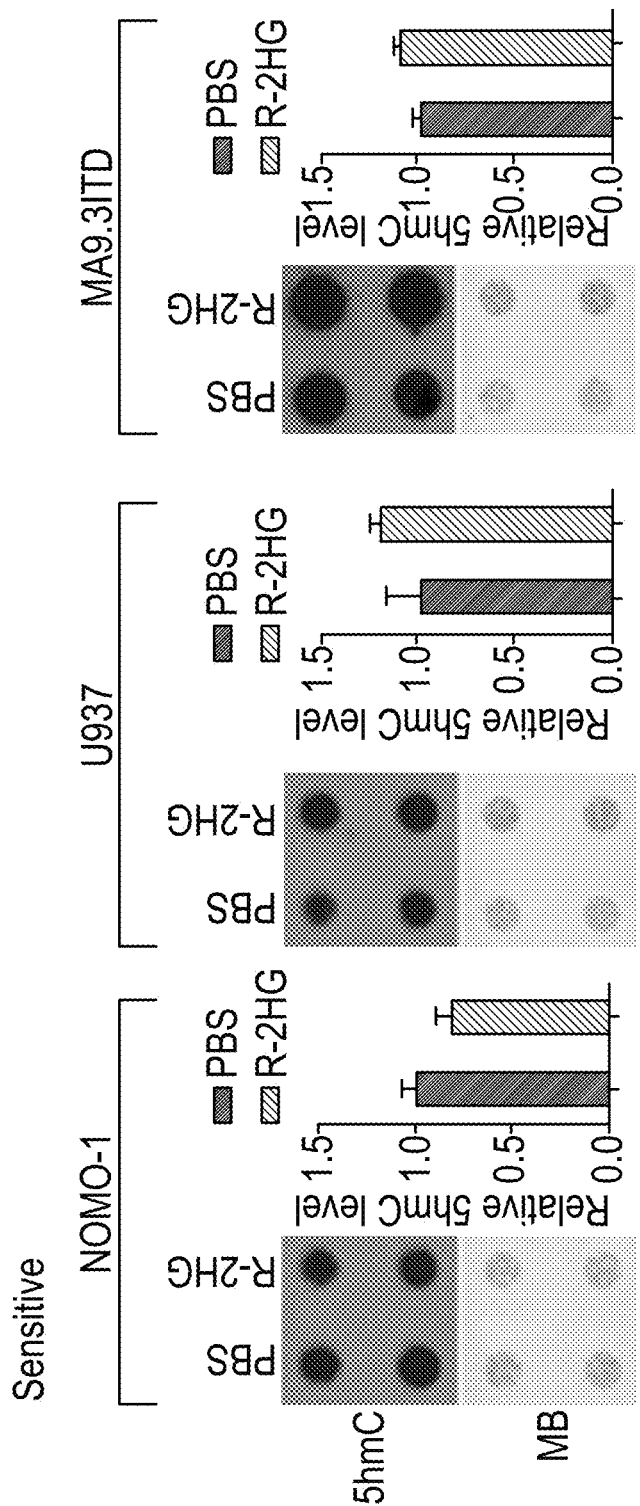
Figure 15F:
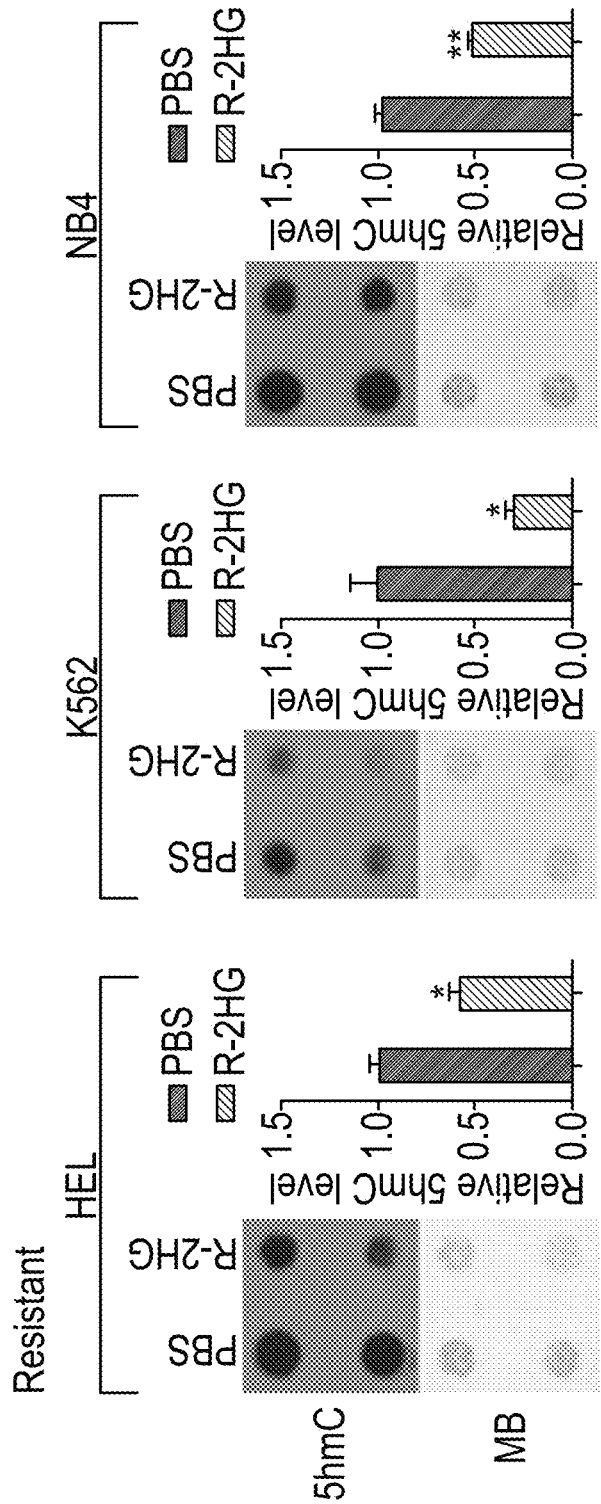
Figure 15G:
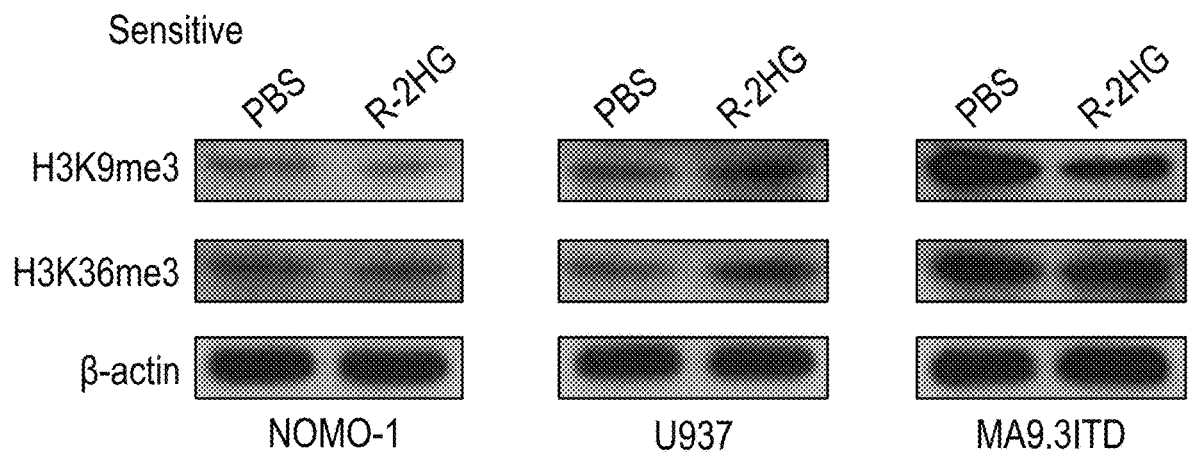
Figure 15H:
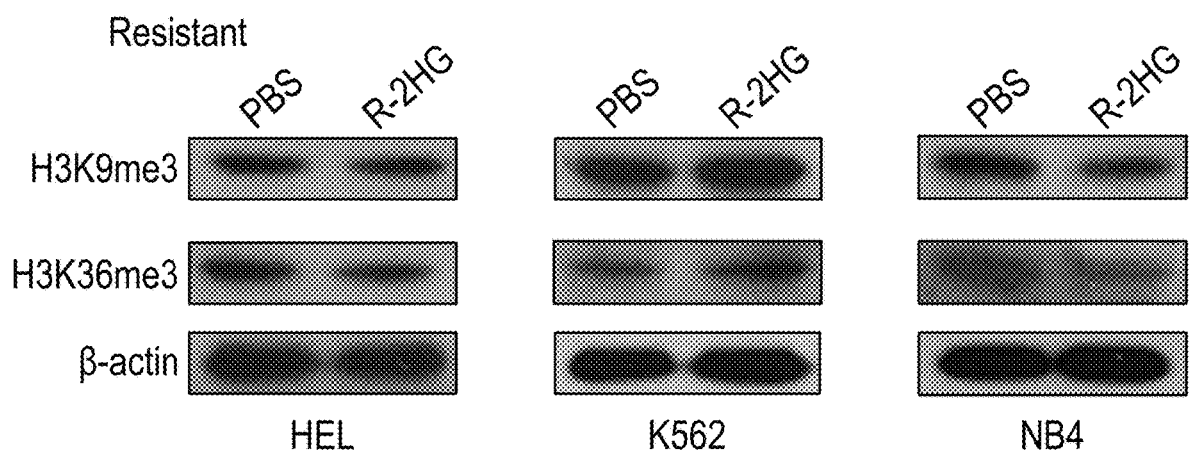

R-2HG has been shown to inhibit the functions of DNA and histone demethylases such as TET2, JMJD and KDM, leading to hypermehtylated DNA and histones[11,31,32]. FTO and ALKBH5, two major $m^6A$ demethylases, are also Fe(II)/α-KG dependent dioxygenases[33,34], and thus R-2HG may also target them in leukemic cells. To determine which epigenetic (DNA, RNA or histone) modification is responsible for R-2HG's anti-leukemic activity, expression levels of the genes encoding DNA demethylases (TET1/2/3), $m^6A$ demethylases (FTO and ASLKBH5) and histone demethylases (KDM2A, KDM4A and JMJD6) in leukemic samples and healthy control samples were first analyzed by qPCR. Notably, FTO is the only gene showing a significantly positive correlation in expression with R-2HG sensitivity across the leukemia samples, and is also overexpressed in leukemia samples relative to normal controls (FIGS. 15A-15D). Second, R-2HG treatment was shown to dramatically increase global RNA $m^6A$ modification in the sensitive leukemia cells (FIG. 3A), but not in the resistant cells (FIG. 3B). In contrast, R-2HG caused a decrease in 5-hydroxymethylcytosine (5hmC) modification in resistant cells, but not in sensitive cells (FIGS. 15E-15F); no consistent and significant increase in histone methylation was observed in either sensitive or resistant leukemic cells upon R-2HG treatment (FIGS. 15G-15H). Together, the data suggests that FTO and the associated RNA $m^6A$ modification are the major mediators of R-2HG's anti-leukemic effect in sensitive cells.

Figure 3C:
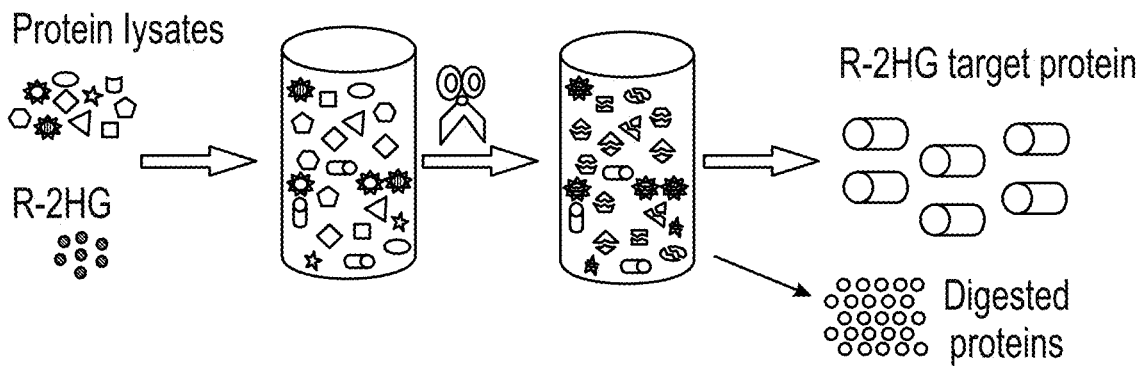
Figure 3D:
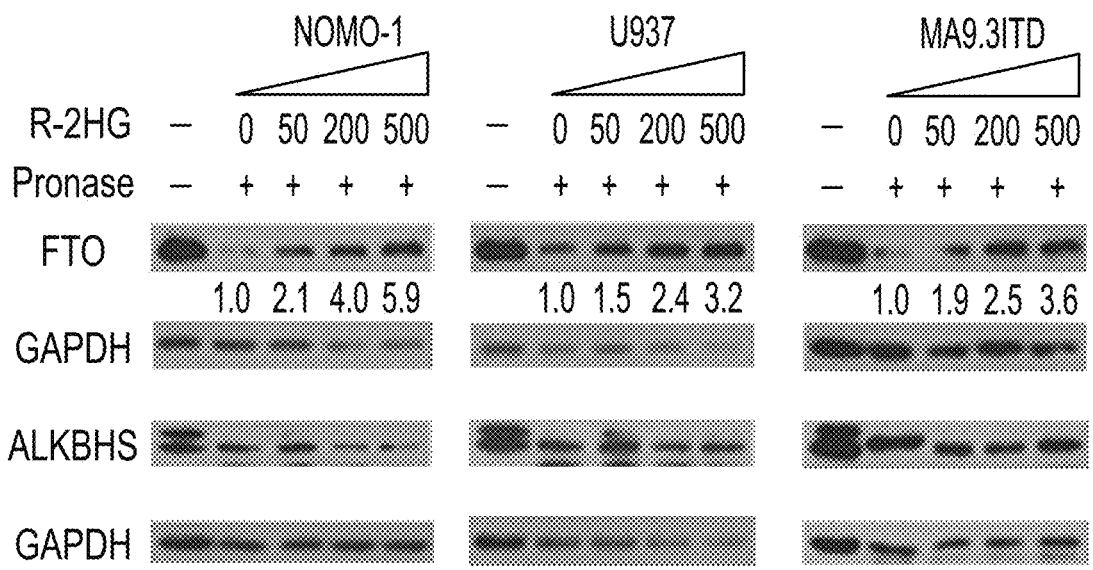
Figure 3E:
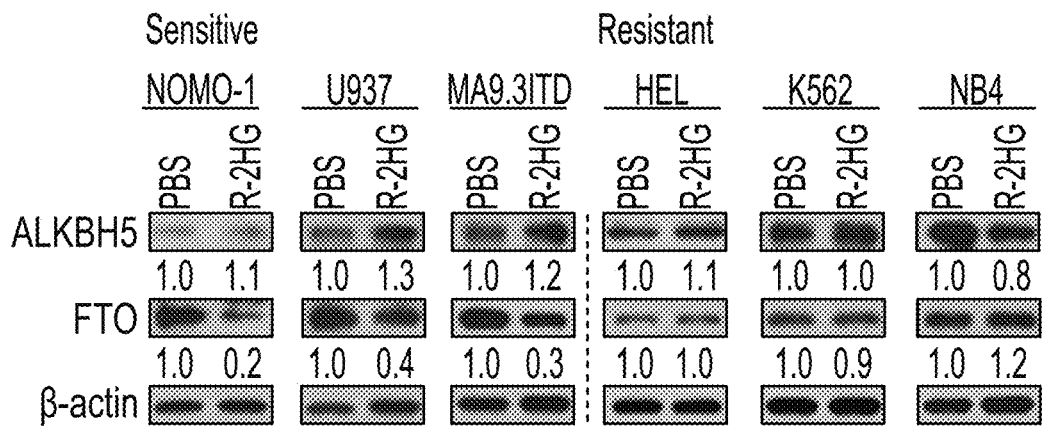
Figure 3F:
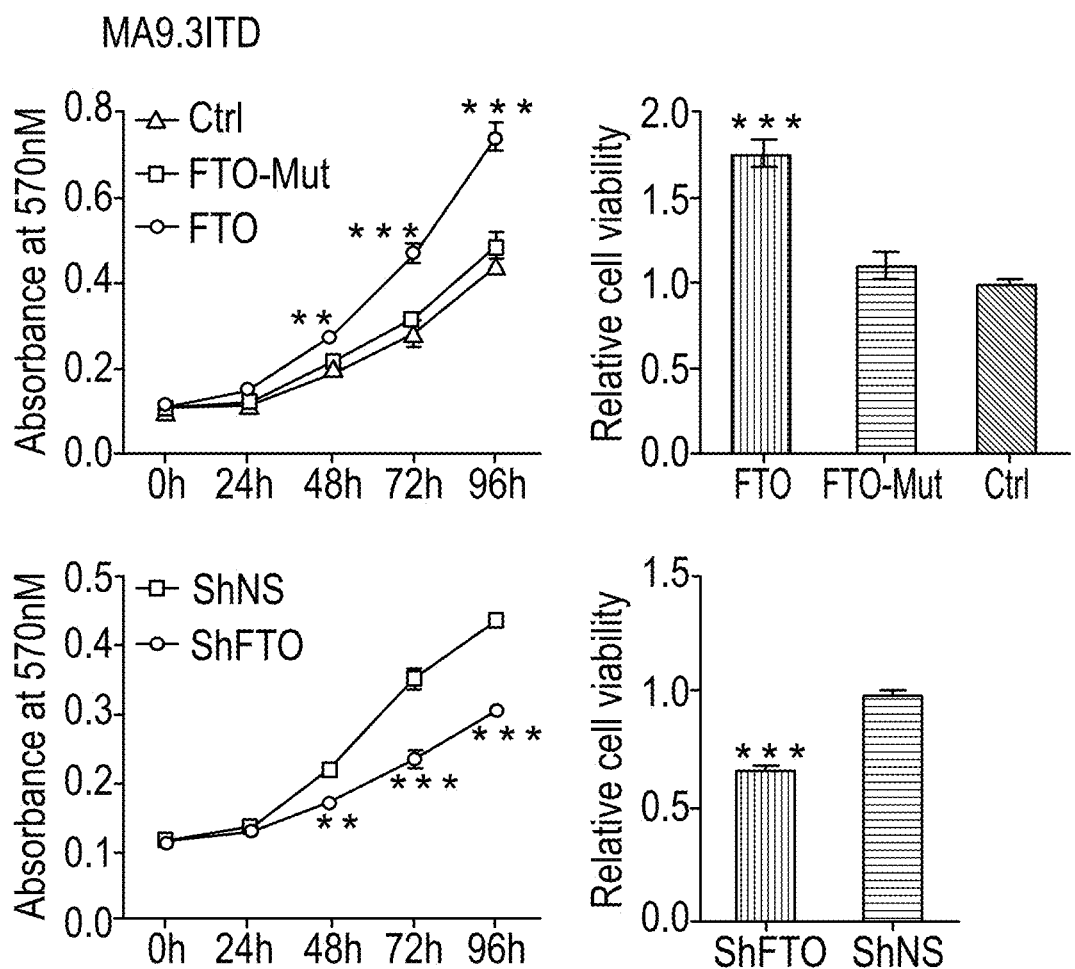

To determine if FTO is a direct target of R-2HG, a drug affinity responsive targets stability (DARTS) analysis[35] was conducted with protein lysates in gradient R-2HG treated samples (FIG. 3C). As expected, the data suggest that R-2HG binds to FTO directly and protects its degradation induced by proteinase in a dose-dependent manner; no such pattern was observed for ALKBH5 (FIG. 3D). Interestingly, consistent with the RNA-seq data (FIG. 2B), our Western blot data also indicate that R-2HG treatment can substantially decrease protein level of FTO, but not ALKBH5, in sensitive leukemic cells, but not in resistant cells (FIG. 3E), though the underlying mechanism warrants further investigation. Thus, R-2HG can not only inhibit FTO activity, but also repress its expression.

Figure 3G:
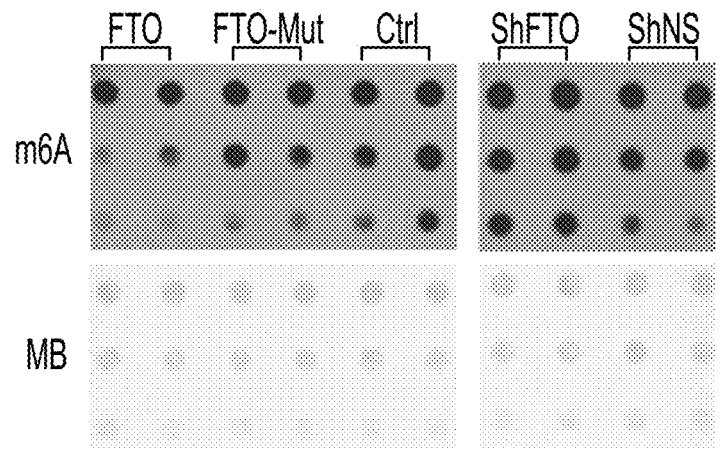
Figure 3H:
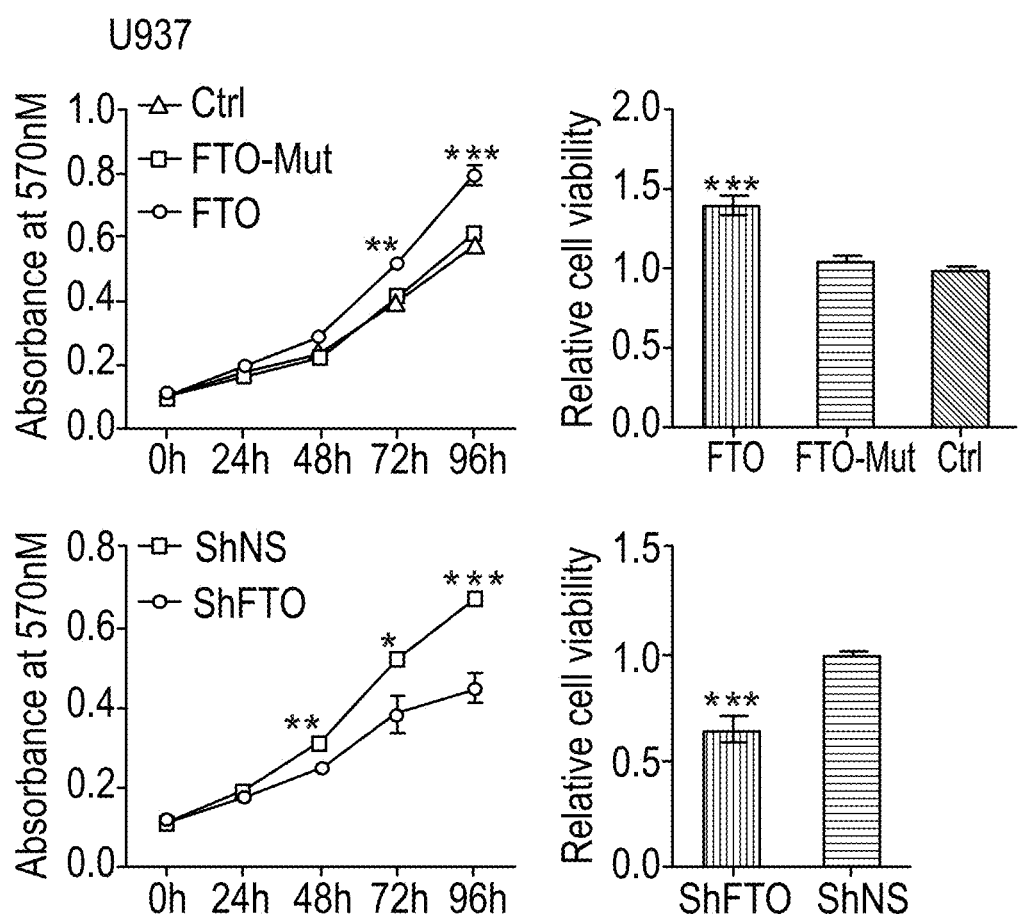
Figure 3I:
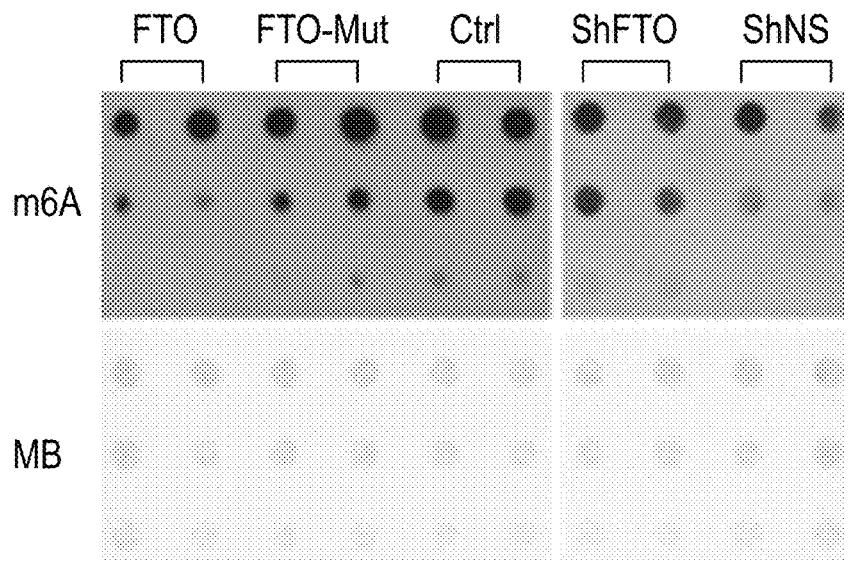
Figure 3J:
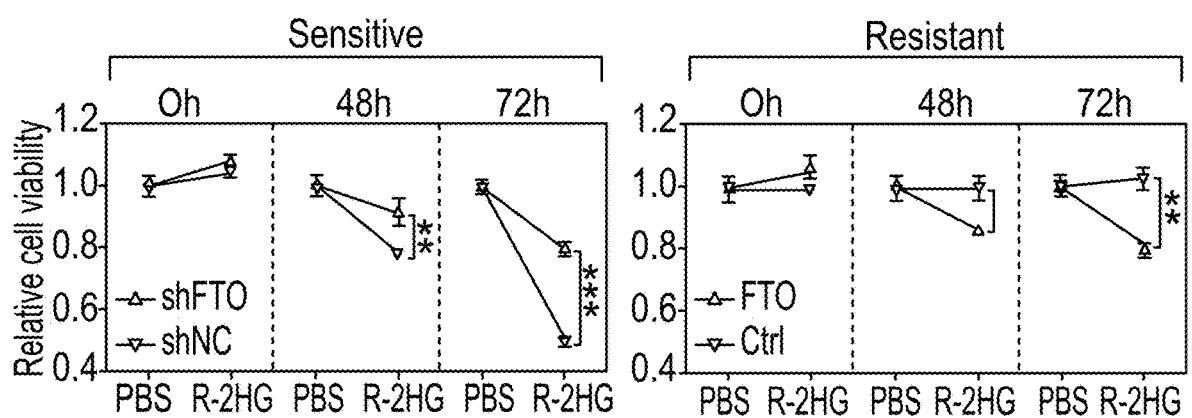
Figure 7E:
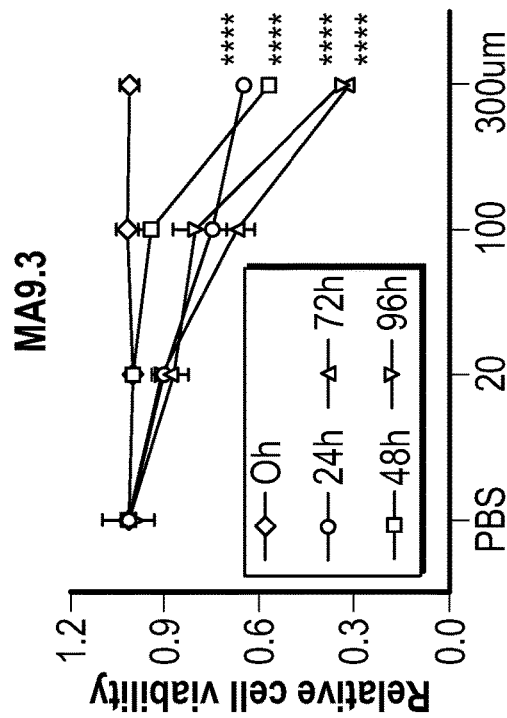
FIGS. 7A-7AA show the effects of R-2HG treatment on cell viability of the 27 leukemia cell lines. Relative cell viabilities of the leukemic cells treated with varying concentrations of R-2HG at varying time points are shown. *, P<0.05; , P<0.01; *, P<0.001; t-test. Specifically, FIG. 7A) depicts the cell viability of NOMO-1, FIG. 7B) U937, FIG. 7C) MA9.3ITD, FIG. 7D) ML-2, FIG. 7E) MONOMAC-6, FIG. 7F) MA9.3, FIG. 7G) THP1, FIG. 7H) MA9.6, FIG. 7I) PL21, FIG. 7J) MA9.6ITD, FIG. 6K) KOPN-1, FIG. 7L) SKNO-1, FIG. 7M) MA9.6RAS, FIG. 7N) MV4-11, FIG. 7O) ME-1, FIG. 7P) KASUMI-1, FIG. 7Q) KOCL69, FIG. 7R) JURKAT, FIG. 7S) KOCL481, FIG. 7T) KOCL50, FIG. 7U) KOCL45, FIG. 7V) MA9.3RAS, FIG. 7W) TF-1, FIG. 7X) HEL, FIG. 7Y) KOCL51, FIG. 7Z) K562, and FIG. 7AA) NB4.
Figure 7F:
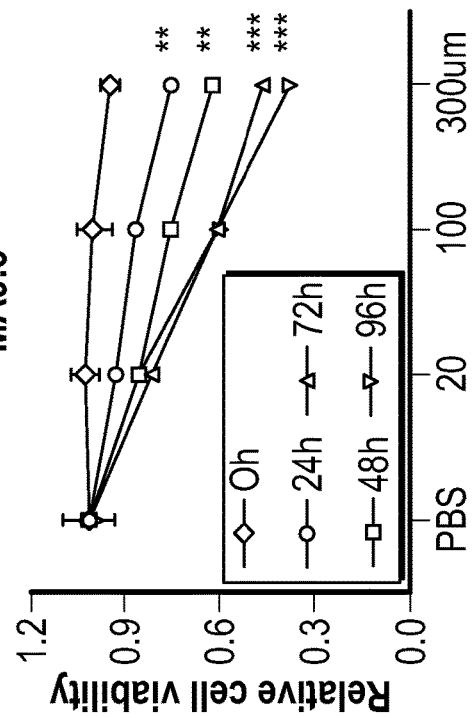
Figure 7G:
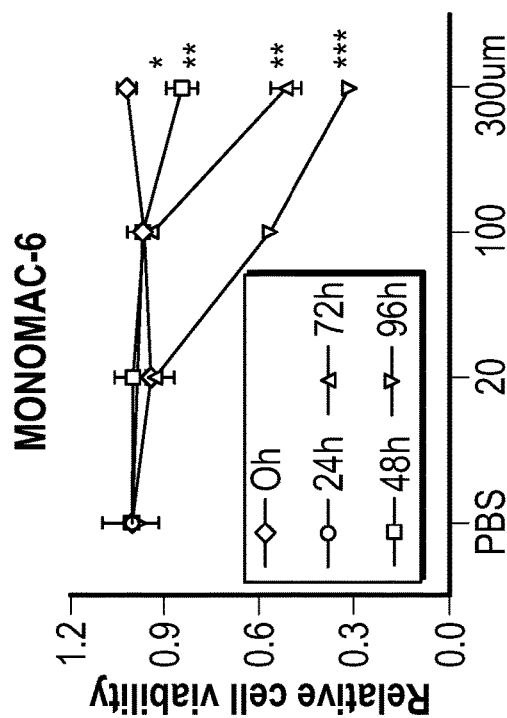
Figure 7H:
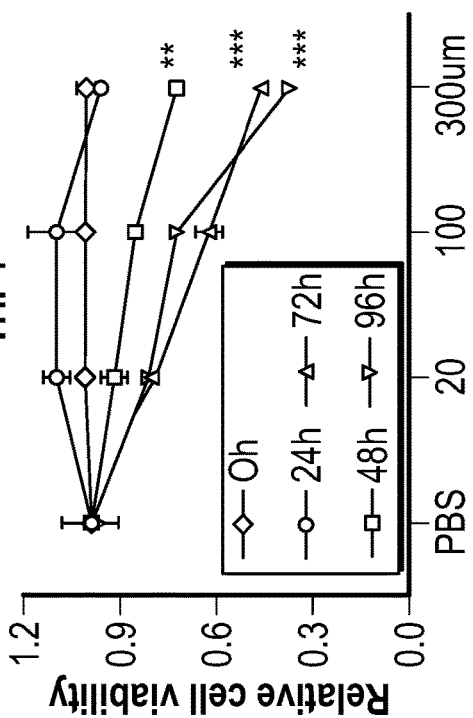
Figure 7Q:
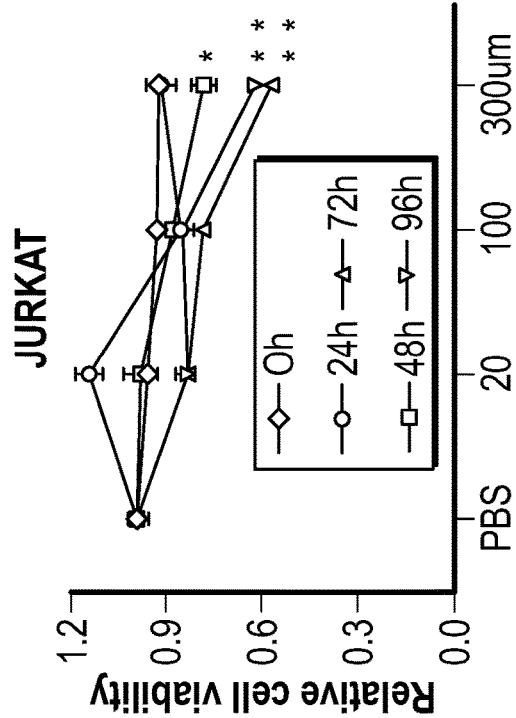
Figure 7R:
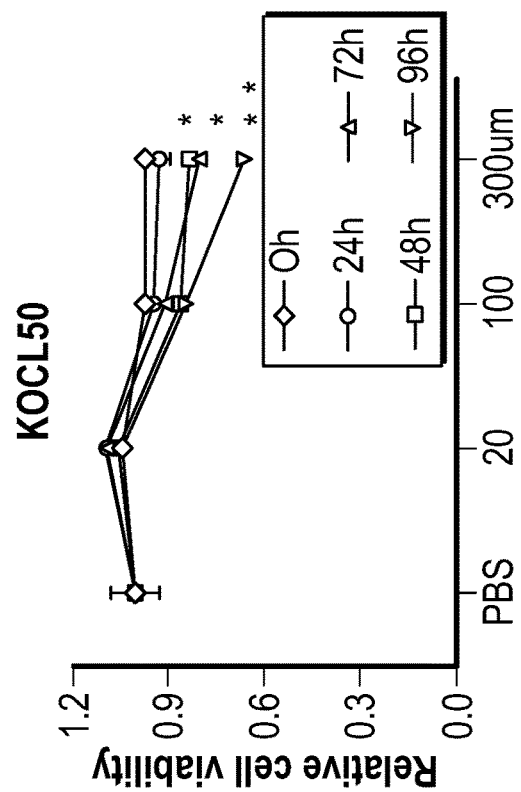
Figure 7S:
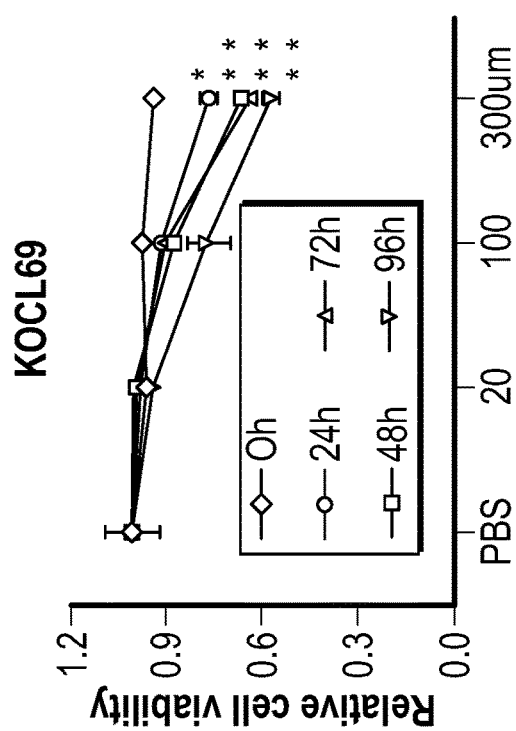
Figure 7T:
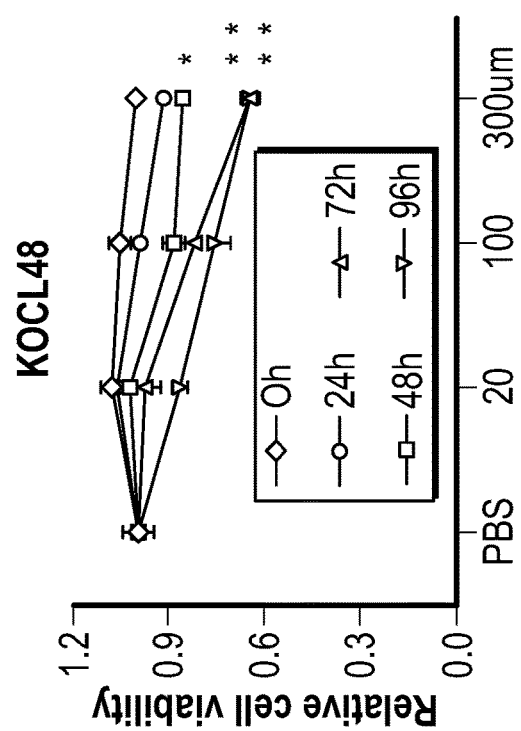
Figure 7T:
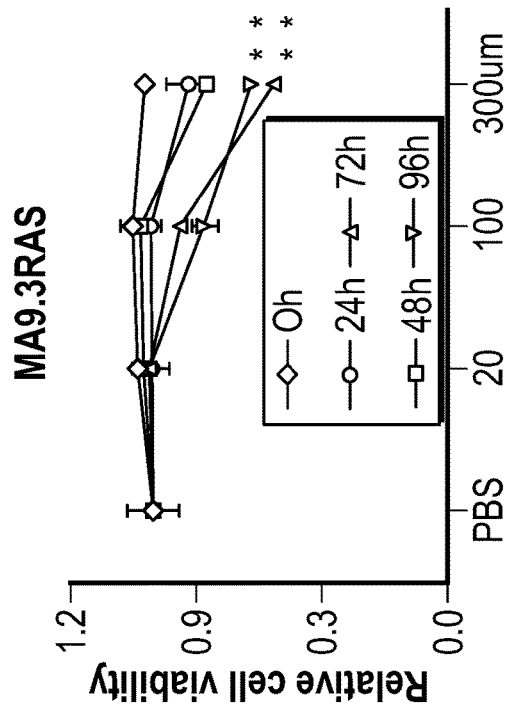
Figure 7V:
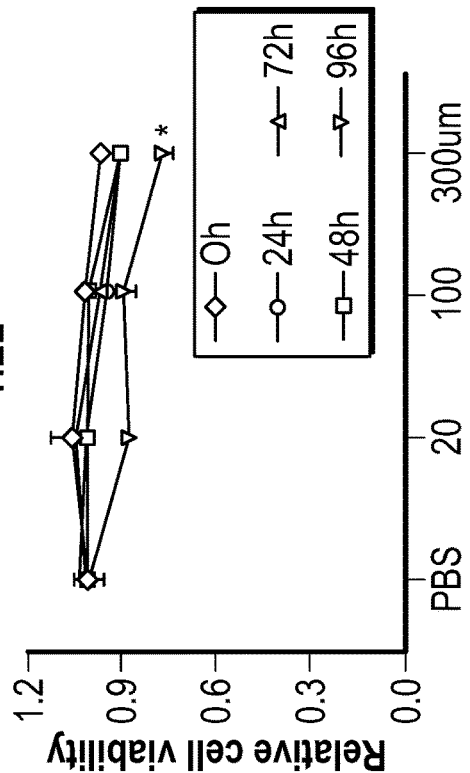
Figure 7U:
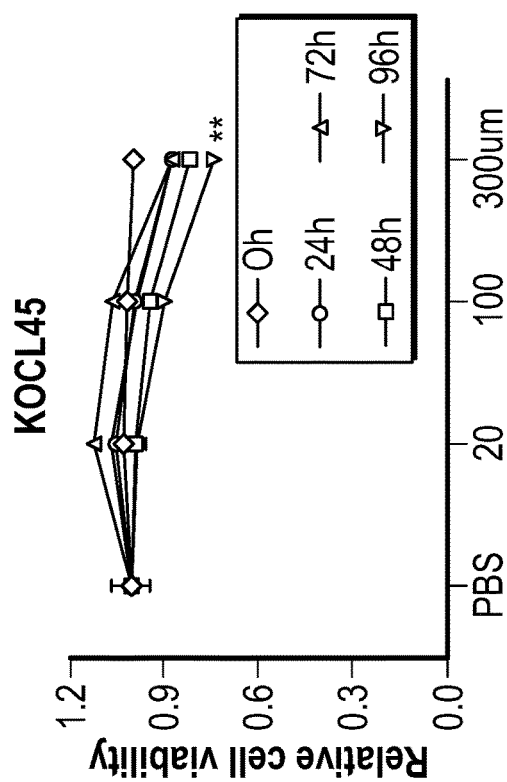
Figure 7W:
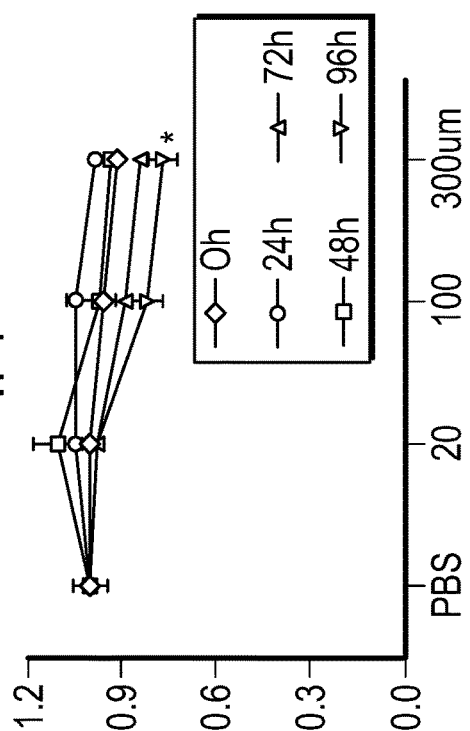
Figure 7Y:
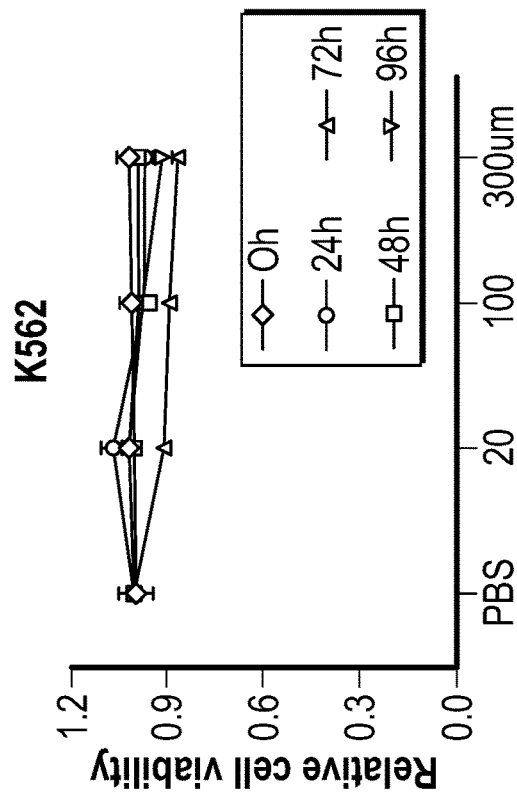
Figure 7Z:
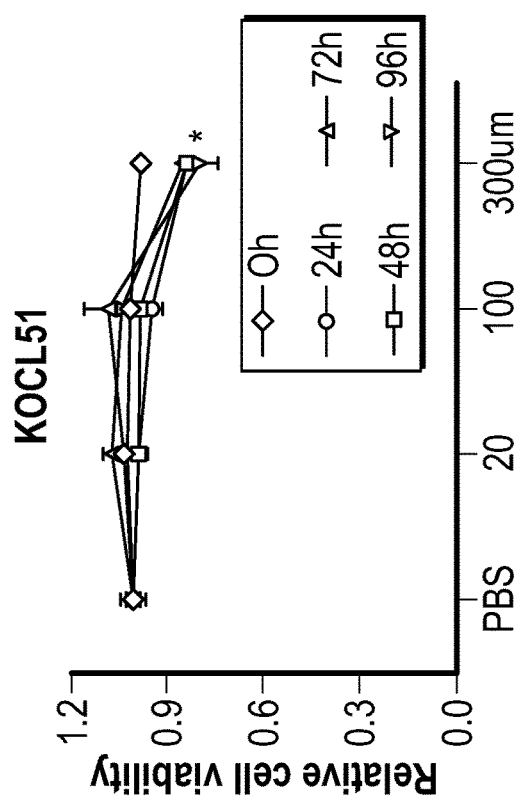
Figure 7A:
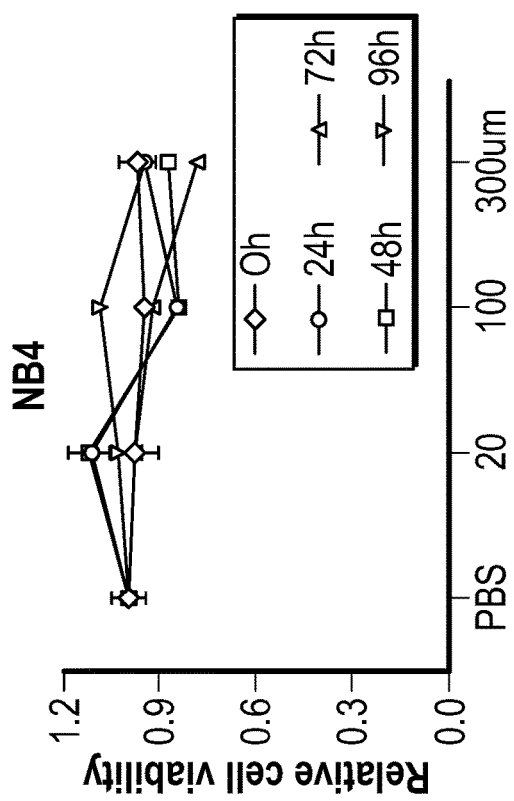

Finally, functional studies show that knockdown of FTO endogenous expression by shRNA in R-2HG-sensitive cells (MA9.3ITD and U927) recapitulated the inhibitory effect of R-2HG on cell growth/viability, associated with increased levels in global $m^6A$ modification (FIGS. 3F-3I vs. FIGS. 1A, 1B, FIG. 3A, FIG. 6A-6AA and FIG. 7A-7AA). Conversely, forced expression of wild-type FTO, but not mutant FTO (carrying two point mutations, H231A and D233A, which disrupt the enzymatic activity of FTO)[33], significantly promoted cell proliferation and viability and deceased global $m^6A$ levels (FIGS. 3G-3I). Moreover, we showed that knockdown of FTO in R-2HG-sensitive leukemic cells significantly reduced the sensitivity to R-2HG; conversely, forced expression of FTO in R-2HG-resistant leukemic cells sensitized the cells to R-2HG (FIG. 3J). Collectively, our data indicate that R-2HG treatment causes FTO down-regulation and loss of function, associated with increased global RNA $m^6A$ modification, which likely are response for R-2HG's anti-leukemic effect.

Example 4

The R-2HG→FTO Axis Regulates MYC Expression

Figure 16A:
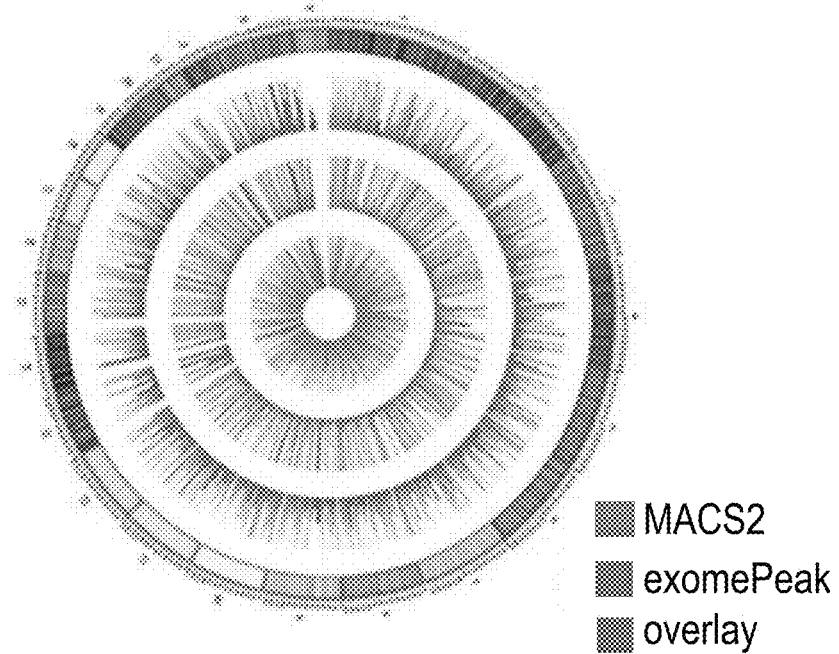
FIG. 16A-FIG. 16I are a transcriptome-wide $m^6A$-seq and analysis of $m^6A$ peaks.
Figure 16B:
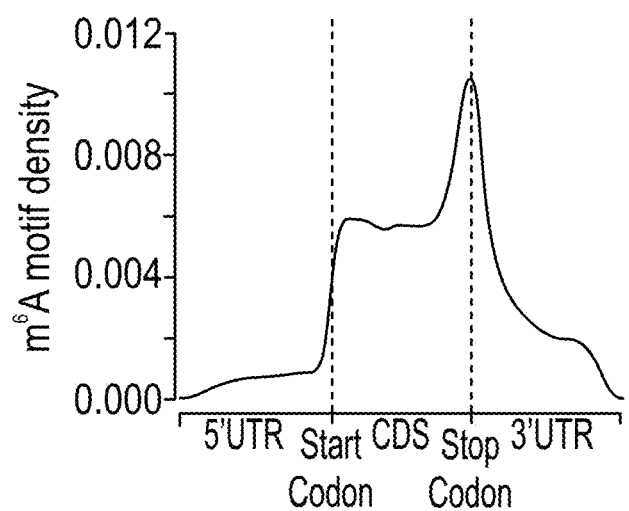
Figure 16C:
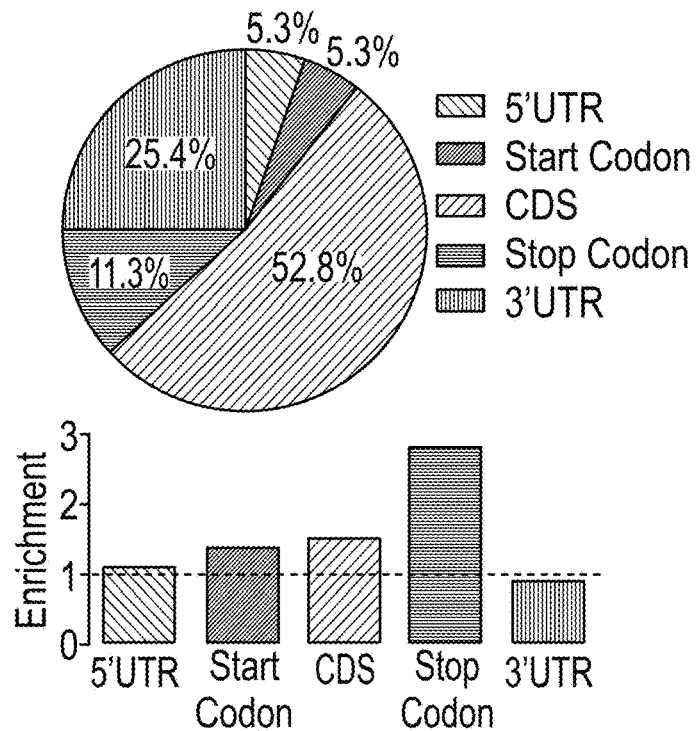
Figure 16D:
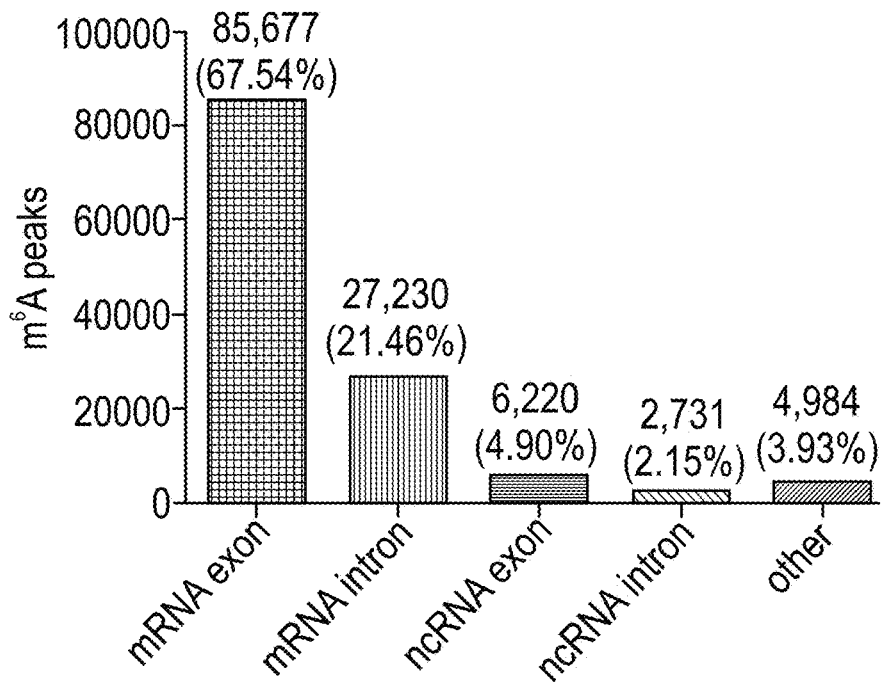
Figure 16E:
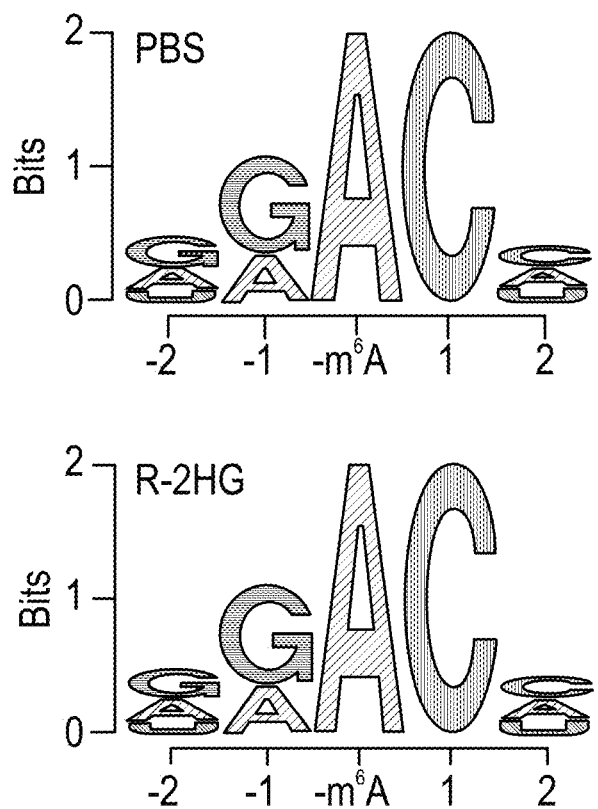
Figure 16F:
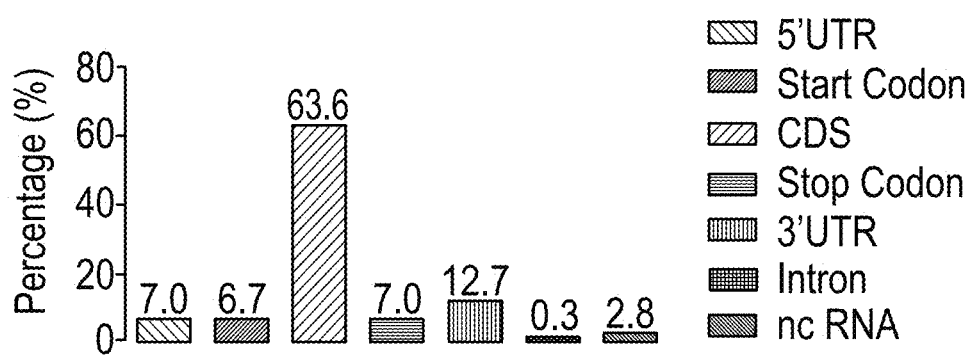
Figure 16G:
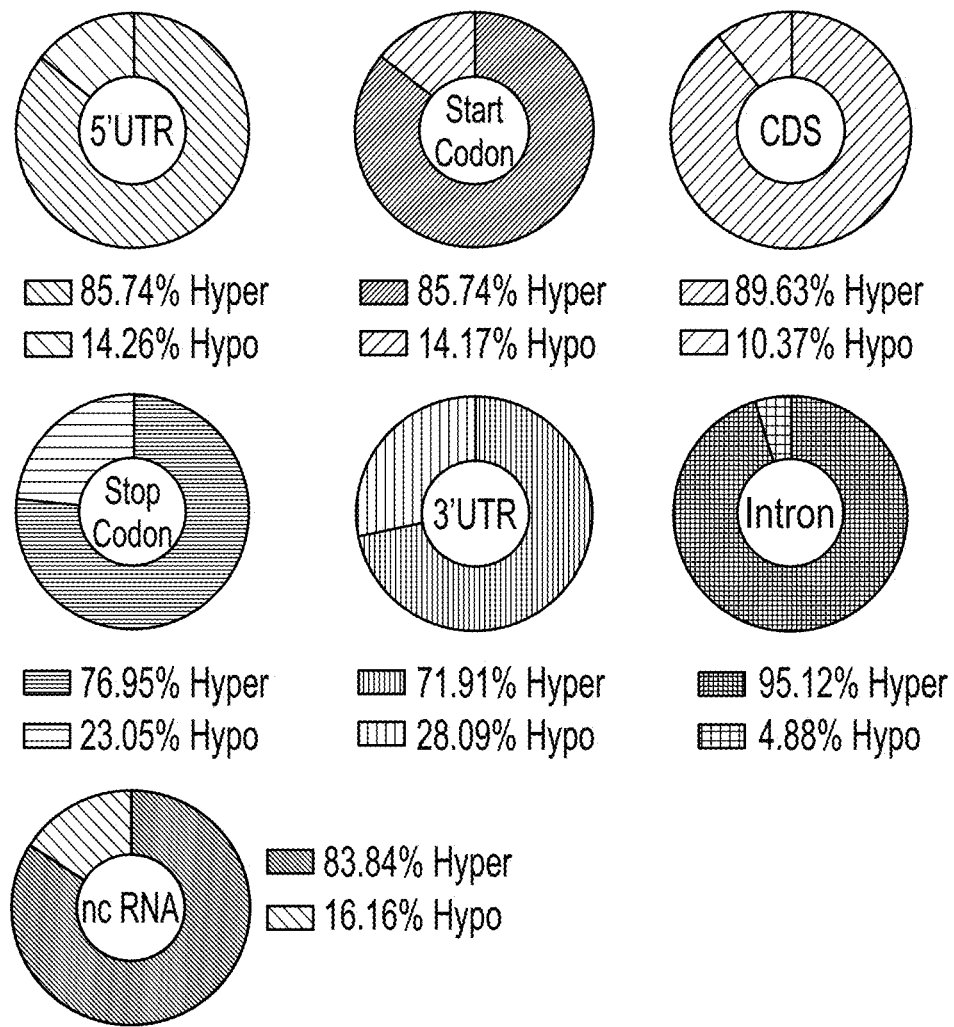
Figure 16H:
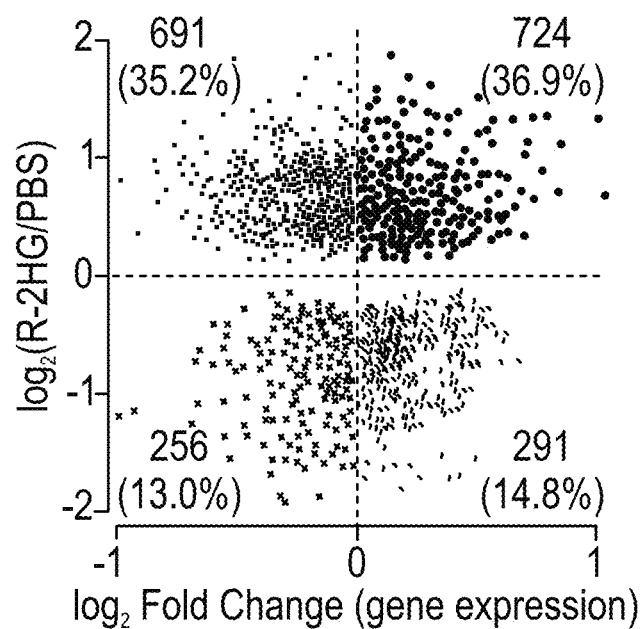

As $m^6A$ modification is the major epigenetic change induced by R-2HG in sensitive leukemic cells (FIG. 3A), transcriptome-wide $m^6A$-sequencing ($m^6A$-seq; FIG. 4A) and RNA-seq of R-2HG- or PBS-treated NOMO-1 cells were undertaken. The genomic distributions of the $m^6A$ peaks and the $m^6A$ motifs identified from the two samples (FIGS. 16A-16E) are consistent with those reported previously[36,37]. Notably, consistent with the $m^6A$ dot blot data (see FIG. 3A), amongst the 1,952 $m^6A$ peaks detected in both samples, the vast majority (1,415; 72.1%) of them exhibited a significant (p<0.01) increase in $m^6A$ abundance in R-2HG-treated cells relative to PBS-treated cells, whereas only 27.9% (547) displayed a decreased pattern (FIGS. 4B and 4C). The transcripts with $m^6A$ level increases were also significantly enriched with target genes of MYC, E2F and G2M signaling (FIG. 4D) and the majority of the hypermethylated m⁶A peaks located in CDS, with a greater ratio (63.6%) than expected by chance (52.8%) (FIGS. 16C, 16F and 16G). Combinational analysis of m⁶A-seq and RNA-seq data shows that dysregulated m⁶A peaks (increased or decreased in abundance) have no obvious trend in the overall transcript level change in R-2HG-treated cells relative to control cells (FIG. 16H).

MYC targets and E2F targets are the top gene sets repressed by R-2HG in sensitive leukemic cells (see FIG. 2B), and they are believed to be regulated directly or indirectly by MYC, a master regulator and universal amplifier of global gene regulation[38,39]. Notably, the m⁶A-seq data from R-2HG- or PBS-treated cells indicates that the MYC transcripts are enriched with m⁶A peaks, and R-2HG treatment causes a considerable increase in the abundance of the m⁶A peaks, especially in the 5'UTR and CDS regions (FIG. 4E), which was confirmed by gene-specific m⁶A qPCR assays (FIG. 4f). As MYC is the top 1 gene whose expression is dramatically repressed by R-2HG in both NOMO-1 and MA9-3ITD leukemic cells (FIGS. 14C and 14D), determination of whether the suppression of MYC expression is related to R-2HG-mediated repression of FTO expression/activity and increase of m⁶A abundance on MYC transcripts was undertaken. First, luciferase reporter and mutagenesis assays were performed with MYC 5'UTR or CDS containing wild-type or mutant m⁶A sites (note: m⁶A was replaced with T in the mutants). As expected, forced expression of wild-type FTO, but not mutant FTO, relative to the control, significantly increased luciferase activity of the reporter construct carrying wild-type MYC 5'UTR or CDS; such increase was abrogated when the putative m⁶A sites were mutated (FIG. 4G). Thus, the data suggest that FTO can promote expression of MYC and such promotion relies on the m⁶A modification on MYC transcripts.

Figure 17A:
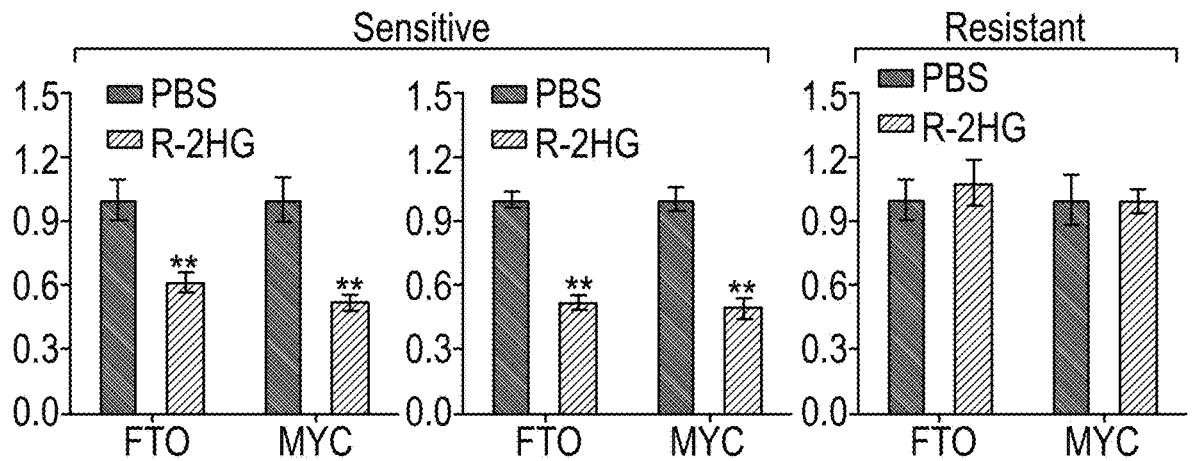
FIG. 17A-FIG. 17D show the effects of R-2HG, FTO and $m^6A$ "reader" YTHDF2 on MYC expression.
Figure 17B:
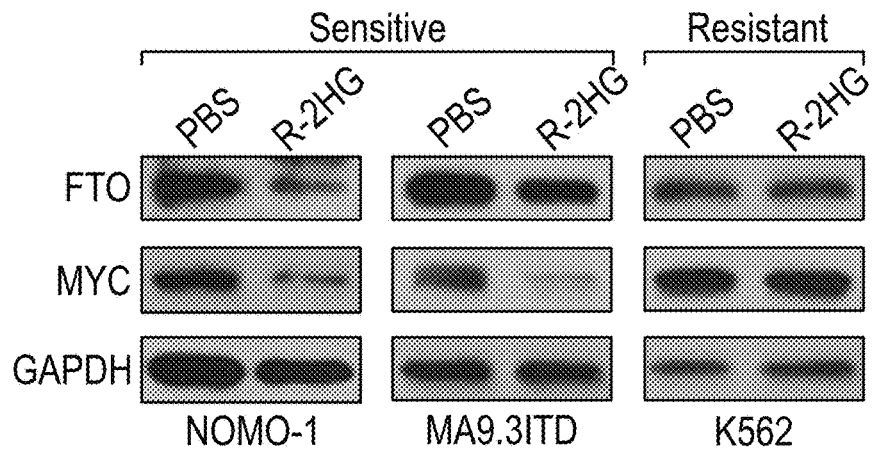
Figure 17C:
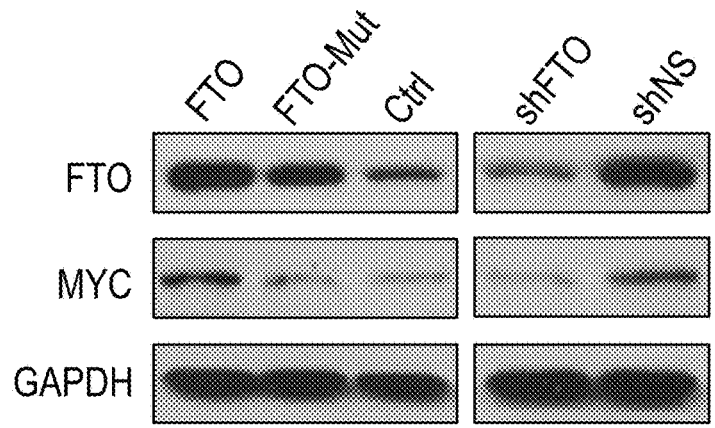

Next, it was shown that R-2HG remarkably suppressed MYC and FTO expression in sensitive cells, but not in resistant cells (FIGS. 17A and 17B). Consistent with the effect of R-2HG, knockdown of FTO also substantially inhibited MYC expression; conversely, compared with forced expression of mutant FTO or empty vector, ectopically expressed wild-type FTO promoted MYC expression (FIG. 17C).

Figure 16I:
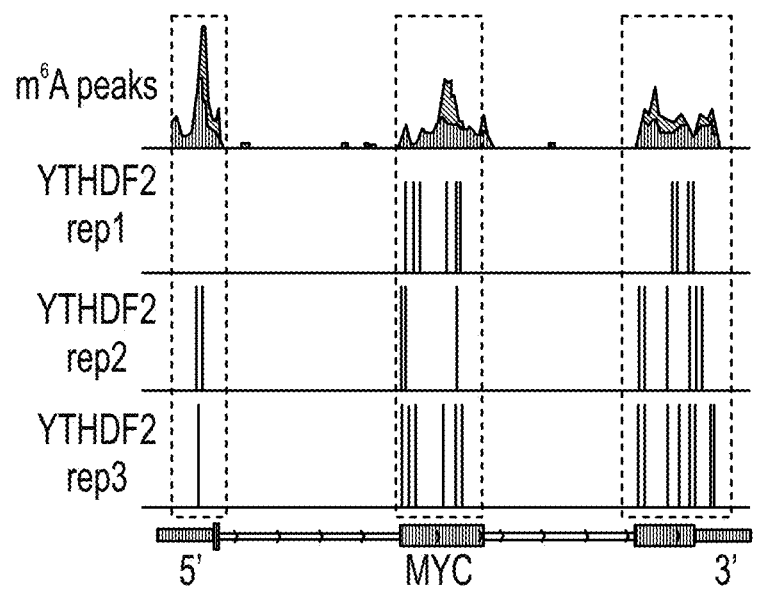
Figure 17D:
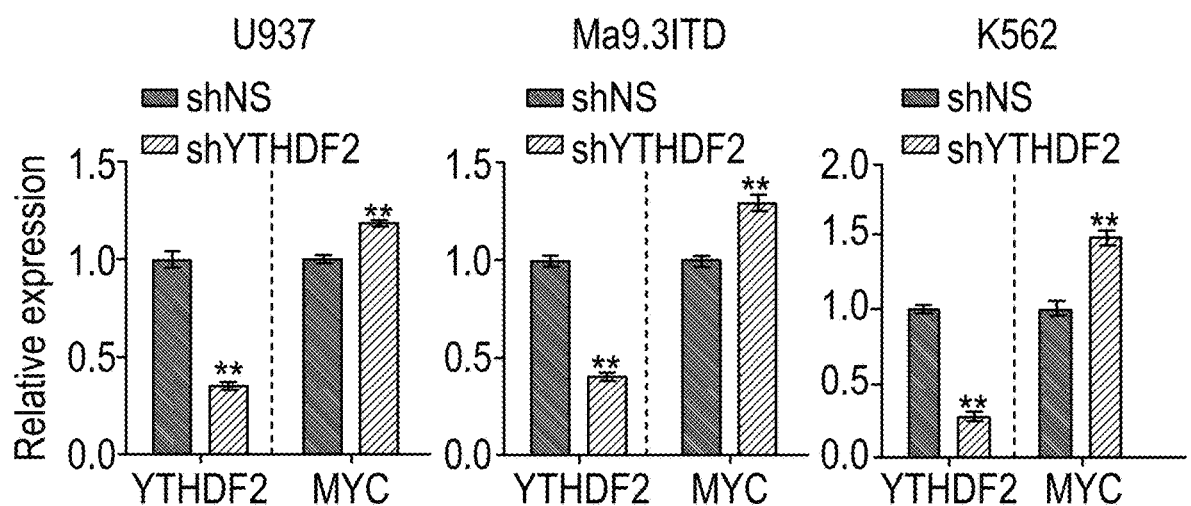

To further elucidate the molecular mechanism by which R-2HG-induced m⁶A modification increase regulates MYC expression, MYC mRNA stability in leukemia cells was assessed with R-2HG treatment or m⁶A reader inhibition. Remarkably, R-2HG dramatically decreased MYC mRNA stability in the sensitive cells (half life: 0.72 hours vs. 1.57 hours), whereas with little effect in resistant cells (FIG. 4H), indicating that R-2HG-induced down-regulation of MYC is likely related to the less stability of MYC transcripts due to increased m⁶A modification. The knockdown of expression of YTHDF2, a major m⁶A reader that is responsible for the decay of m⁶A-modified mRNA transcripts[37] and binds on MYC mRNA (FIG. 16I), noticeably increased stability of MYC transcripts in leukemia cells (FIG. 4I and FIG. 17D), suggesting that the stability of MYC transcripts is at least in part subjected to YTHDF2-mediated RNA decay.

Lastly, m⁶A-seq of R-2HG- and PBS-treated sensitive cells (MA9.3ITD) or resistant cells (MA9.3RAS) with or without FTO knockdown (for sensitive cells) or FTO overexpression (for resistant cells) was performed to further analyze the effects of R-2HG and FTO on m⁶A modification of MYC transcripts. In sensitive cells, R-2HG substantially increased m⁶A abundance at the 5'UTR and CDS regions of MYC transcripts, and such increase can be sufficiently abrogated by FTO knockdown; in contrast, in resistant cells, R-2HG showed no obvious effect on m⁶A abundance on MYC transcripts, whereas forced expression of FTO substantially reduced the m⁶A abundance in PBS-treated cells and such decrease was abrogated by R-2HG treatment, resulting in the substantial increase in m⁶A abundance at the 5'UTR and CDS regions of MYC transcripts in R-2HG treated FTO-overexpressing cells than in PBS-treated ones (FIG. 4J). Collectively, the data uncovers a novel molecular mechanism (i.e., R-2HG⊣FTO⊣m⁶A modification⊣MYC) by which R-2HG inhibits MYC signaling and exerts anti-leukemic effect (FIG. 4K).

Example 5

Figure 5A:
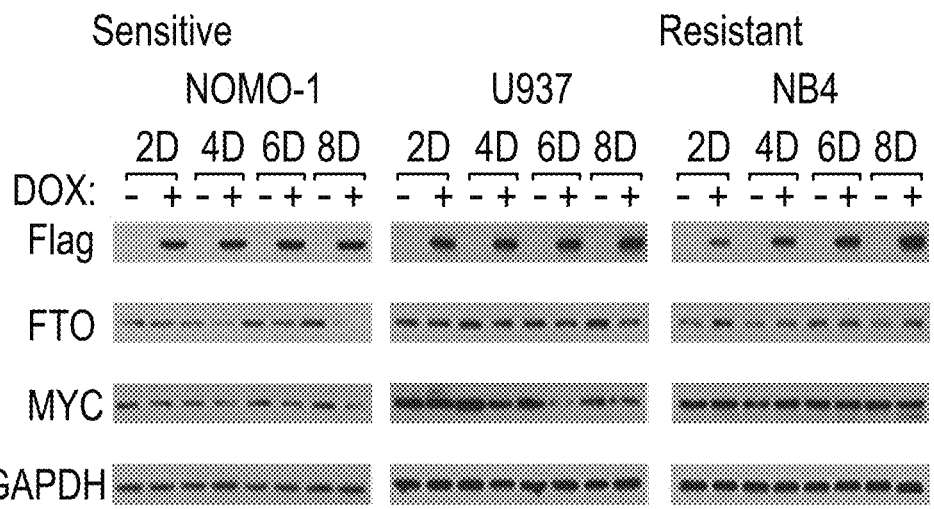
Figure 5B:
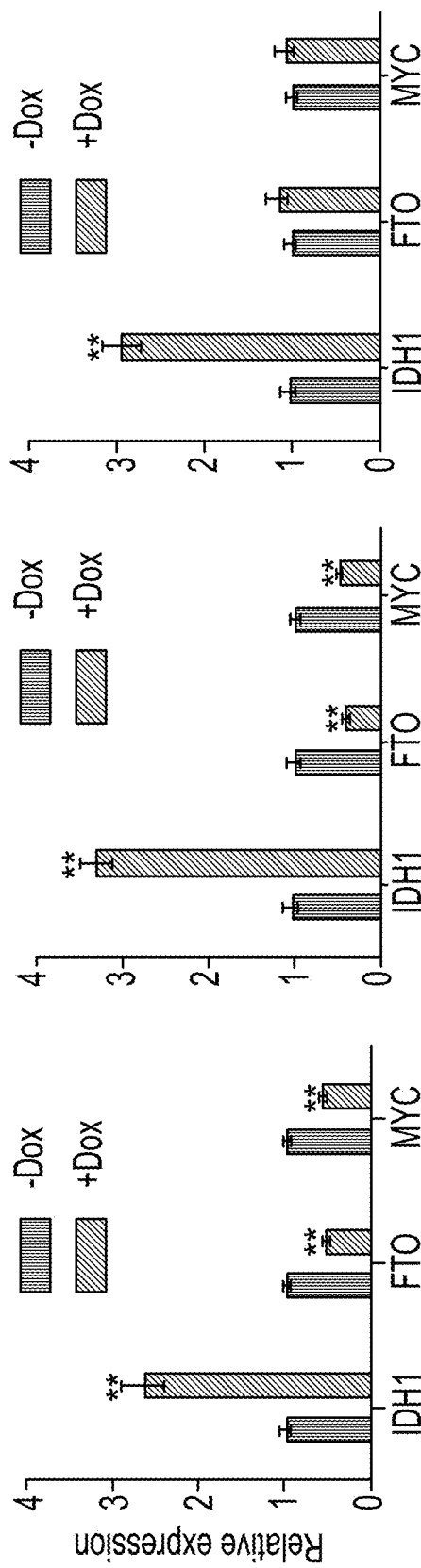
Figure 5C:
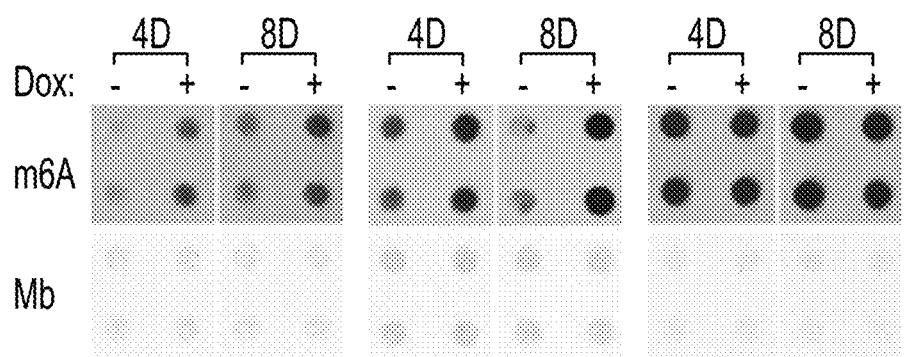
Figure 5F:
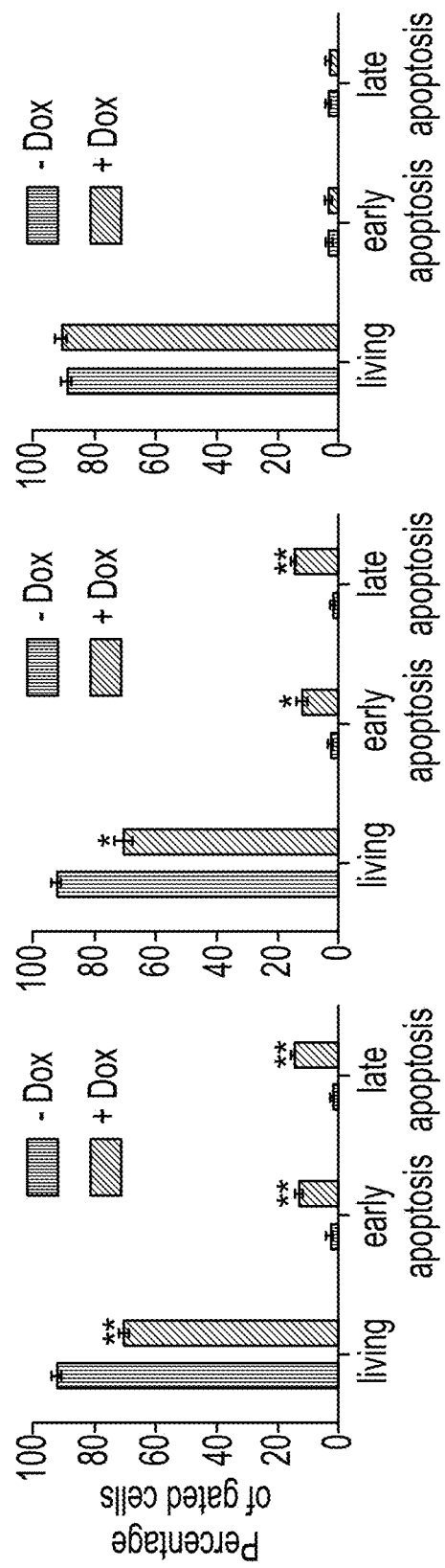
Figure 5G:
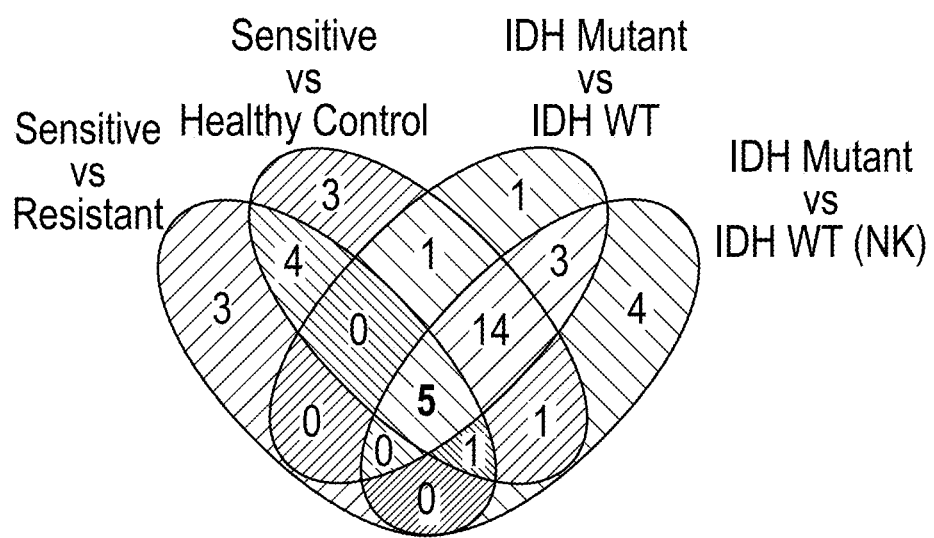

FTO/MYC Homeostasis Controls R-2HG Sensitivity and Pre-Treatment with MYC-Signaling Inhibitors Sensitizes Leukemic Cells to R-2HG Endogenous R-2HG is converted from α-KG by mutant IDH[7,8]. To determine whether mutant IDH can recapitulate the phenotypes observed in R-2HG treated leukemia cells, leukemic cell lines with inducible expression of mutant IDH were created. As expected, doxycycline-induced IDH1$^{R132H}$ expression sufficiently mimicked the phenotypes caused by exogenous R-2HG, such as suppression of FTO and MYC expression (FIGS. 5A and 5B), enhanced m⁶A modification (FIG. 5C), cell cycle arrest (FIG. 5D), decreased cell proliferation/growth (FIG. 5E) and increased cell apoptosis (FIG. 5F) in sensitive leukemic cells (NOMO-1 and U937), but not in resistant cells (NB4).

Figure 5H:
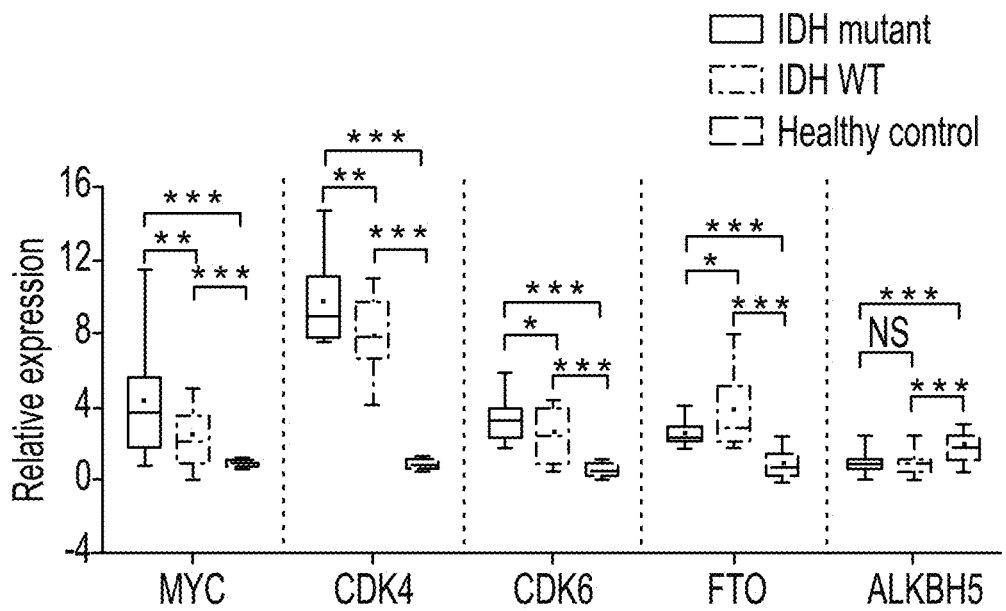
Figure 5I:
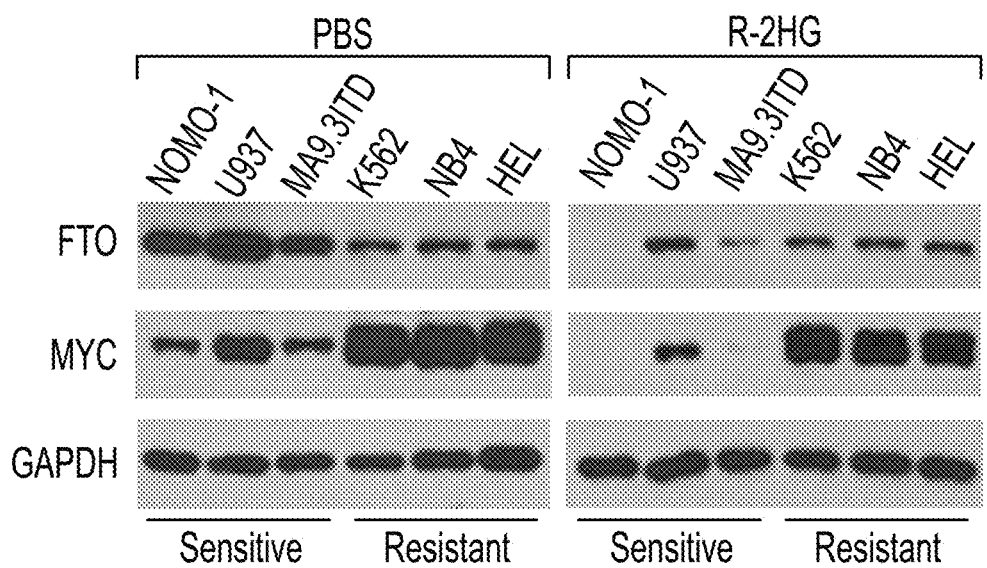
Figure 5J:
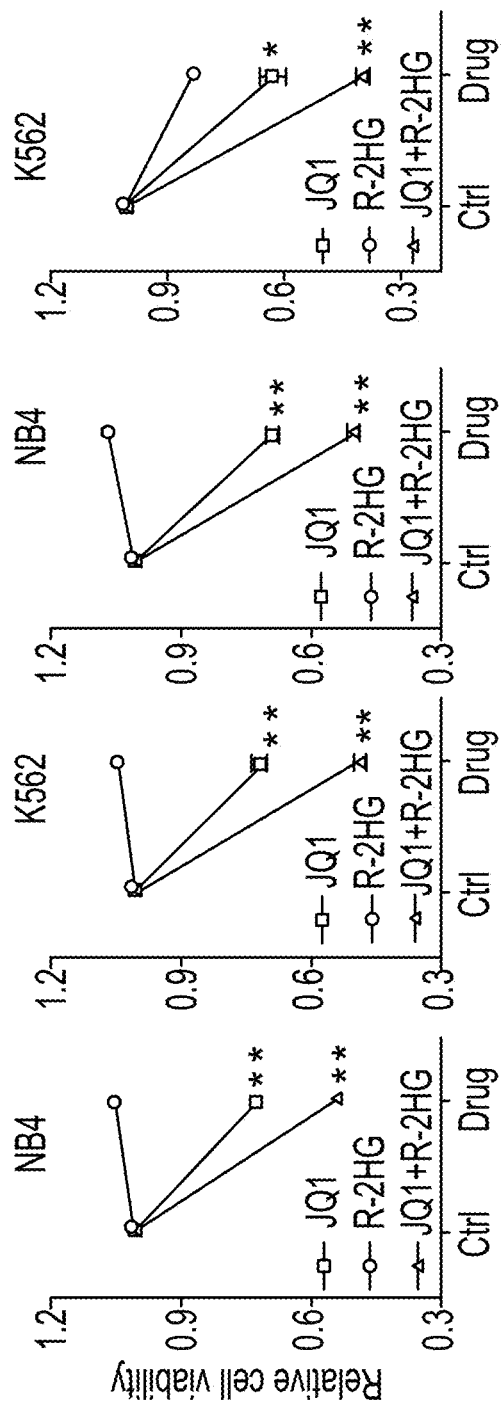
Figure 5K:
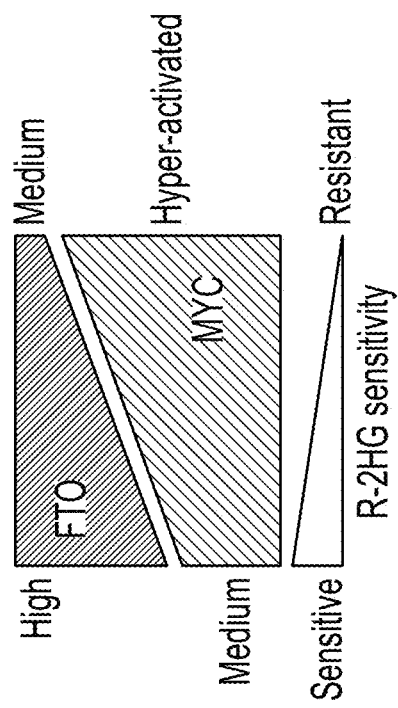
Figure 18A:
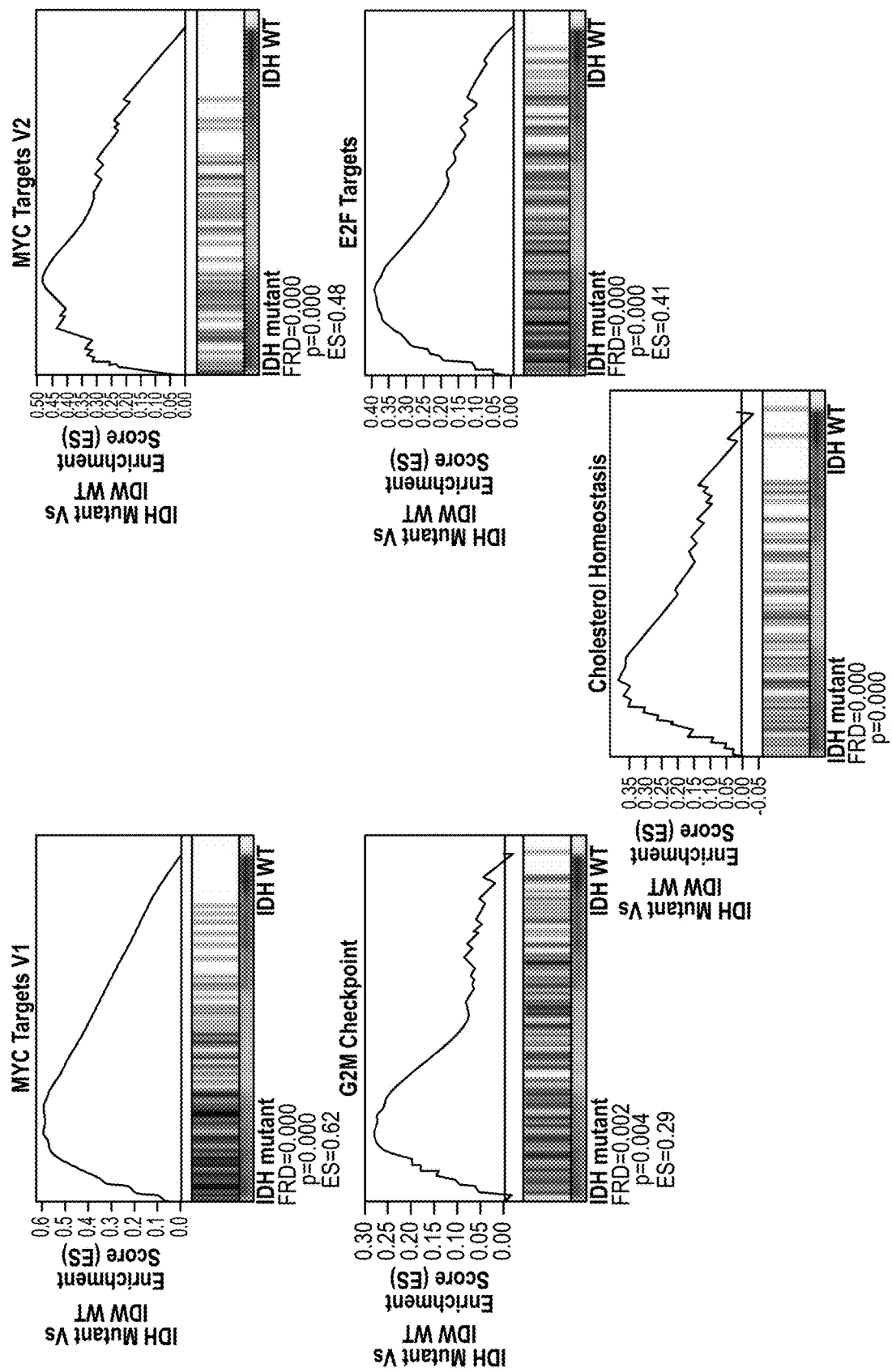
FIG. 18A-FIG. 18F identify the signaling pathways determining sensitivity to R-2HG and the synergistic action between R-2HG and chemotherapy drugs.
Figure 18B:
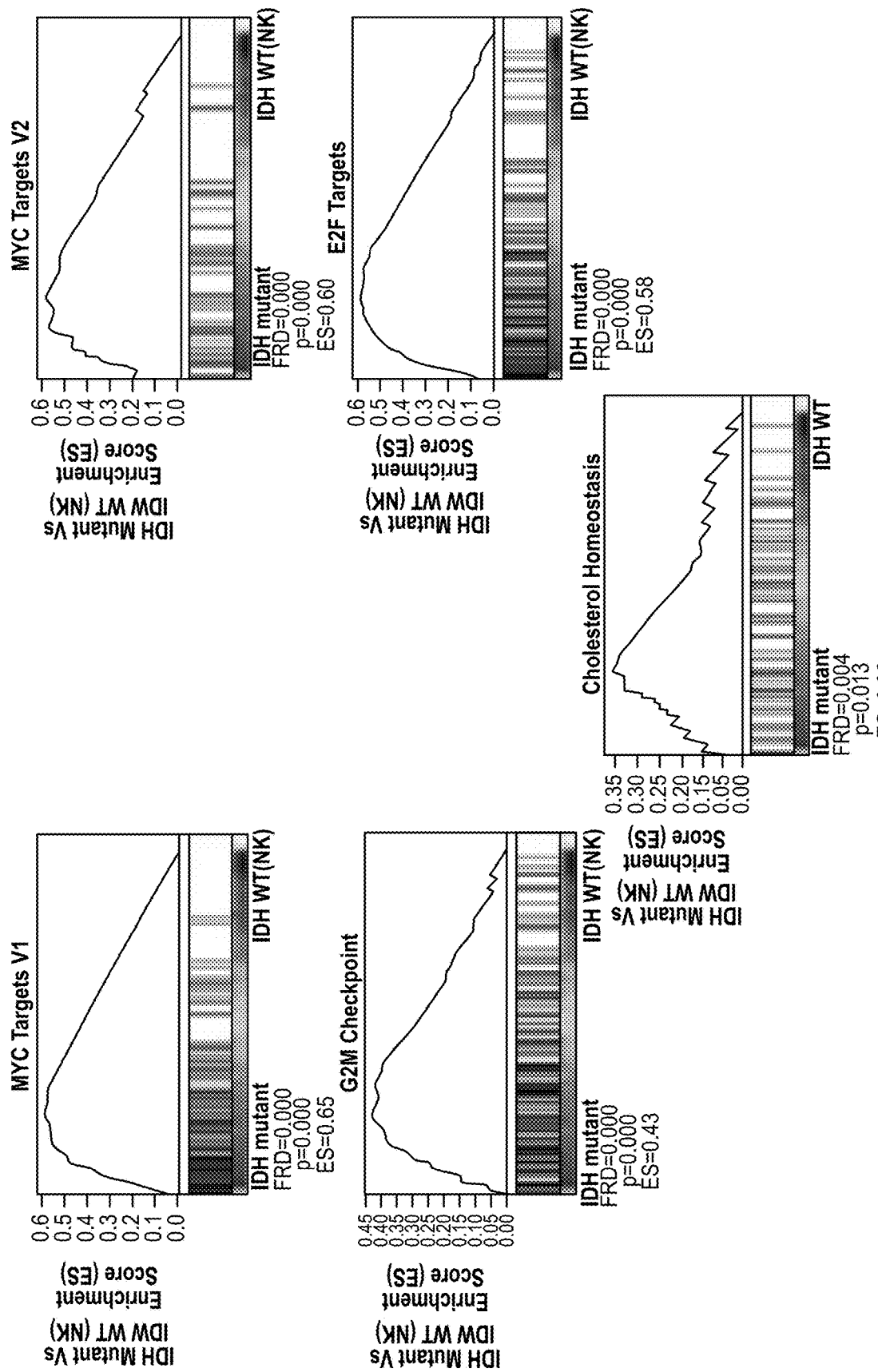
Figure 18C:
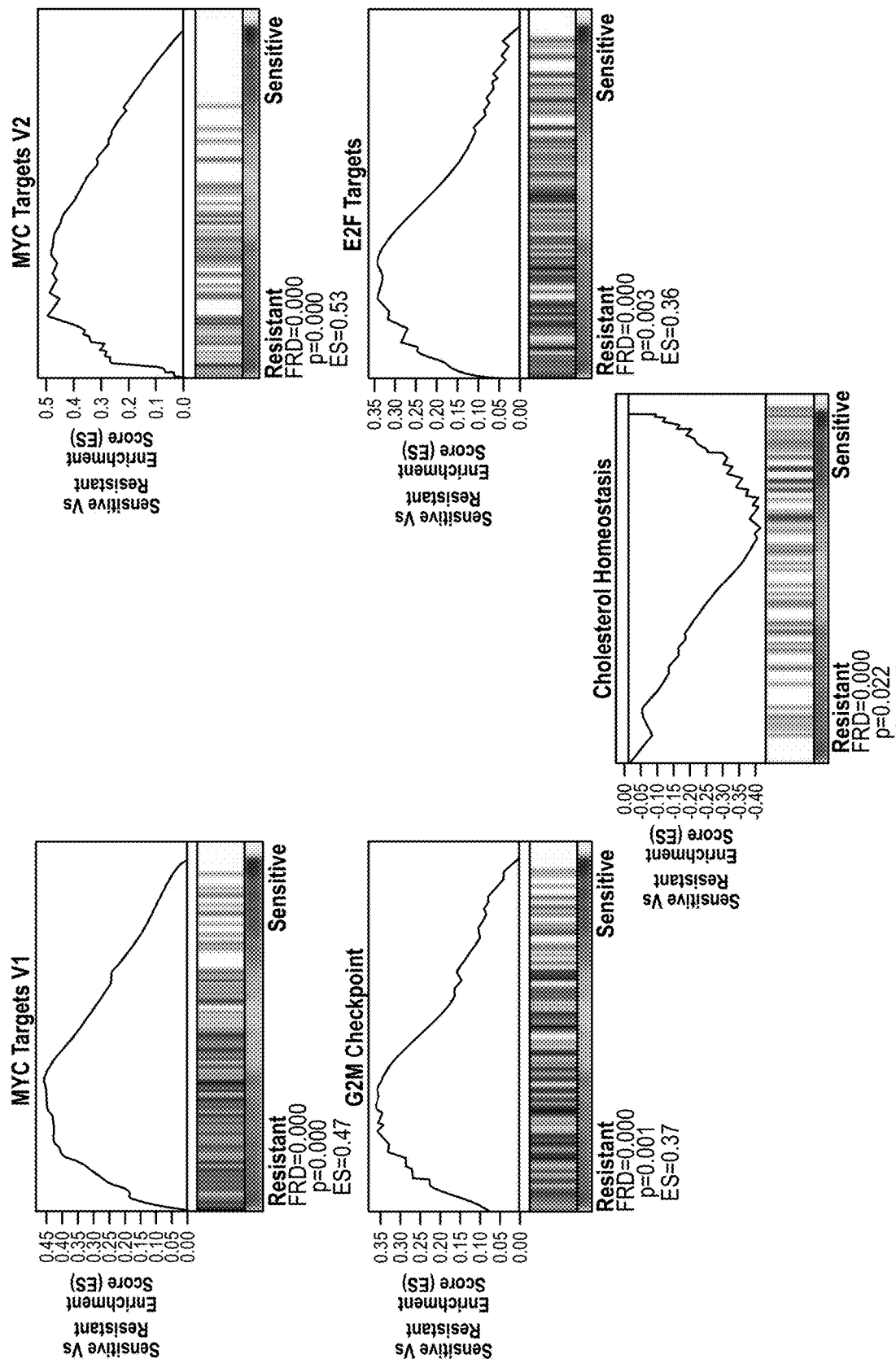
Figure 18D:
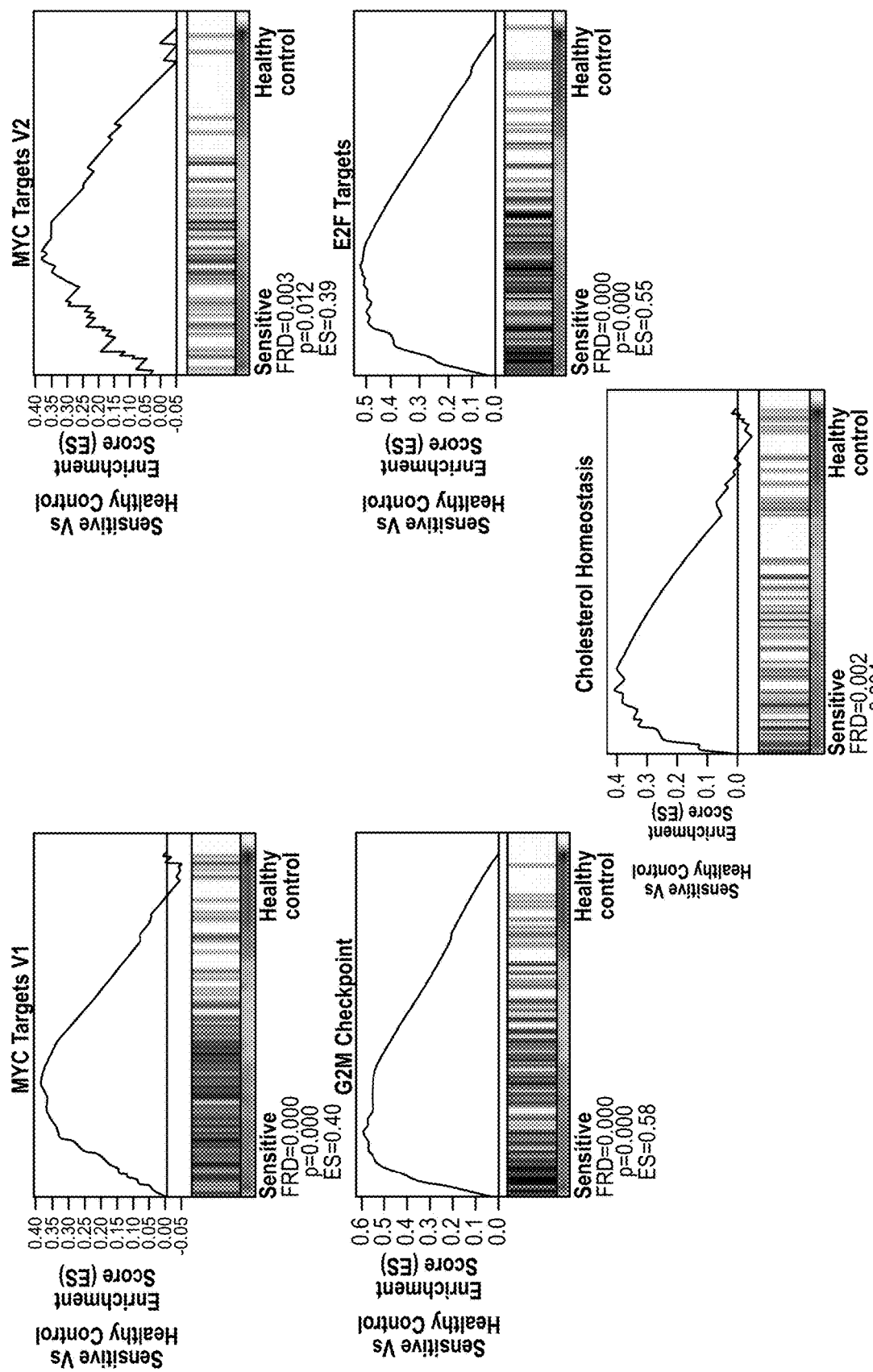
Figure 18E:
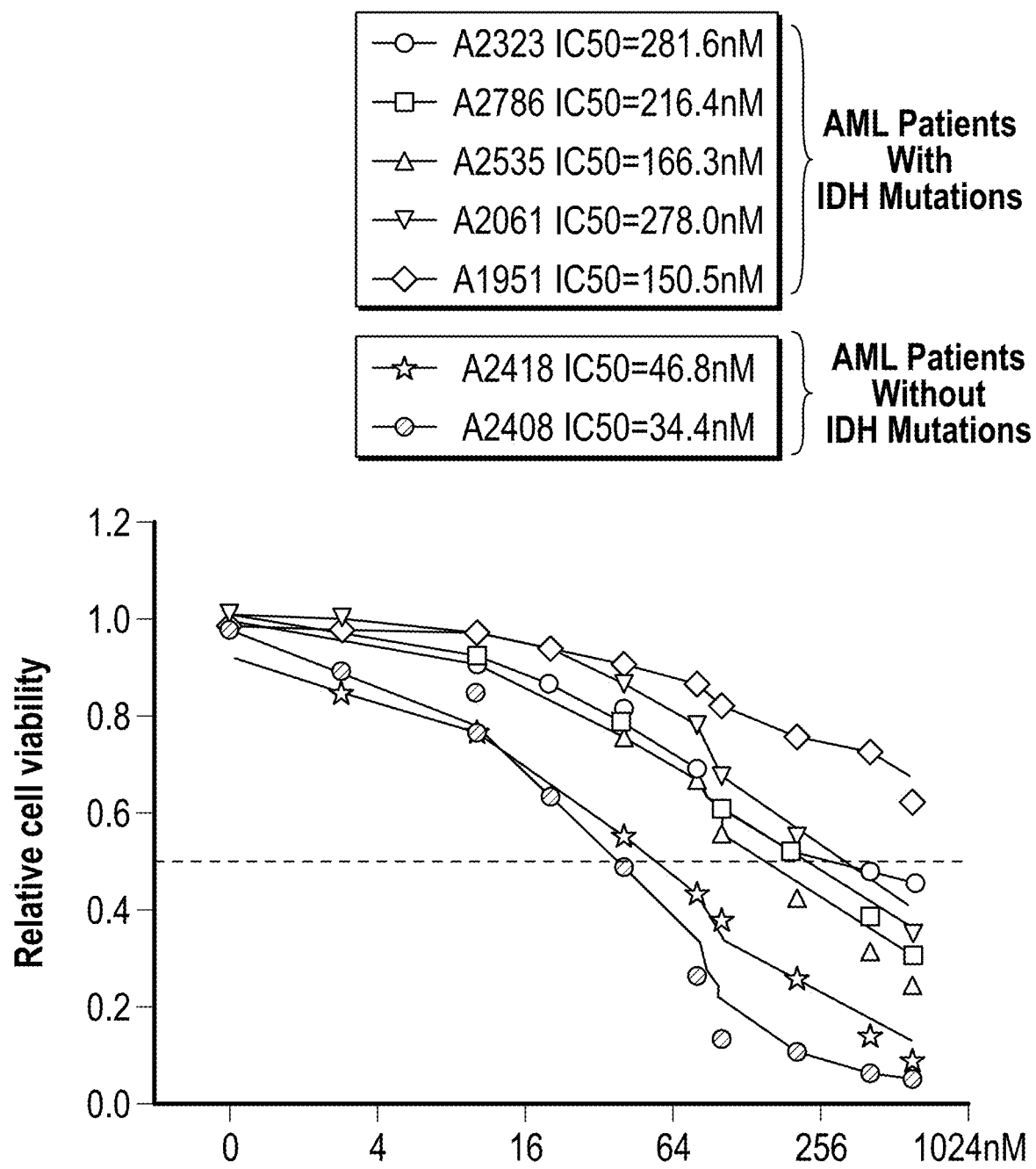

To address the question of why IDH mutations exist in 10-20% of AML cases[17,18], an integrative analysis of the TCGA AML microarray dataset (including 37 IDH-mutant and 160 IDH-wildtype AML patients)[40] with the RNA-seq data shown in FIG. 2A was conducted. Five core signaling pathways enriched in both IDH-mutant AML samples were identified (relative to IDH-wildtype AML samples, in the whole set or in the normal-karyotype subset) and R-2HG-resistant (relative to R-HG-sensitive) leukemic cells (FIG. 5G and FIGS. 18A-18C). Except for cholesterol homeostasis, four pathways (i.e., MYC targets V1, MYC targets V2, G2M checkpoint and E2F targets) were also enriched in sensitive cells compared with healthy controls (FIG. 18D). IDH-mutant AML samples were confirmed to have a higher expression level of MYC and its critical targets, whereas a lower level of FTO (but not ALKBH5) expression, than IDH-wildtype AML samples (FIG. 5H). The Western blot assays also confirmed that R-2HG-resistant leukemic cell lines have a much higher level of MYC while a lower level of FTO than the sensitive cell lines; R-2HG treatment caused a substantial decrease in FTO and MYC expression in the sensitive cell lines, but had only minor effect on their expression in the resistant cell lines (FIG. 5I). Thus, it was presumed that the highly activated MYC signaling diminishes the anti-leukemic effect of R-2HG in IDH-mutant AML cells. To test this, MYC in R-2HG-sensitive leukemic cells were over-expressed and it was found that forced expression of MYC did in fact render the leukemic cells resistant to R-2HG treatment (FIG. 5J). Conversely, pharmaceutical inhibition of MYC signaling by JQ1[24] notably increased sensitivity of R-2HG-resistant leukemic cells to exogenous R-2HG or IDH1$^{R132H}$, and combination of JQ1 and R-2HG exhibited a stronger inhibition on cell viability (FIG. 5K). Primary AML cells with IDH mutations are also sensitive to JQ1 treatment, often with an $IC_{50}$ lower than 1 µM, though with a higher $IC_{50}$ than do AML cells with wild-type IDH (FIG. 18E), likely due to the hyper-activation of MYC signaling in the former. Taken together, the data suggest that high abundance of FTO confers R-2HG sensitivity in leukemic cells, whereas hyper-activation of MYC renders leukemic cells resistant to R-2HG. Exemplary MYC pathway inhibitors are set forth in Table 4.

TABLE 4

Small molecules known to inhibit MYC signaling

| Compound name | Class | Target | References |
|---|---|---|---|
| Flavopiridol | CDK inhibitor | Cdk-9 | Chen et al. 2005; Rahl et al. 2010 |
| Purvalanol A | CDK inhibitor | Cdk-1 | Goga et al. 2007 |
| SU9516 | CDK inhibitor | Cdk-2, Cdk-9 | Gao et al. 2006 |
| PHA 767491 HCI | CDK inhibitor | Cdc-7 and Cdk-9 | Montagnoli et al. 2008; Natoni et al. 2011 |
| SNS-032 | CDK inhibitor | Cdk-2, Cdk-7, and Cdk-9 | Walsby et al. 2011 |
| JQ1 | BET bromodomain inhibitor | Brd-4, Brd-3, Brd-2 | Filippakopoulos et al. 2010; Delmore et al. 2011 |
| SGI-1776 | PIM kinase inhibitor | Pim-1 | Zippo et al. 2007, 2009 |
| EPZ004777 | Dot1 L inhibitor | Dot1 L | Daigle et al. 2011 |
| C464 | p300/CBP ACTfrase inhibitor | p300 | McMahon et al. 1998 |
| SAHA | HDAC inhibitor | | |
| Triptolide | TFIIH/XPB | XPB | Titov et al. 2011 |
| Nutlin-3a | p53-MDM2 inhibitor | p53-MDM-2 | Felsher et al. 2000 |
| SB220025 | MAPK inhibitor | p38 | Zhu et al. 2008 |
| LY294002 | PI3K inhibitor | PI3K | Zhu et al. 2008; Liu et al. 2011; Muellner et al. 2011 |
| VAV-939 | Wnt inhibitor | Tankyrase 1, 2 | He et al. 1998 |
| LY-411575 | γ-Secratase inhibitor | Notch 1 | Moellering et al. 2009 |
| VX-680 | Aurora kinase inhibitor | Aurora kinases | Yang et al. 2011 |
| NSC71948 | BAG1 inhibitor | BAG-1 | Zhang et al. 2011 |
| ABT263 | BCL2 inhibitor | BCL-2 | Zhang et al. 2011 |
| VER-155008 | HSP70 inhibitor | Hsp70/Hsc70 | Zhang et al. 2011 |
| KW-2478 | HSP90 inhibitor | Hsp90 | Nakashima et al. 2010 |
| SB 218078 | Chk1 inhibitor | Hck-1 | Jiang et al. 2011 |
| Leflunomide | DHODH inhibitor | DHODH | White et al. 2011 |

Example 6

R-2HG Sensitizes Leukemia and Glioma to Chemotherapies

Figure 18F:
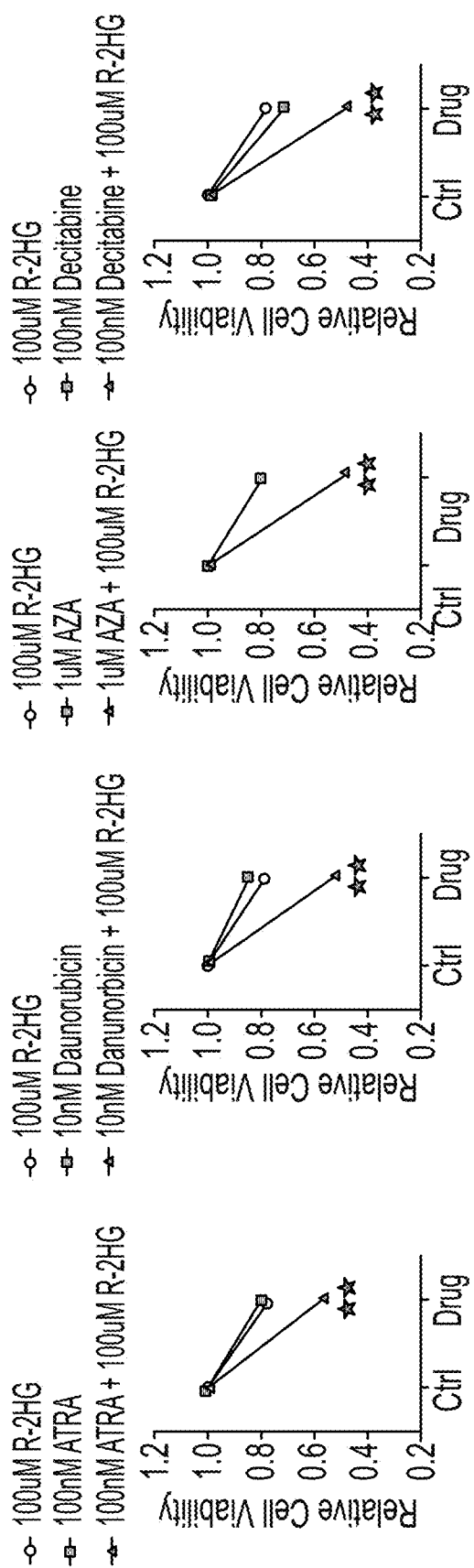

Interestingly, R-2HG also exhibits a synergistic, or at least additive, effect with a series of first-line chemotherapy drugs such as all-trans retinoic acid (ATRA), Azacitidine (AZA), Decitabine, and Daunorubicin (FIG. 18F), though the underlying molecular mechanisms need to be for fully delineated. Thus, R-2HG can be readily administered in combination with such therapeutic agents to treat leukemia in clinic.

Figure 19A:
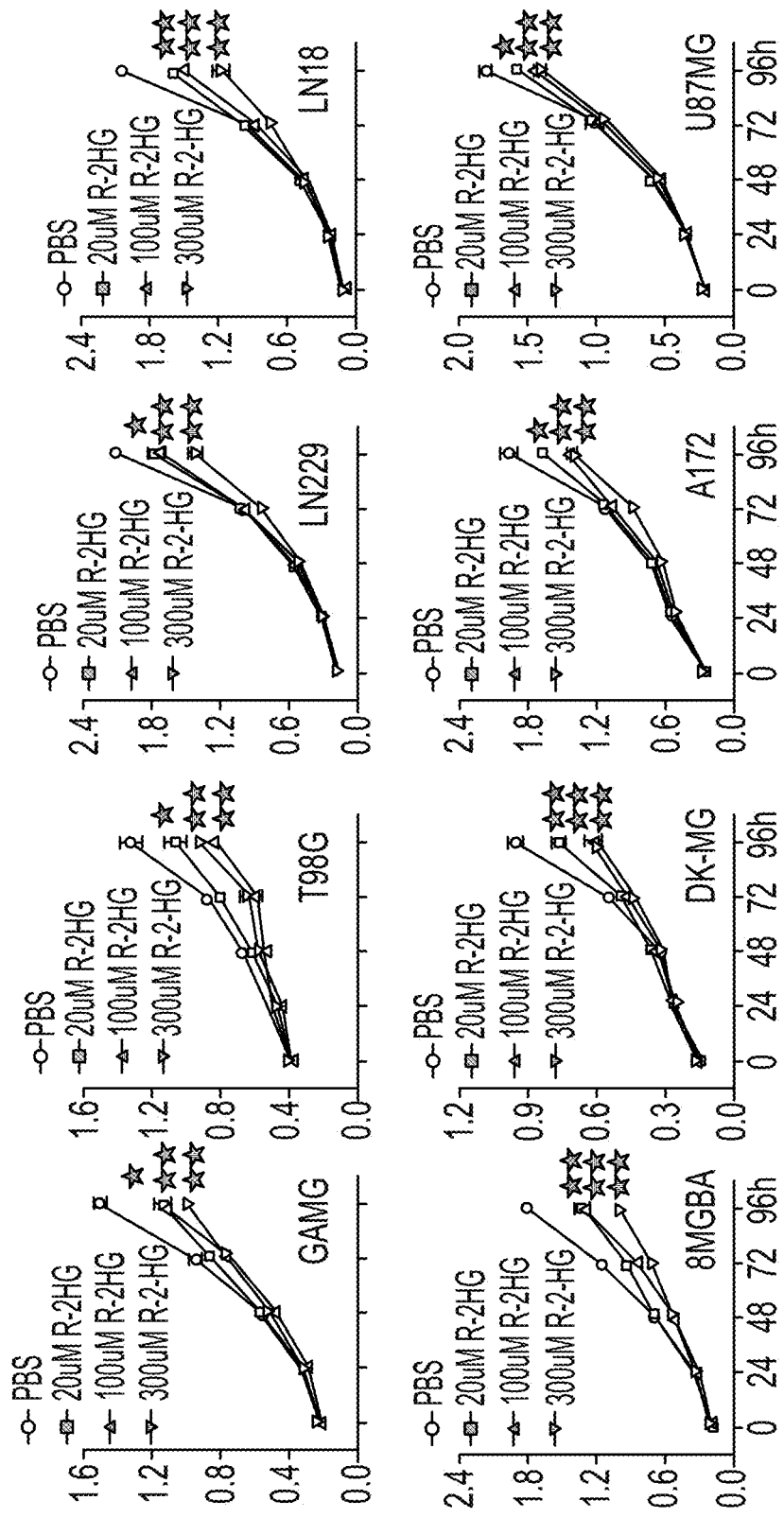
FIG. 19A-FIG. 19C evidence demonstrating the antitumor effects of R-2HG on brain tumor cells.
Figure 19B:
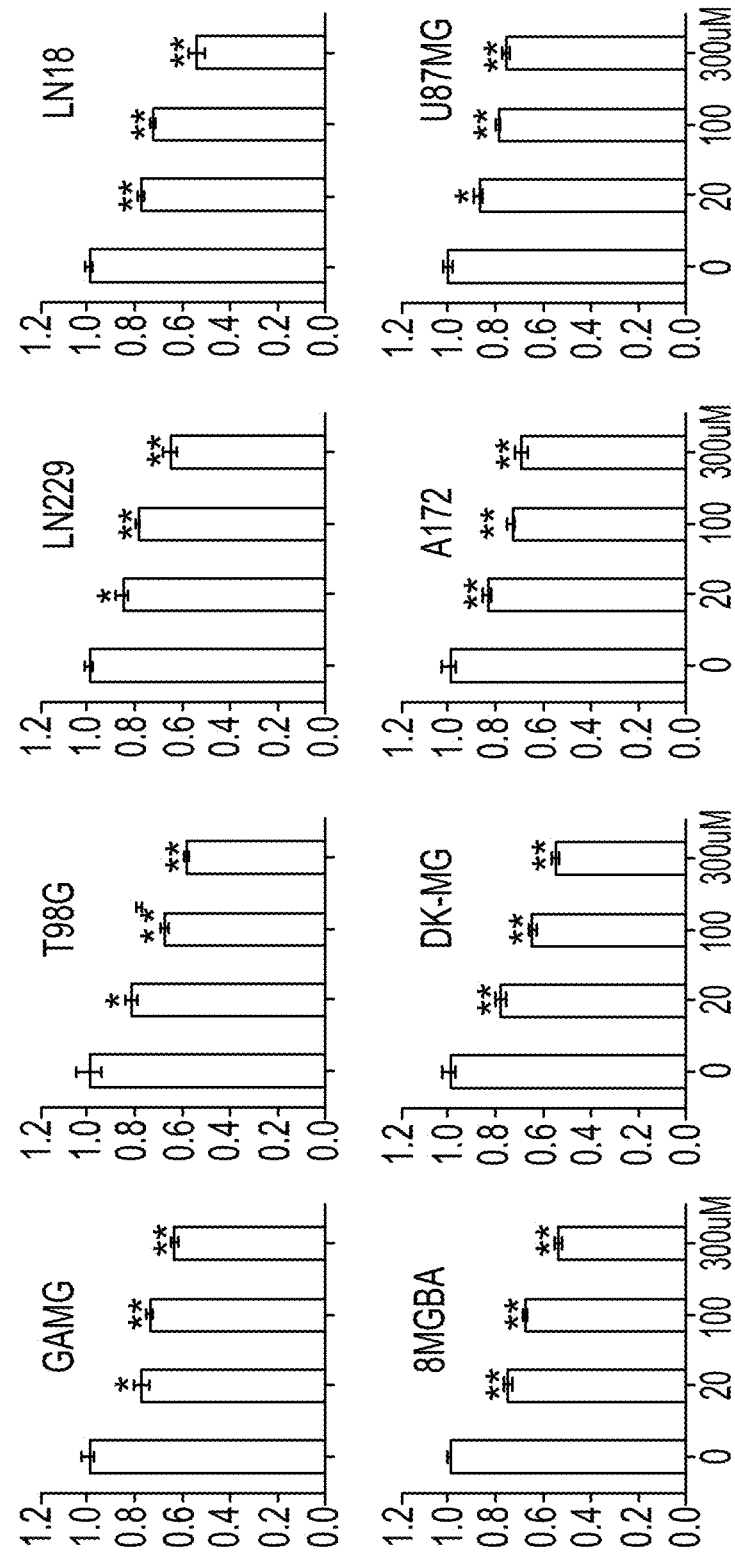
Figure 19C:
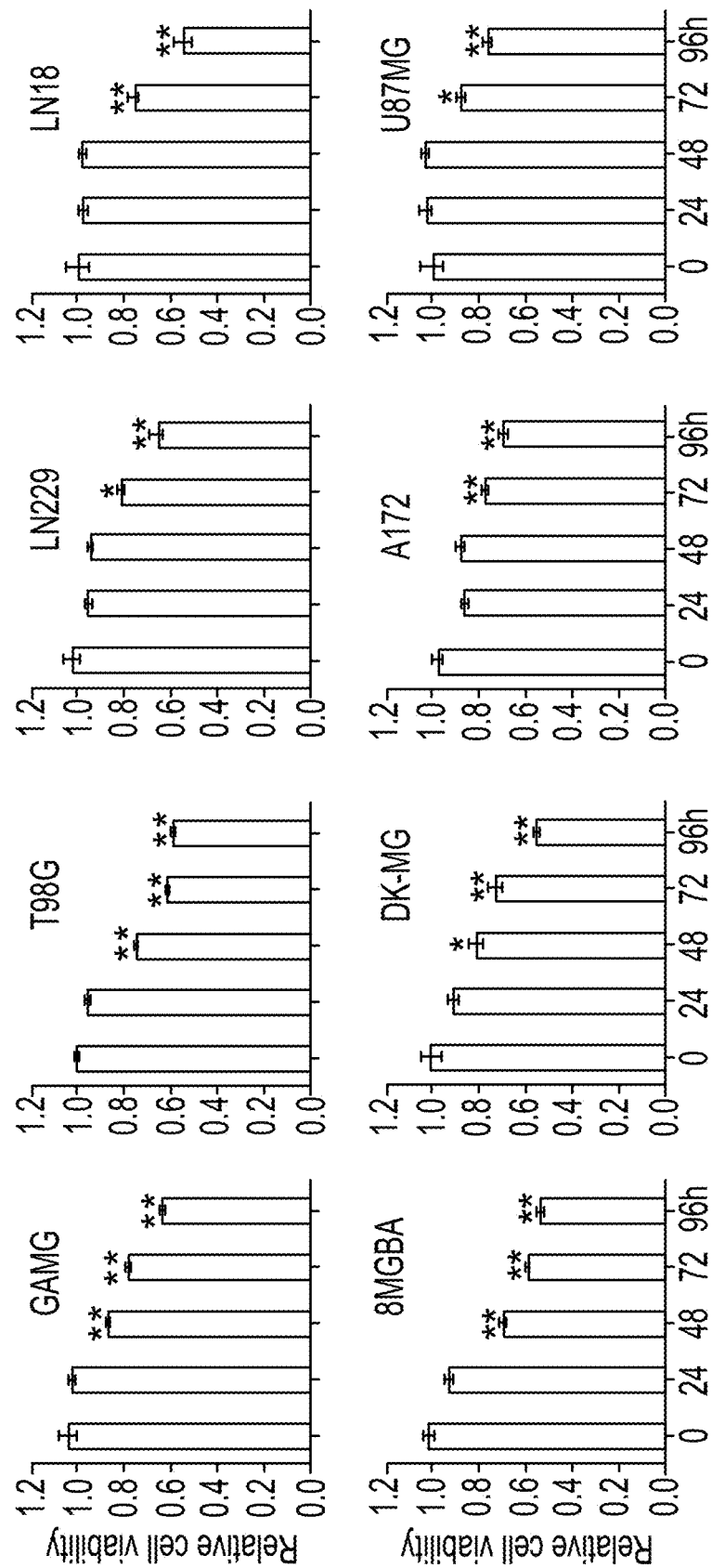

IDH mutations also occur in >70% of patients with lower-grade (II-III) brain tumors and <10% of glioblastomas (grade IV), and such mutations are usually associated with favorable overall survival[1,2,19]. In analysis of the pathological effect of R-2HG in 8 human brain tumor cell lines, R-2HG significantly inhibited the proliferation and viability of all the tumor cells (FIGS. 19A-19C). Thus, these data indicate that R-2HG also exhibits anti-tumor activity in brain tumors, which may contribute to the favorable survival of patients with IDH mutations.

The following references are cited herein to support certain background statements and/or to provide detailed disclosure of known methodologies or mechanistic models and presence on this list should not be construed as an admission of relevance to patentability.

The entire disclosures of all references on this list are incorporated herein by citation.

REFERENCES

1. Yan, H. et al. IDH1 and IDH2 mutations in gliomas. N Engl J Med 360, 765-73 (2009).
2. Cancer Genome Atlas Research, N. et al. Comprehensive, Integrative Genomic Analysis of Diffuse Lower-Grade Gliomas. N Engl J Med 372, 2481-98 (2015).
3. Papaemmanuil, E. et al. Genomic Classification and Prognosis in Acute Myeloid Leukemia. N Engl J Med 374, 2209-21 (2016).
4. Mardis, E. R. et al. Recurring mutations found by sequencing an acute myeloid leukemia genome. N Engl J Med 361, 1058-66 (2009).
5. Thol, F. et al. Prognostic impact of IDH2 mutations in cytogenetically normal acute myeloid leukemia. Blood 116, 614-6 (2010).
6. Luchman, H. A. et al. An in vivo patient-derived model of endogenous IDH1-mutant glioma. Neuro Oncol 14, 184-91 (2012).
7. Dang, L. et al. Cancer-associated IDH1 mutations produce 2-hydroxyglutarate. Nature 462, 739-44 (2009).
8. Ward, P. S. et al. The common feature of leukemia-associated IDH1 and IDH2 mutations is a neomorphic enzyme activity converting alpha-ketoglutarate to 2-hydroxyglutarate. Cancer Cell 17, 225-34 (2010).
9. Xu, W. et al. Oncometabolite 2-hydroxyglutarate is a competitive inhibitor of alpha-ketoglutarate-dependent dioxygenases. Cancer Cell 19, 17-30 (2011).
10. Zhao, S. et al. Glioma-derived mutations in IDH1 dominantly inhibit IDH1 catalytic activity and induce HIF-1alpha. Science 324, 261-5 (2009).
11. Figueroa, M. E. et al. Leukemic IDH1 and IDH2 mutations result in a hypermethylation phenotype, disrupt TET2 function, and impair hematopoietic differentiation. Cancer Cell 18, 553-67 (2010).
12. Lu, C. et al. IDH mutation impairs histone demethylation and results in a block to cell differentiation. Nature 483, 474-8 (2012).
13. Losman, J. A. et al. (R)-2-hydroxyglutarate is sufficient to promote leukemogenesis and its effects are reversible. Science 339, 1621-5 (2013).
14. Suijker, J. et al. Inhibition of mutant IDH1 decreases D-2-HG levels without affecting tumorigenic properties of chondrosarcoma cell lines. Oncotarget 6, 12505-19 (2015).
15. Chen, C. et al. Cancer-associated IDH2 mutants drive an acute myeloid leukemia that is susceptible to Brd4 inhibition. Genes Dev 27, 1974-85 (2013).
16. Tateishi, K. et al. Extreme Vulnerability of IDH1 Mutant Cancers to NAD+ Depletion. Cancer Cell 28, 773-84 (2015).
17. Dohner, H., Weisdorf, D. J. & Bloomfield, C. D. Acute Myeloid Leukemia. N Engl J Med 373, 1136-52 (2015).
18. Im, A. P. et al. DNMT3A and IDH mutations in acute myeloid leukemia and other myeloid malignancies: associations with prognosis and potential treatment strategies. Leukemia 28, 1774-83 (2014).
19. Eckel-Passow, J. E. et al. Glioma Groups Based on 1p/19q, IDH, and TERT Promoter Mutations in Tumors. N Engl J Med 372, 2499-508 (2015).

20. Patel, J. P. et al. Prognostic relevance of integrated genetic profiling in acute myeloid leukemia. *N Engl J Med* 366, 1079-89 (2012).
21. Chou, W. C. et al. The prognostic impact and stability of Isocitrate dehydrogenase 2 mutation in adult patients with acute myeloid leukemia. *Leukemia* 25, 246-53 (2011).
22. Marcucci, G. et al. IDH1 and IDH2 gene mutations identify novel molecular subsets within de novo cytogenetically normal acute myeloid leukemia: a Cancer and Leukemia Group B study. *J Clin Oncol* 28, 2348-55 (2010).
23. Tuck, M. T. The formation of internal 6-methyladenine residues in eucaryotic messenger RNA. *Int J Biochem* 24, 379-86 (1992).
24. Delmore, J. E. et al. BET bromodomain inhibition as a therapeutic strategy to target c-Myc. *Cell* 146, 904-17 (2011).
25. Matozaki, S. et al. Establishment of a myeloid leukaemic cell line (SKNO-1) from a patient with t(8;21) who acquired monosomy 17 during disease progression. *Br J Haematol* 89, 805-11 (1995).
26. Wunderlich, M. et al. AML cells are differentially sensitive to chemotherapy treatment in a human xenograft model. *Blood* 121, e90-7 (2013).
27. Wunderlich, M. et al. AML xenograft efficiency is significantly improved in NOD/SCID-IL2RG mice constitutively expressing human SCF, GM-CSF and IL-3. *Leukemia* 24, 1785-8 (2010).
28. Subramanian, A. et al. Gene set enrichment analysis: a knowledge-based approach for interpreting genome-wide expression profiles. *Proc Natl Acad Sci USA* 102, 15545-50 (2005).
29. Hollern, D. P., Honeysett, J., Cardiff, R. D. & Andrechek, E. R. The E2F transcription factors regulate tumor development and metastasis in a mouse model of metastatic breast cancer. *Mol Cell Biol* 34, 3229-43 (2014).
30. Topham, C. et al. MYC Is a Major Determinant of Mitotic Cell Fate. *Cancer Cell* 28, 129-40 (2015).
31. Sasaki, M. et al. IDH1(R132H) mutation increases murine haematopoietic progenitors and alters epigenetics. *Nature* 488, 656-9 (2012).
32. Chowdhury, R. et al. The oncometabolite 2-hydroxyglutarate inhibits histone lysine demethylases. *EMBO Rep* 12, 463-9 (2011).
33. Jia, G. et al. N6-methyladenosine in nuclear RNA is a major substrate of the obesity-associated FTO. *Nat Chem Biol* 7, 885-7 (2011).
34. Zheng, G. et al. ALKBH5 is a mammalian RNA demethylase that impacts RNA metabolism and mouse fertility. *Mol Cell* 49, 18-29 (2013).
35. Lomenick, B. et al. Target identification using drug affinity responsive target stability (DARTS). *Proc Natl Acad Sci USA* 106, 21984-9 (2009).
36. Dominissini, D., Moshitch-Moshkovitz, S., Salmon-Divon, M., Amariglio, N. & Rechavi, G. Transcriptome-wide mapping of N(6)-methyladenosine by m(6)A-seq based on immunocapturing and massively parallel sequencing. *Nat Protoc* 8, 176-89 (2013).
37. Wang, X. et al. N6-methyladenosine-dependent regulation of messenger RNA stability. *Nature* 505, 117-20 (2014).
38. Nie, Z. et al. c-Myc is a universal amplifier of expressed genes in lymphocytes and embryonic stem cells. *Cell* 151, 68-79 (2012).
39. Lin, C. Y. et al. Transcriptional amplification in tumor cells with elevated c-Myc. *Cell* 151, 56-67 (2012).
40. Ley, T. J. et al. Genomic and epigenomic landscapes of adult de novo acute myeloid leukemia. *N Engl J Med* 368, 2059-74 (2013).
41. Fu, Y. et al. FTO-mediated formation of N6-hydroxymethyladenosine and N6-formyladenosine in mammalian RNA. *Nat Commun* 4, 1798 (2013).
42. Rohle, D. et al. An inhibitor of mutant IDH1 delays growth and promotes differentiation of glioma cells. *Science* 340, 626-30 (2013).
43. Moran-Crusio, K. et al. Tet2 loss leads to increased hematopoietic stem cell self-renewal and myeloid transformation. *Cancer Cell* 20, 11-24 (2011).
44. Emadi, A. et al. Presence of isocitrate dehydrogenase mutations may predict clinical response to hypomethylating agents in patients with acute myeloid leukemia. *Am J Hematol* 90, E77-9 (2015).
45. Boutzen, H. et al. Isocitrate dehydrogenase 1 mutations prime the all-trans retinoic acid myeloid differentiation pathway in acute myeloid leukemia. *J Exp Med* 213, 483-97 (2016).
46. Jiang, X. et al. Blockade of miR-150 maturation by MLL-fusion/MYC/LIN-28 is required for MLL-associated leukemia. *Cancer Cell* 22, 524-35 (2012).
47. Hodge, R. Preparation of RNA dot-blots. *Methods Mol Biol* 86, 73-5 (1998).
48. Lomenick, B., Jung, G., Wohlschlegel, J. A. & Huang, J. Target identification using drug affinity responsive target stability (DARTS). *Curr Protoc Chem Biol* 3, 163-180 (2011).
49. Kim, D et al. TopHat2: accurate alignment of transcriptomes in the presence of insertions, deletions and gene fusions. *Genome Biol* 14, R36 (2013).
50. Zhang, Y. et al. Model-based analysis of ChIP-Seq (MACS). *Genome Biol* 9, R137 (2008).
51. Meng, J. et al. A protocol for RNA methylation differential analysis with MeRIP-Seq data and exomePeak R/Bioconductor package. *Methods* 69, 274-81 (2014).
52. Heinz, S. et al. Simple combinations of lineage-determining transcription factors prime cis-regulatory elements required for macrophage and B cell identities. *Mol Cell* 38, 576-89 (2010).
53. Krzywinski, M. et al. Circos: an information aesthetic for comparative genomics. *Genome Res* 19, 1639-45 (2009).
54. Robinson, J. T. et al. Integrative genomics viewer. *Nat Biotechnol* 29, 24-6 (2011).
55. Trapnell, C. et al. Transcript assembly and quantification by RNA-Seq reveals unannotated transcripts and isoform switching during cell differentiation. *Nat Biotechnol* 28, 511-5 (2010).
56. Trapnell, C. et al. Differential analysis of gene regulation at transcript resolution with RNA-seq. *Nat Biotechnol* 31, 46-53 (2013).
57. Liu, J. et al. A METTL3-METTL14 complex mediates mammalian nuclear RNA N6-adenosine methylation. *Nat Chem Biol* 10, 93-5 (2014).

The invention claimed is:

1. A pharmaceutical composition comprising:
R-2-hydroxyglutarate (R-2HG);
one or more chemotherapeutic agents selected from the group consisting of all trans retinoic acid (ATRA), azacitidine (AZA), daunorubicin, and decitabine; and
a pharmaceutically-acceptable carrier.

2. The pharmaceutical composition of claim 1, further comprising at least one agent that inhibits MYC signaling.

3. The pharmaceutical composition according to claim 2 wherein the at least one agent that inhibits MYC signaling is selected from the agents set forth in Table 4.

4. The pharmaceutical composition according to claim 1, wherein the R-2HG comprises ester-modified R-2HG.

5. The pharmaceutical composition according to claim 1, formulated as an injectable suspension.

6. The pharmaceutical composition according to claim 5, wherein the R-2HG is present in the suspension in a concentration of between about 10 μM and 500 μM, 50 μM and 400 μM, 100 μM and 300 μM, 150 μM and 250 μM, or about 200 μM R-2HG by weight, and is administered in a dose of about 1-10 mg R-2HG per kg body weight.

* * * * *